(12) United States Patent
Malkowski et al.

(10) Patent No.: US 11,076,848 B2
(45) Date of Patent: Aug. 3, 2021

(54) DEVICES, SYSTEMS, AND METHODS FOR PROVIDING SURGICAL ACCESS AND FACILITATING CLOSURE OF SURGICAL ACCESS OPENINGS

(71) Applicant: Covidien LP, Mansfield, MA (US)

(72) Inventors: Jaroslaw T. Malkowski, Trumbull, CT (US); Scott J. Prior, Shelton, CT (US); John D. Hendershot, III, Madison, CT (US); Kenneth W. Horton, South Glastonbury, CT (US); Christopher A. Tokarz, Torrington, CT (US); Danny R. Berry, Cheshire, CT (US); Wayne A. Johnson, Louisville, KY (US)

(73) Assignee: Covidien LP, Mansfield, MA (US)

(*) Notice: Subject to any disclaimer, the term of this patent is extended or adjusted under 35 U.S.C. 154(b) by 83 days.

(21) Appl. No.: 16/240,854

(22) Filed: Jan. 7, 2019

(65) Prior Publication Data

US 2019/0133574 A1    May 9, 2019

Related U.S. Application Data

(62) Division of application No. 14/445,230, filed on Jul. 29, 2014, now Pat. No. 10,201,346.
(Continued)

(51) Int. Cl.
*A61B 17/04* (2006.01)
*A61M 5/32* (2006.01)
(Continued)

(52) U.S. Cl.
CPC ...... *A61B 17/0482* (2013.01); *A61B 17/0057* (2013.01); *A61B 17/0483* (2013.01);
(Continued)

(58) Field of Classification Search
CPC ............... A61M 5/329; A61B 17/0482; A61B 17/0057; A61B 17/0483; A61B 17/3417;
(Continued)

(56) References Cited

U.S. PATENT DOCUMENTS

| | | |
|---|---|---|
| 5,364,410 A | 11/1994 | Failla et al. |
| 5,431,666 A | 7/1995 | Sauer et al. |

(Continued)

FOREIGN PATENT DOCUMENTS

| | | |
|---|---|---|
| CN | 101401720 A | 4/2009 |
| CN | 102065776 A | 5/2011 |

(Continued)

OTHER PUBLICATIONS

Extended European Search Report corresponding to counterpart Int'l Appln. No. 14 83 2198.7 dated Apr. 18, 2017.
(Continued)

*Primary Examiner* — Erich G Herbermann

(57) ABSTRACT

A guide member is configured for guiding a suture passer through a cannula and tissue surrounding the cannula to facilitate closure of an opening in tissue. The guide member includes a guide housing and an elongated guide shaft. The guide housing is configured for releasably engaging the guide member with the cannula and defines an entry aperture. The elongated guide shaft extends distally from the guide housing and defines an annular exterior surface. An exit aperture is defined through the annular exterior surface. The guide member defines a lumen extending from the entry aperture, through the guide housing and the elongated guide shaft, to the exit aperture. The entry aperture, lumen, and exit aperture cooperating to define a passageway extending through the guide member.

10 Claims, 44 Drawing Sheets

Related U.S. Application Data

(60) Provisional application No. 62/029,809, filed on Jul. 28, 2014, provisional application No. 62/029,788, filed on Jul. 28, 2014, provisional application No. 62/029,839, filed on Jul. 28, 2014, provisional application No. 62/029,825, filed on Jul. 28, 2014, provisional application No. 61/861,732, filed on Aug. 2, 2013.

(51) Int. Cl.
  *A61B 17/34* (2006.01)
  *A61B 17/00* (2006.01)
  *A61B 90/70* (2016.01)
  *A61M 19/00* (2006.01)
  *A61M 13/00* (2006.01)
  *A61B 90/00* (2016.01)

(52) U.S. Cl.
  CPC ...... *A61B 17/3417* (2013.01); *A61B 17/3468* (2013.01); *A61B 90/70* (2016.02); *A61M 5/329* (2013.01); *A61B 17/3462* (2013.01); *A61B 90/361* (2016.02); *A61B 2017/00349* (2013.01); *A61B 2017/00637* (2013.01); *A61B 2017/00663* (2013.01); *A61B 2017/00907* (2013.01); *A61B 2017/3405* (2013.01); *A61B 2017/347* (2013.01); *A61B 2017/3411* (2013.01); *A61B 2017/3441* (2013.01); *A61B 2017/3445* (2013.01); *A61B 2017/3454* (2013.01); *A61B 2090/036* (2016.02); *A61B 2090/08021* (2016.02); *A61B 2090/701* (2016.02); *A61M 13/00* (2013.01); *A61M 19/00* (2013.01)

(58) Field of Classification Search
  CPC . A61B 17/3468; A61B 17/3462; A61B 90/70; A61B 90/361; A61B 2090/08021; A61B 2090/701; A61B 2017/00394; A61B 2017/00637; A61B 2017/00663; A61B 2017/00907; A61B 2017/3405; A61B 2017/3411; A61B 2017/3441; A61B 2017/3445; A61B 2017/3454; A61B 2017/347
  See application file for complete search history.

(56) References Cited

U.S. PATENT DOCUMENTS

| | | | |
|---|---|---|---|
| 5,499,997 A | 3/1996 | Sharpe et al. | |
| 5,507,755 A | 4/1996 | Gresl et al. | |
| 5,507,758 A | 4/1996 | Thomason et al. | |
| 5,522,846 A | 6/1996 | Bonutti | |
| 5,540,704 A | 7/1996 | Gordon et al. | |
| 5,562,688 A * | 10/1996 | Riza | A61B 17/0469 606/139 |
| 5,613,974 A | 3/1997 | Andreas et al. | |
| 5,653,716 A | 8/1997 | Malo et al. | |
| 5,700,273 A | 12/1997 | Buelna et al. | |
| 5,716,369 A | 2/1998 | Riza | |
| 5,741,278 A | 4/1998 | Stevens | |
| 5,772,672 A | 6/1998 | Toy et al. | |
| 5,814,065 A | 9/1998 | Diaz | |
| 5,817,108 A | 10/1998 | Poncet | |
| 5,817,111 A | 10/1998 | Riza | |
| 5,836,955 A | 11/1998 | Buelna et al. | |
| 5,860,990 A | 1/1999 | Nobles et al. | |
| 5,899,911 A | 5/1999 | Carter | |
| 5,954,734 A | 9/1999 | Thomason et al. | |
| 5,993,471 A | 11/1999 | Riza et al. | |
| 5,993,474 A | 11/1999 | Ouchi | |
| 6,022,360 A | 2/2000 | Reimels et al. | |
| 6,099,550 A | 8/2000 | Yoon | |
| 6,110,185 A | 8/2000 | Barra et al. | |
| 6,117,144 A | 9/2000 | Nobles et al. | |
| 6,183,485 B1 | 2/2001 | Thomason et al. | |
| 6,641,592 B1 | 11/2003 | Sauer et al. | |
| 6,743,242 B2 | 6/2004 | Guo | |
| 7,842,049 B2 | 11/2010 | Voss | |
| 8,109,943 B2 | 2/2012 | Boraiah et al. | |
| 8,172,801 B2 | 5/2012 | Adams | |
| 9,033,872 B2 | 5/2015 | Mohajer-Shojaee | |
| 10,201,346 B2 | 2/2019 | Malkowski et al. | |
| 2004/0068273 A1 | 4/2004 | Fariss et al. | |
| 2004/0087978 A1 | 5/2004 | Velez et al. | |
| 2005/0212221 A1 | 9/2005 | Smith et al. | |
| 2005/0228405 A1 | 10/2005 | Maruyama et al. | |
| 2006/0135991 A1 | 6/2006 | Kawaura et al. | |
| 2006/0142784 A1 | 6/2006 | Kontos | |
| 2007/0088247 A1 | 4/2007 | Bliweis et al. | |
| 2007/0250112 A1 | 10/2007 | Ravikumar et al. | |
| 2008/0255576 A1 * | 10/2008 | Protopsaltis | A61B 17/7091 606/104 |
| 2010/0012152 A1 | 1/2010 | Hansen | |
| 2010/0016870 A1 | 1/2010 | Campbell | |
| 2010/0179572 A1 | 7/2010 | Voss et al. | |
| 2010/0262166 A1 | 10/2010 | Boraiah et al. | |
| 2011/0082475 A1 | 4/2011 | Smith | |
| 2011/0112557 A1 | 5/2011 | Beeley | |
| 2011/0237901 A1 | 9/2011 | Duke et al. | |
| 2011/0245850 A1 | 10/2011 | van der Burg et al. | |
| 2011/0288563 A1 | 11/2011 | Gianotti et al. | |
| 2012/0029532 A1 | 2/2012 | Hodgkinson et al. | |
| 2012/0035623 A1 | 2/2012 | Bagaoisan et al. | |
| 2012/0143221 A1 | 6/2012 | Weisel et al. | |
| 2012/0265223 A1 | 10/2012 | Shpaichler et al. | |
| 2013/0006277 A1 | 1/2013 | Stafford | |
| 2013/0079597 A1 | 3/2013 | Auerbach et al. | |
| 2013/0165956 A1 | 6/2013 | Sherts et al. | |

FOREIGN PATENT DOCUMENTS

| | | |
|---|---|---|
| EP | 2305151 A1 | 4/2011 |
| EP | 2412317 A1 | 2/2012 |
| EP | 2547270 A1 | 1/2013 |
| JP | 5086305 | 11/1993 |
| WO | 9502998 A1 | 2/1995 |
| WO | 2006111955 A2 | 10/2006 |
| WO | 2011128392 A1 | 10/2011 |
| WO | 2012093094 A1 | 7/2012 |
| WO | 2013105993 A2 | 7/2013 |

OTHER PUBLICATIONS

International Search Report from corresponding PCT/US2014/048892 dated Nov. 25, 2014.
International Search Report from corresponding PCT/US2014/048919 dated Nov. 7, 2014.
International Search Report from corresponding PCT/US2014/048907 dated Nov. 12, 2014.
Extended European Search Report corresponding to counterpart Int'l Appln. No. EP 14 83 2198.7 dated Apr. 18, 2017.
Extended European Search Report corresponding to counterpart Int'l Appln. No. EP 14 83 1785.2 dated Mar. 17, 2017.
Chinese Office Action and Search Report (with English translation), dated Aug. 23, 2017, corresponding to Chinese Application No. 201480043332.6; 16 total pages.
European Search Report dated Nov. 30, 2017, corresponding to European Application No. 148313681.7; 18 total pages.
Japanese Office Action (with English translation) dated Mar. 13, 2018, corresponding to Japanese Application No. 2016-531858; 18 total pages.
Chinese Office Action and Search Report (with English translation), dated Apr. 25, 2018, corresponding to counterpart Chinese Application No. 201480043332.6; 18 total pages.
Japanese Office Action (with English translation) dated May 8, 2019, corresponding to counterpart Japanese Application No. 2016-531858; 12 total pages.

(56) References Cited

OTHER PUBLICATIONS

Japanese Office Action dated Oct. 2, 2020, issued in corresponding Japanese Appln. No. 2019156548, 9 pages.
Canadian Office Action dated Apr. 14, 2021, issued in corresponding CA Appln. No. 2,918,244, 4 pages.
Japanese Office Action dated May 7, 2021, issued in corresponding JP Appln. No. 2019156548, 5 pages.

* cited by examiner

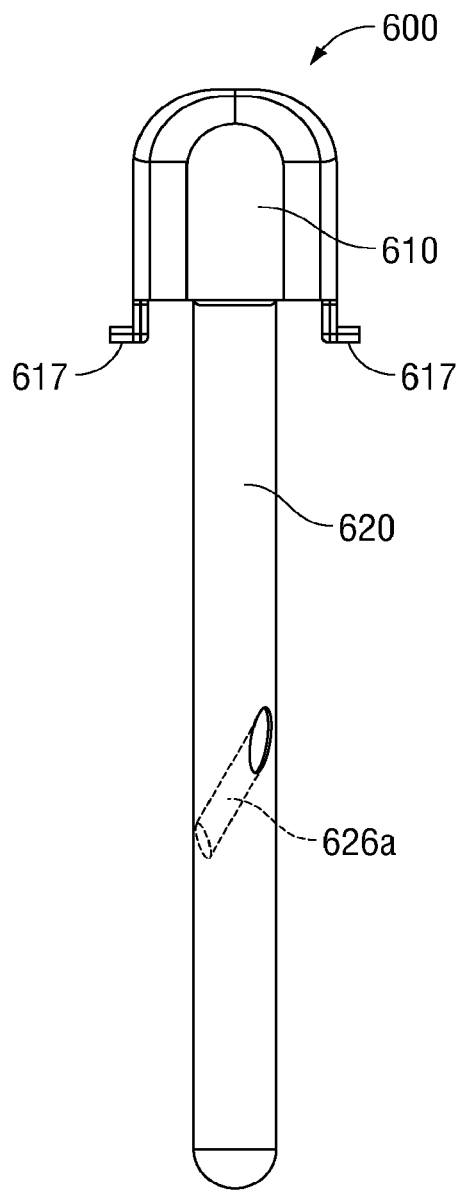 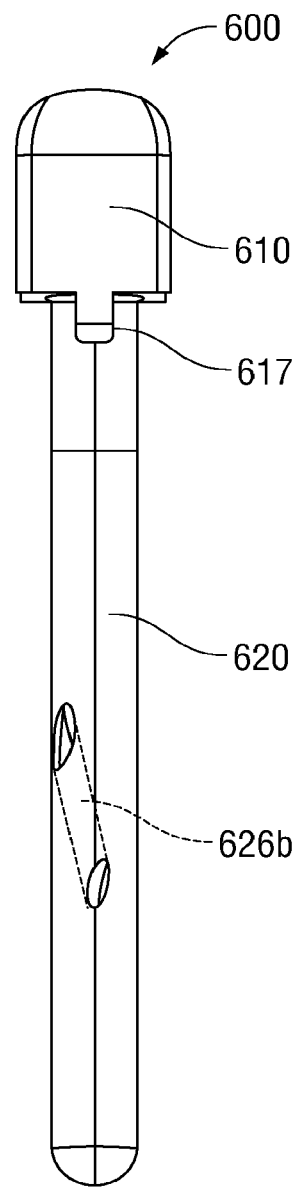
FIG. 14A   FIG. 14B

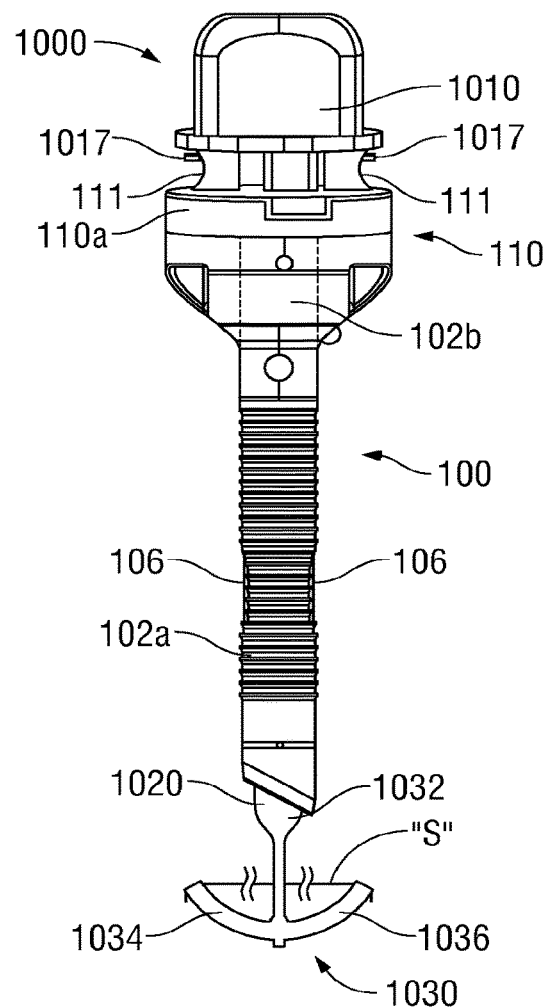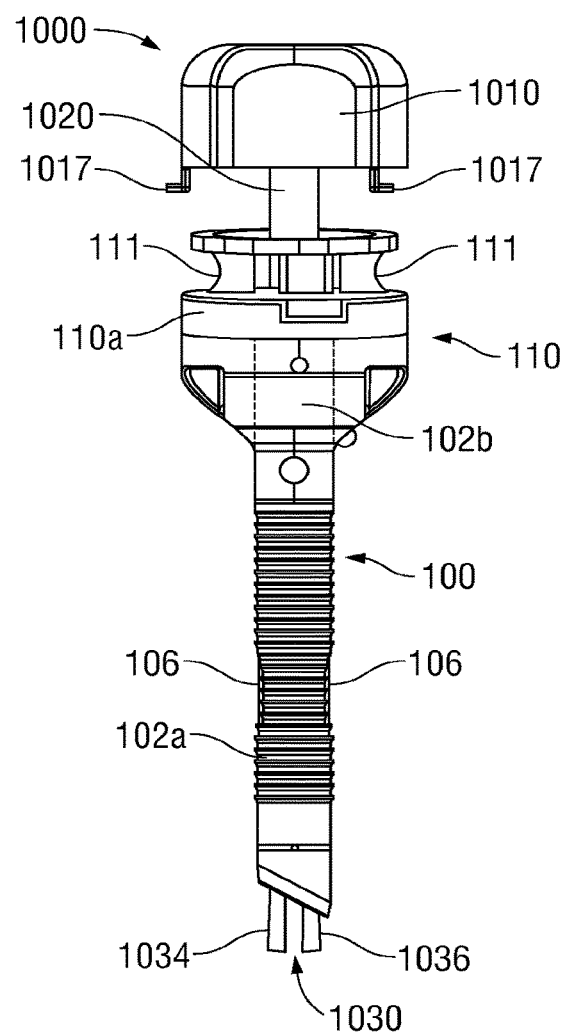
FIG. 24D  FIG. 24E

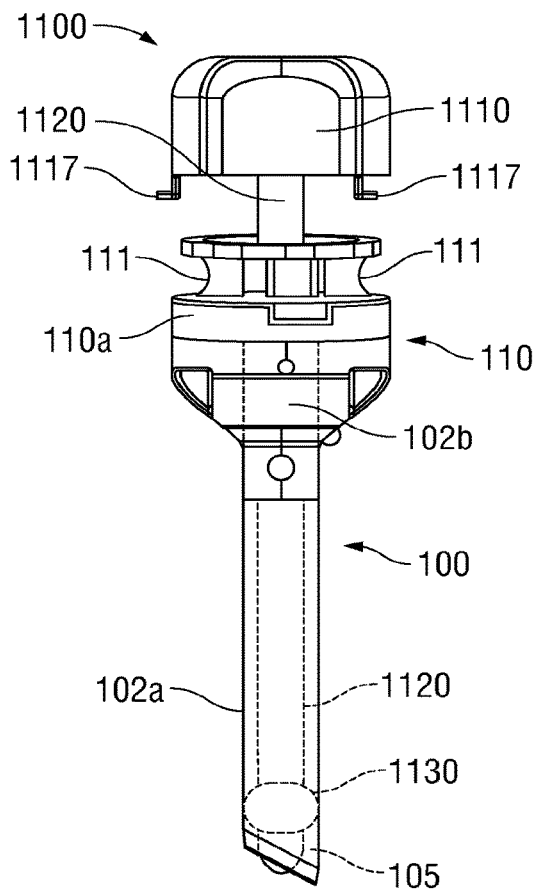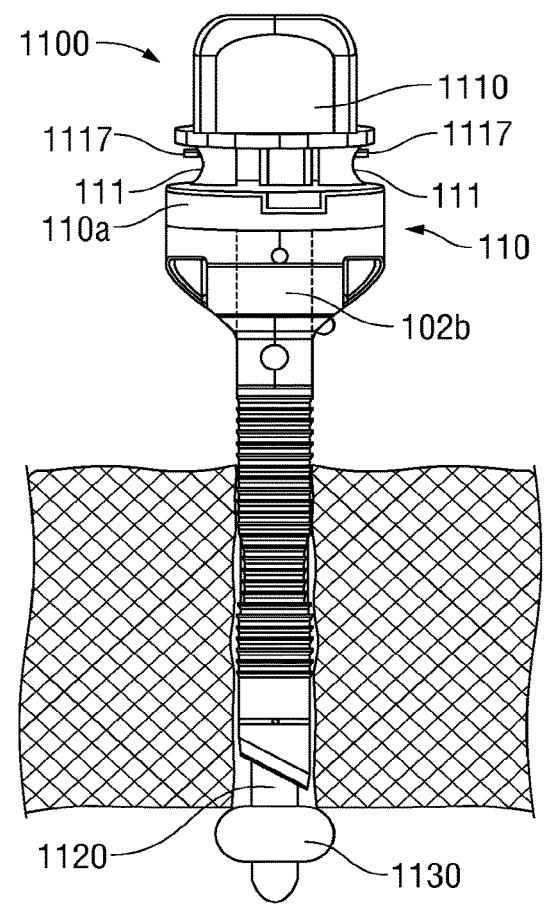
FIG. 30B
FIG. 30C

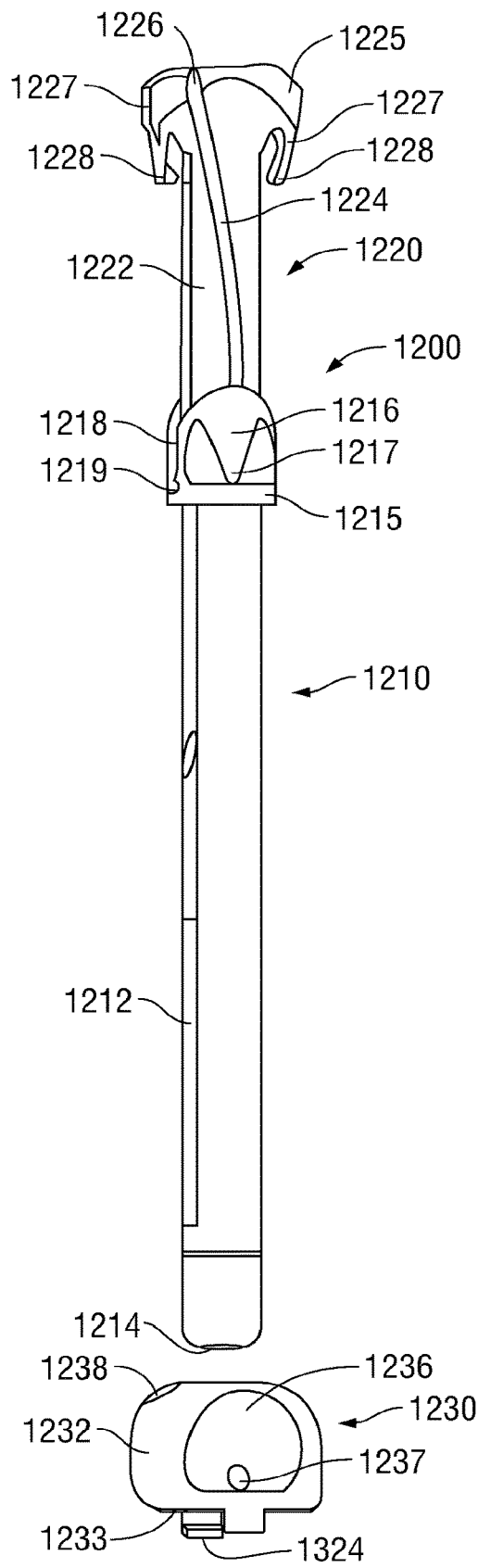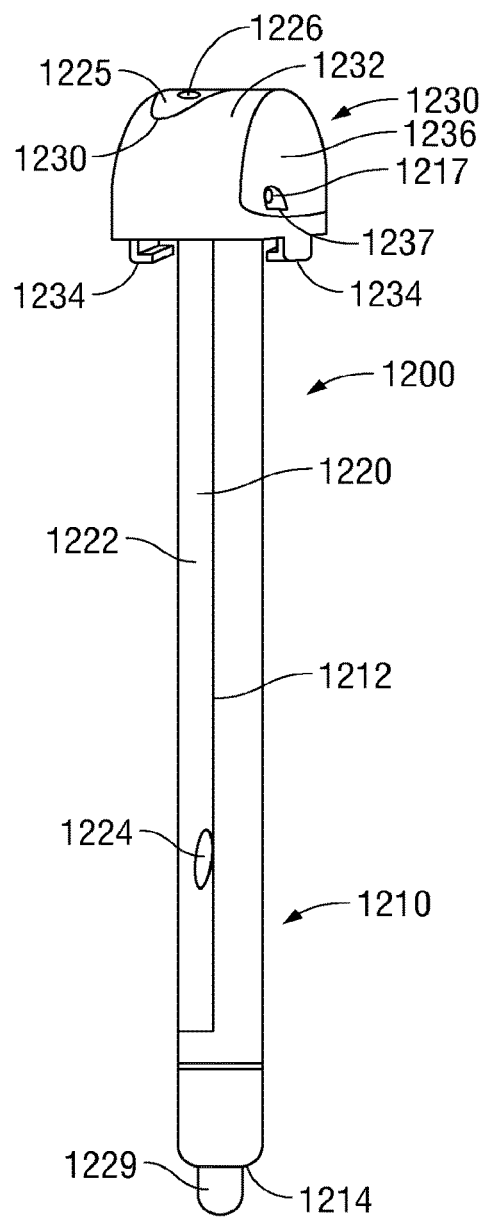
FIG. 31A
FIG. 31B

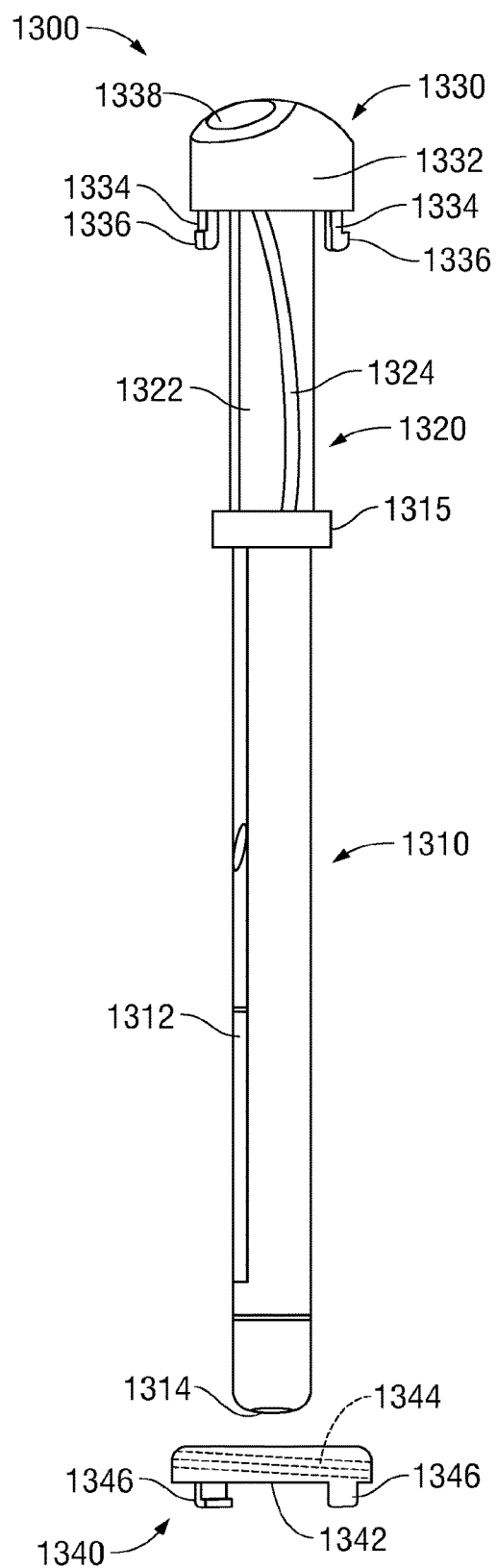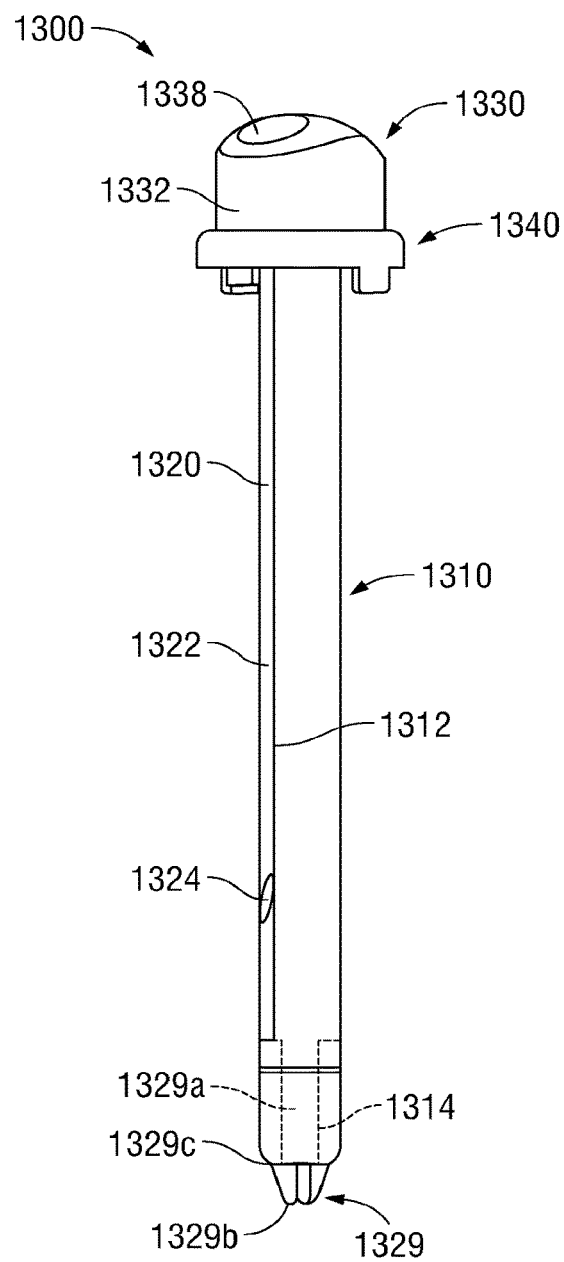
FIG. 32A  FIG. 32B

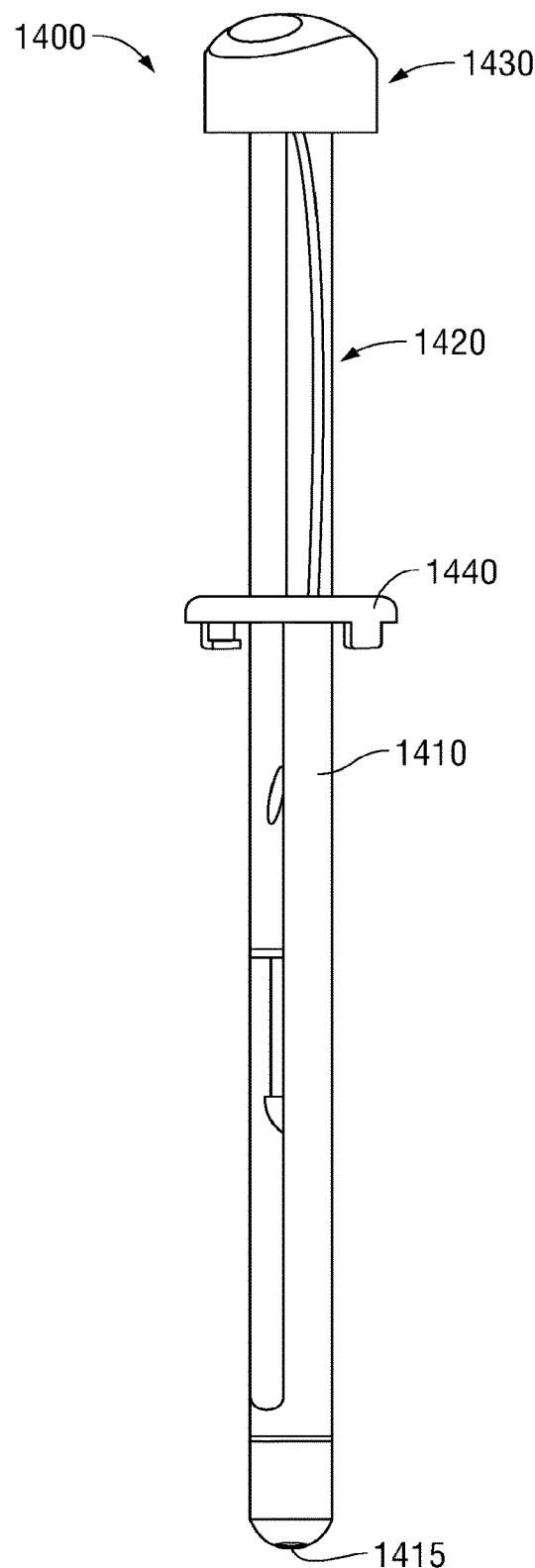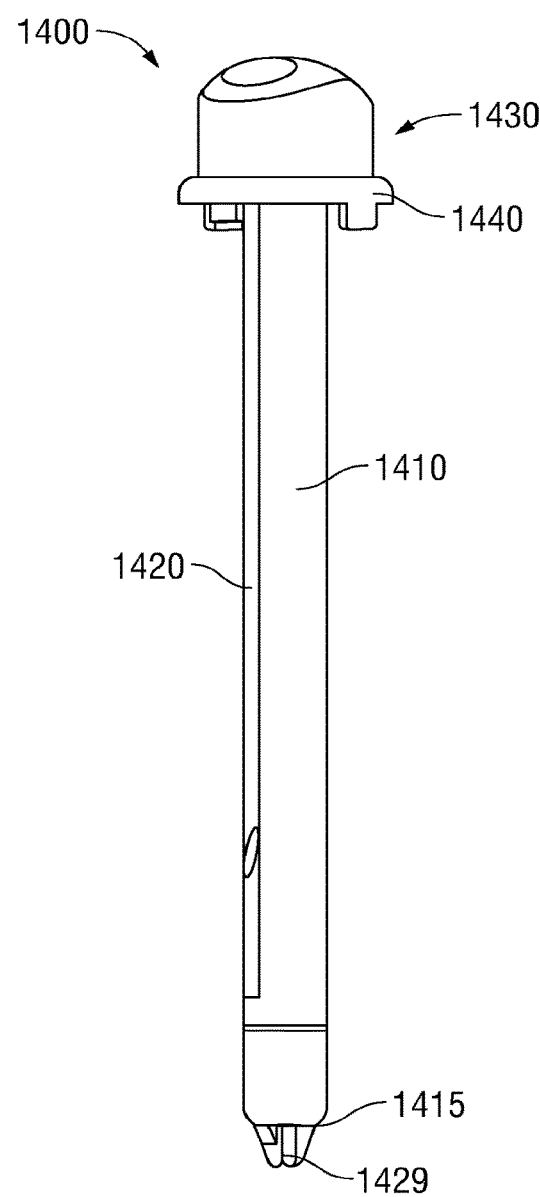
FIG. 33A
FIG. 33B

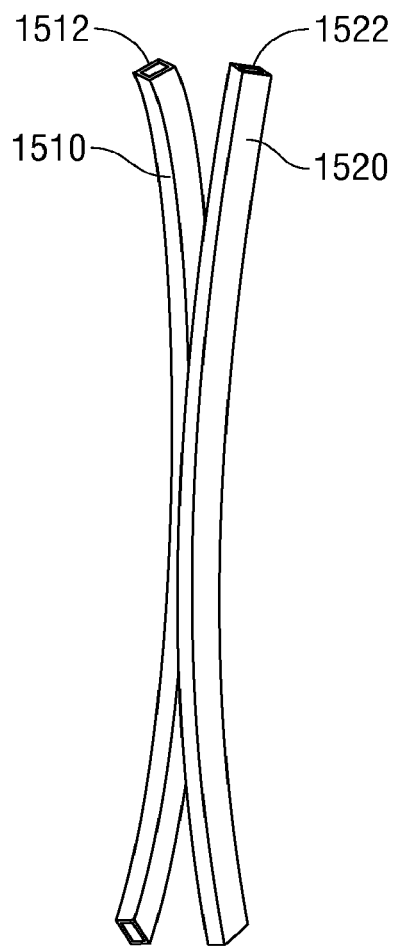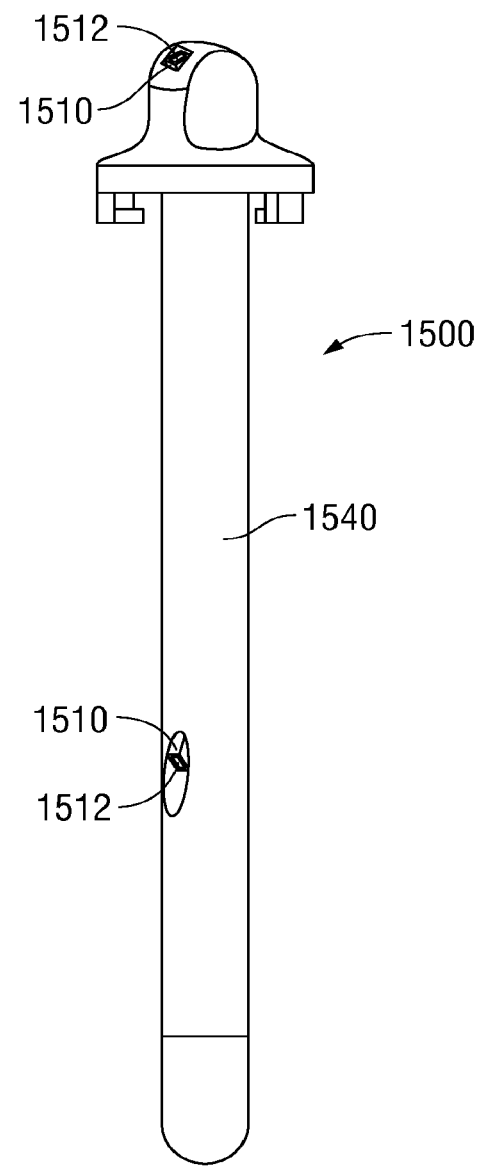
FIG. 34A
FIG. 34B

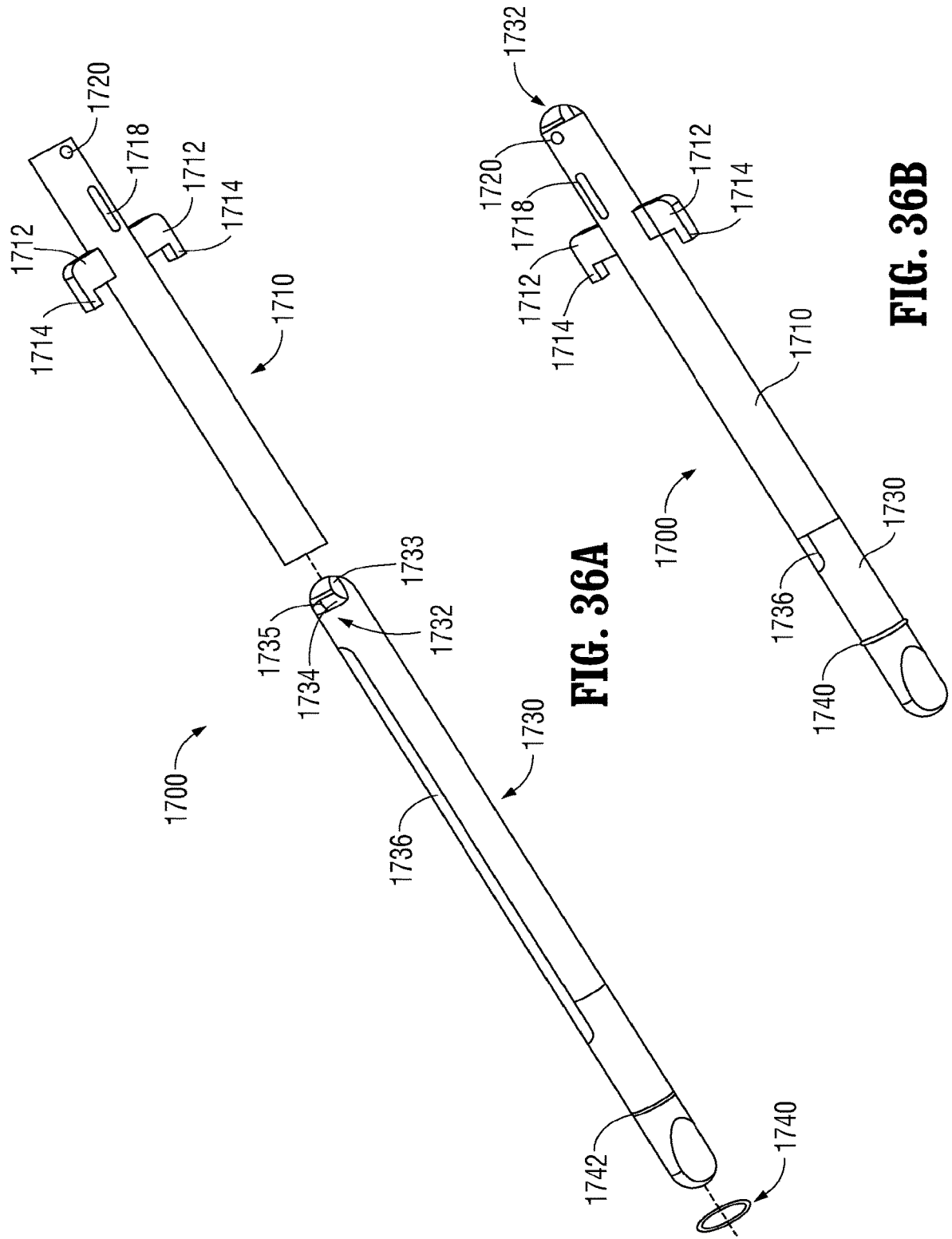

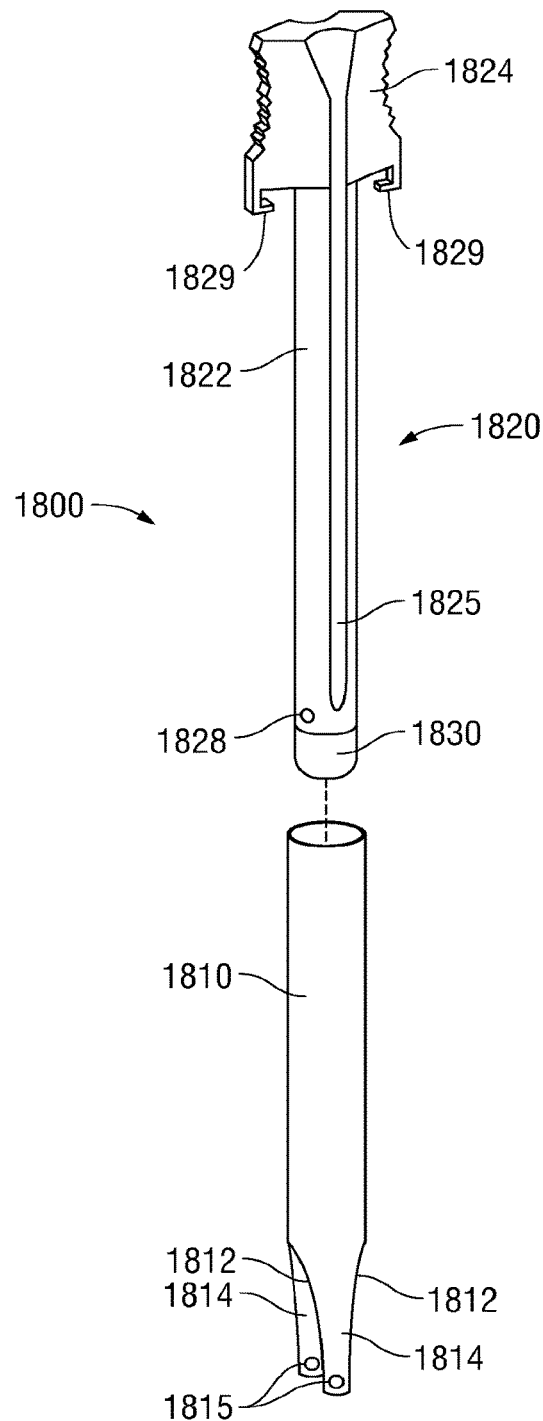
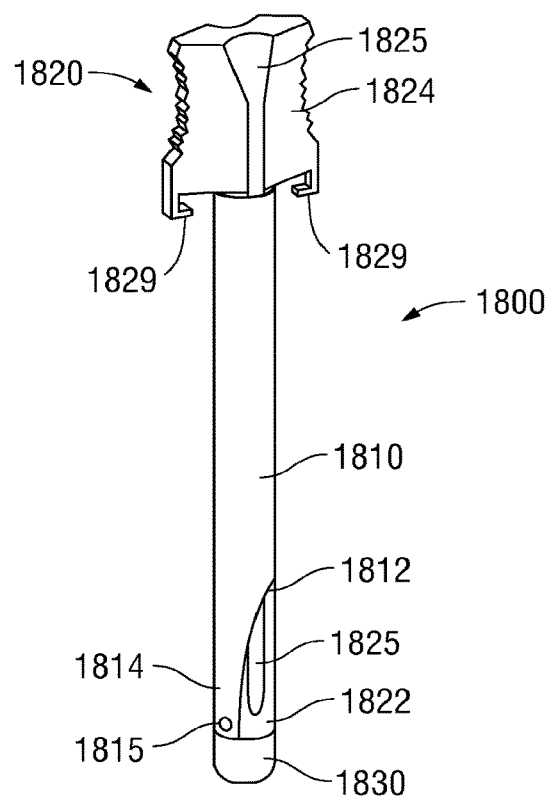
FIG. 37A
FIG. 37B

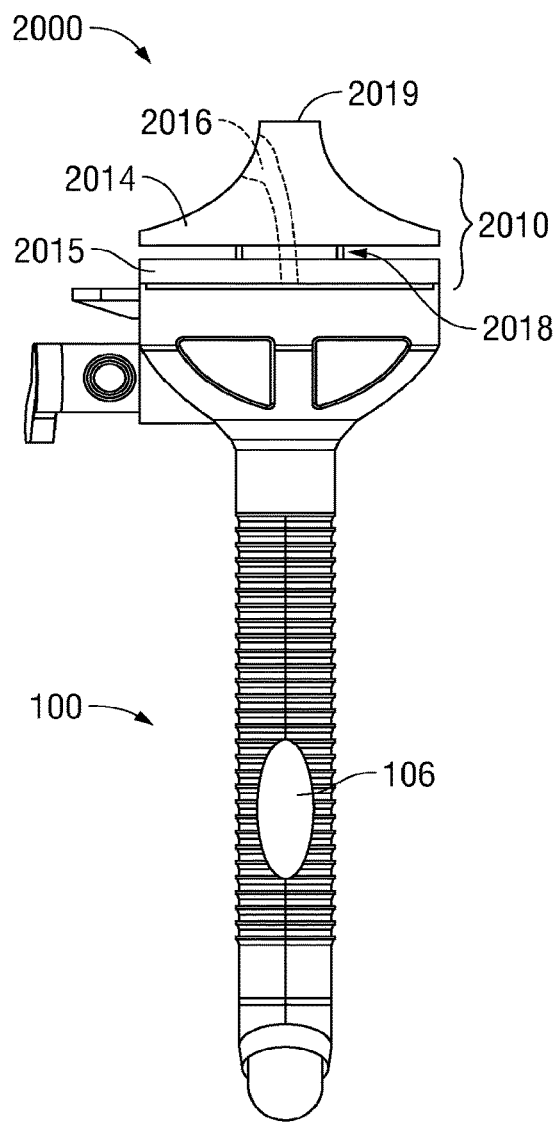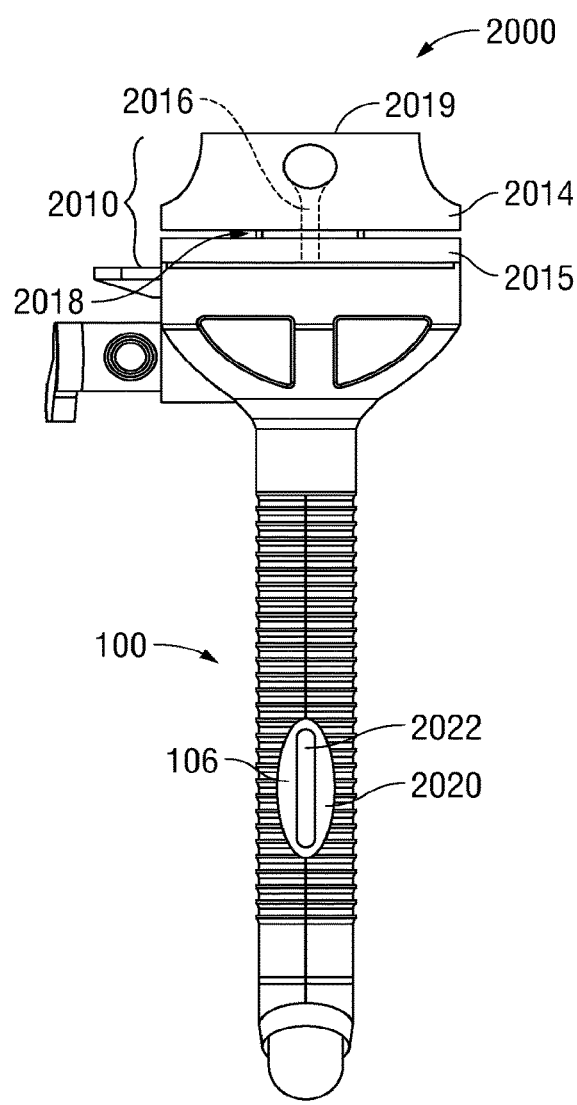
FIG. 39A  FIG. 39B

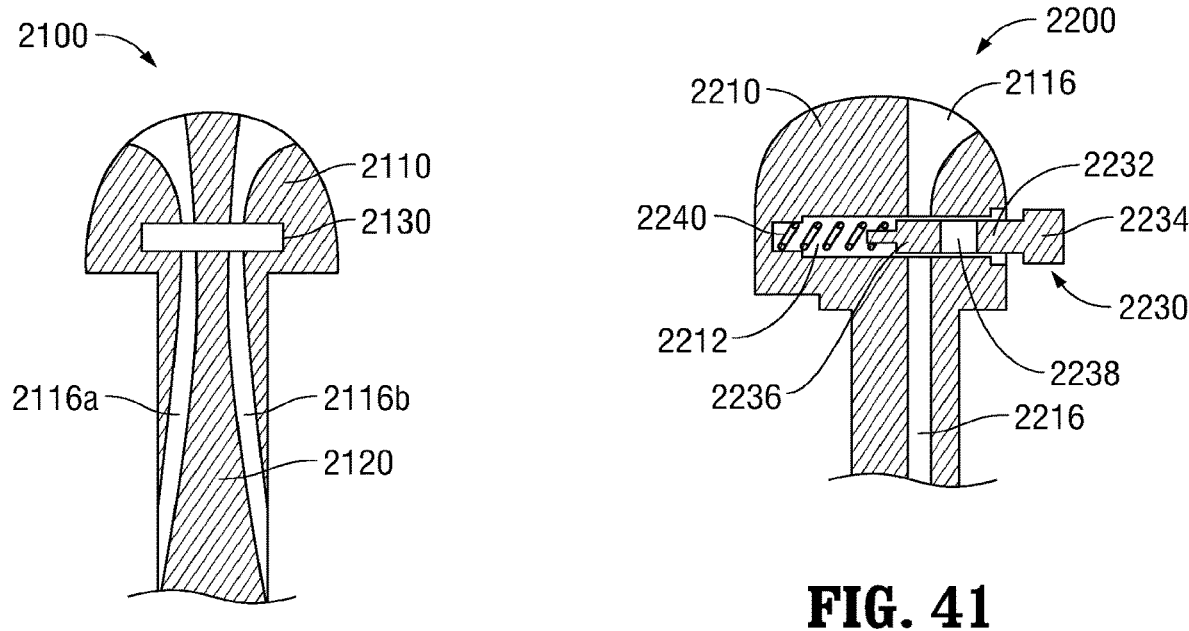
FIG. 40
FIG. 41
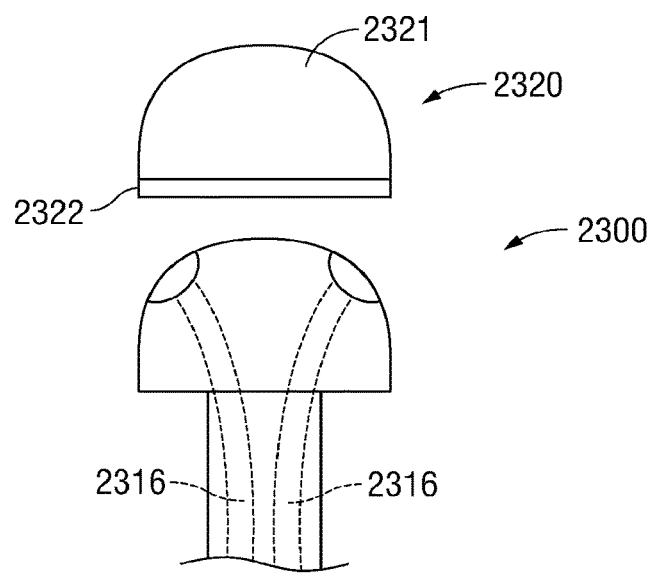
FIG. 42

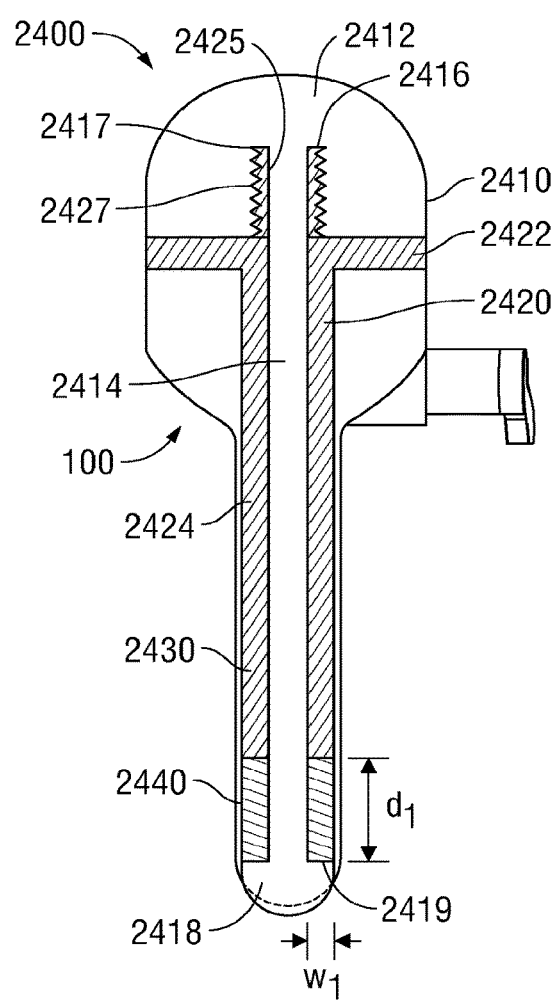
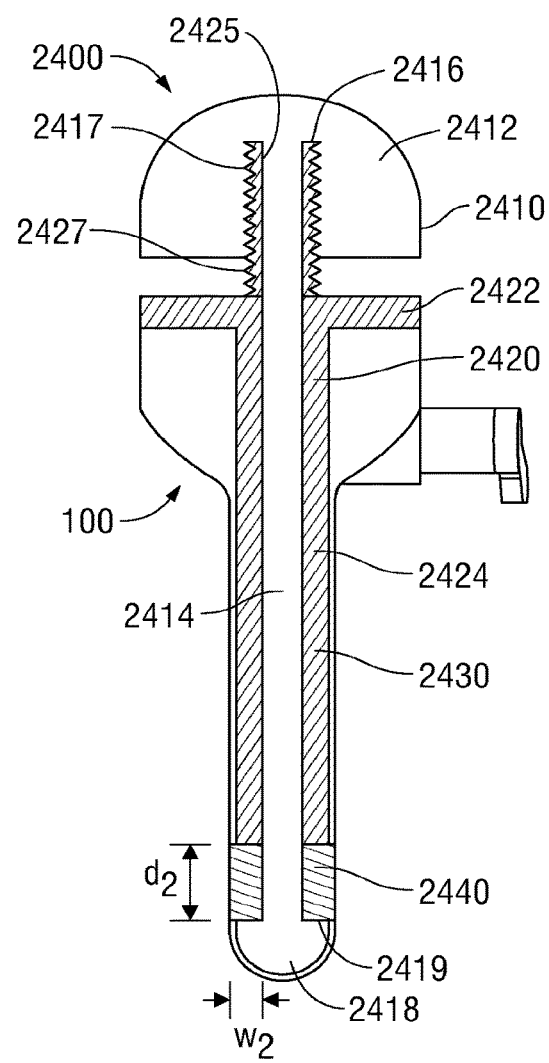
FIG. 43A  FIG. 43B

DEVICES, SYSTEMS, AND METHODS FOR PROVIDING SURGICAL ACCESS AND FACILITATING CLOSURE OF SURGICAL ACCESS OPENINGS

CROSS-REFERENCE TO RELATED APPLICATIONS

This application is a divisional of U.S. patent application Ser. No. 14/445,230 filed Jul. 29, 2014, which claims benefit of and priority to U.S. Provisional Application No. 62/029,809 filed Jul. 28, 2014, U.S. Provisional Application No. 62/029,788 filed Jul. 28, 2014, U.S. Provisional Application No. 62/029,839 filed Jul. 28, 2014, U.S. Provisional Application No. 62/029,825 filed Jul. 28, 2014 and U.S. Provisional Application No. 61/861,732 filed Aug. 2, 2013, and the disclosures of each of the above-identified applications are hereby incorporated by reference in their entirety.

This application is related to U.S. patent application Ser. No. 14/445,396, filed on Jul. 29, 2014 (now U.S. Pat. No. 9,714,126), U.S. patent application Ser. No. 14/445,197, filed on Jul. 29, 2014 (now U.S. Pat. No. 9,918,712), and U.S. patent application Ser. No. 14/445,259, filed on Jul. 29, 2014 (now U.S. Pat. No. 9,700,303).

BACKGROUND

Technical Field

The present disclosure relates to surgical access and closure of surgical access openings and, more particularly, to devices, systems, and methods that provide access to an internal surgical site through an opening in tissue and facilitate the closure of the opening in tissue.

Background of Related Art

Puncture wounds, wounds that pierce through tissue, may result from trauma or may be intentionally created in order to provide a surgical access opening for accessing an internal surgical site of a patient during surgical procedures. During endoscopic surgical procedures, for example, a trocar device is utilized to puncture the peritoneum to provide access by way of a cannula through the abdominal wall. Generally, a trocar and/or cannula is placed through the abdominal wall for introduction of surgical instrumentation which is necessary to carry out one or more surgical tasks. In this manner, the surgeon may introduce a surgical instrument such as a forceps, scissors, clip applier, stapler, biopsy device, or any other surgical instrument as necessary to complete a particular surgical task or tasks. Once the task(s) is complete, it is necessary to close the opening.

SUMMARY

The present disclosure provides devices, systems, and methods that facilitate accessing an internal surgical site through an opening in tissue, performing one or more minimally-invasive surgical tasks within the internal surgical site, and closing the opening in tissue once the surgical task(s) is complete. In particular, in accordance with aspects of the present disclosure, a guide member configured for guiding a suture passer through a cannula and tissue surrounding the cannula to facilitate closure of an opening in tissue is provided including a guide housing and an elongated guide shaft. The guide housing is configured for releasably engaging the guide member with the cannula and defines a first entry aperture. The elongated guide shaft extends distally from the guide housing and defines an annular exterior surface. A first exit aperture is defined through the annular exterior surface. The guide member further defines a first lumen extending from the first entry aperture, through the guide housing and the elongated guide shaft, to the first exit aperture. The first entry aperture, first lumen, and first exit aperture cooperate to define a first passageway extending through the guide member.

In aspects, the first passageway extending through the guide member defines a linear path. Alternatively, the first passageway extending through the guide member may define a curved path having a constant radius of curvature or a varying radius of curvature.

In aspects, the guide housing defines a second entry aperture, the elongated guide shaft defines a second exit aperture, and the guide member defines a second lumen extending from the second entry aperture, through the guide housing and the elongated guide shaft, to the second exit aperture. The second entry aperture, second lumen, and second exit aperture cooperate to define a second passageway extending through the guide member. The first and second passageways may overlap one another without intersecting one another, or may be both non-overlapping and non-intersecting. Other configurations of the passageways are also contemplated.

In aspects, the elongated guide shaft includes a suture-retaining member disposed towards a distal end of the elongated guide shaft. The suture-retaining member is configured to retain a portion of a suture thereon.

In aspects, the elongated guide shaft includes a cleaning member disposed towards a distal end of the elongated guide shaft. The cleaning member is configured to wipe against an interior surface of the cannula upon insertion of the elongated guide shaft through the cannula.

In aspects, a sealing member is disposed within the first entry aperture, first lumen, or first exit aperture. The sealing member is configured to seal the first passageway in the absence of the suture passer inserted through the first passageway and to establish a seal about the suture passer when the suture passer is inserted through the first passageway.

In aspects, the guide housing is rotatably coupled to the elongated guide shaft and is rotatable relative to the elongated guide shaft between a first position, wherein a proximal portion of the passageway is disconnected from a distal portion of the passageway, and a second position, wherein the proximal portion of the passageway is aligned with the distal portion of the passageway to fully form the passageway.

In aspects, the guide member includes a first component and a second component. Each of the first and second components includes a portion of the guide housing, the first entry aperture, the elongated guide shaft, the first exit aperture, and the first lumen. The first and second components are engagable with each other and, as such, fully form the guide housing, the first entry aperture, the elongated guide shaft, the first exit aperture, and the first lumen upon engagement with each other.

Another guide member provided in accordance with aspects of the present disclosure is also configured for guiding a suture passer through a cannula and tissue surrounding the cannula to facilitate closure of an opening in tissue. The guide member includes an inner shaft and an outer sleeve. The inner shaft defines an entry opening, an exit opening, and a channel extending between the entry opening and the exit opening. The outer sleeve is disposed about the inner shaft and is positioned to enclose at least a portion of the channel to define a passageway extending between the entry opening and the exit opening.

In aspects, a ring is positionable about the inner shaft and the outer sleeve to secure the inner shaft and the outer sleeve to one another. Alternatively, a cap may be positionable about the inner shaft and the outer sleeve to secure the inner shaft and the outer sleeve to one another. The ring or cap, where so provided, may further be configured to releasably engage the cannula upon insertion of the guide member into the cannula.

The outer sleeve may be configured to engage the inner shaft, for example, via a snap-fit engagement, a track and slider engagement, or a protrusion-recess engagement.

Any of the above aspects, to the extent consistent, may be utilized with any or all of the other aspects detailed herein.

BRIEF DESCRIPTION OF THE DRAWINGS

Various aspects and features of the present disclosure are described hereinbelow with references to the drawings, wherein:

FIG. 14A is a first side view of the guide member of FIG. 13;

FIG. 14B is a second side view rotated 90 degrees of the guide member of FIG. 13;

FIG. 24D is a side view of the guide member of FIG. 23 fully inserted into and engaged with the cannula of FIG. 4A;

FIG. 24E is a side view of the guide member of FIG. 23 being withdrawn from the cannula of FIG. 4A;

FIG. 30B is a side view of the guide member of FIG. 29 being inserted into the cannula of FIG. 4A;

FIG. 30C is a side view of the guide member of FIG. 29 fully engaged within the cannula of FIG. 4A and positioned within an opening in tissue;

FIG. 31A is an exploded, perspective view of another guide member provided in accordance with the present disclosure;

FIG. 31B is a perspective view of the guide member of FIG. 31A as assembled;

FIG. 32A is an exploded, perspective view of another guide member provided in accordance with the present disclosure;

FIG. 32B is a perspective view of the guide member of FIG. 32A as assembled;

FIG. 33A is an exploded, perspective view of another guide member provided in accordance with the present disclosure;

FIG. 33B is a perspective view of the guide member of FIG. 33A as assembled;

FIG. 34A is a perspective view of an insert forming part of and utilized in the manufacture of a guide member in accordance with the present disclosure;

FIG. 34B is a perspective view of a guide member provided in accordance with the present disclosure and formed utilizing the insert of FIG. 34A;

FIG. 36A is an exploded, perspective view of another guide member provided in accordance with the present disclosure;

FIG. 36B is a perspective view of the guide member of FIG. 36A as assembled;

FIG. 37A is an exploded, perspective view of another guide member provided in accordance with the present disclosure;

FIG. 37B is a perspective view of the guide member of FIG. 37A as assembled;

FIG. 39A is a side view of another guide member provided in accordance with the present disclosure engaged within the cannula of FIG. 4A and disposed in a first position relative to the cannula;

FIG. 39B is a side view of the guide member and cannula shown in FIG. 39A wherein the guide member is disposed in a second position relative to the cannula;

FIG. 40 is a longitudinal, cross-sectional view of the proximal end of another guide member provided in accordance with the present disclosure;

FIG. 41 is a longitudinal, cross-sectional view of the proximal end of another guide member provided in accordance with the present disclosure;

FIG. 42 is an exploded, side view of the proximal end of another guide member provided in accordance with the present disclosure;

FIG. 43A is a longitudinal, cross-sectional view of another guide member provided in accordance with the present disclosure engaged within the cannula of FIG. 4A and disposed in a first position relative to the cannula;

FIG. 43B is a longitudinal, cross-sectional view of the guide member and cannula shown in FIG. 43A, wherein the guide member is disposed in a second position relative to the cannula.

DETAILED DESCRIPTION OF THE EMBODIMENTS

Figure 1:
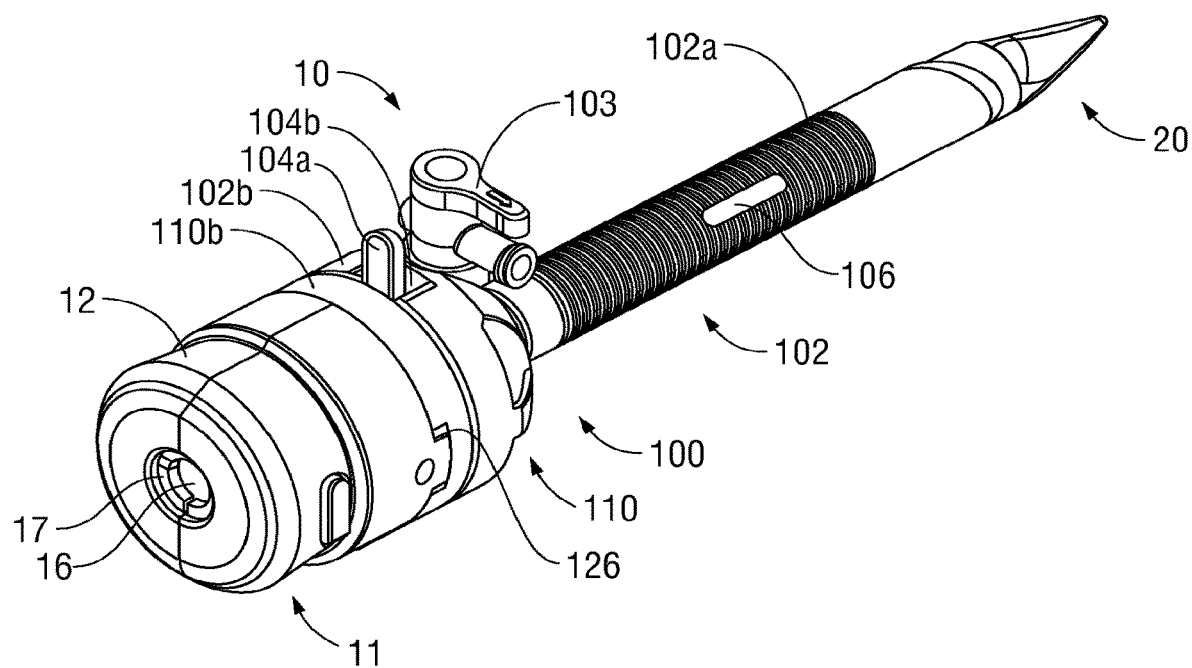
FIG. 1 is a perspective view of a surgical access assembly provided in accordance with the present disclosure.

As detailed below and illustrated in the figures, the present disclosure provides devices, systems, and methods that facilitate accessing an internal surgical site through an opening in tissue, performing one or more minimally-invasive surgical tasks within the internal surgical site, and closing the opening in tissue once the surgical task(s) is complete without the need to remove the cannula. In the accompanying figures and in the description that follows, in which like reference numerals identify similar or identical elements, the term "proximal" will refer to the end of the apparatus or portion thereof which is closest to the operator during use, while the term "distal" will refer to the end or portion which is farthest from the operator, as is traditional.

Turning now to FIGS. 1-4B, a surgical access assembly provided in accordance with the present disclosure is shown generally identified by reference numeral 10. Surgical access assembly 10 includes an obturator 11 and a cannula 100 that is configured to at least partially receive obturator 11, as detailed below. Cannula 100 is configured to provide a substantially fluid-tight seal between an internal surgical site within a patient and the outside atmosphere before, during, and after insertion of surgical instrumentation (not shown) through cannula 100 and into the internal surgical site.

Figure 2:
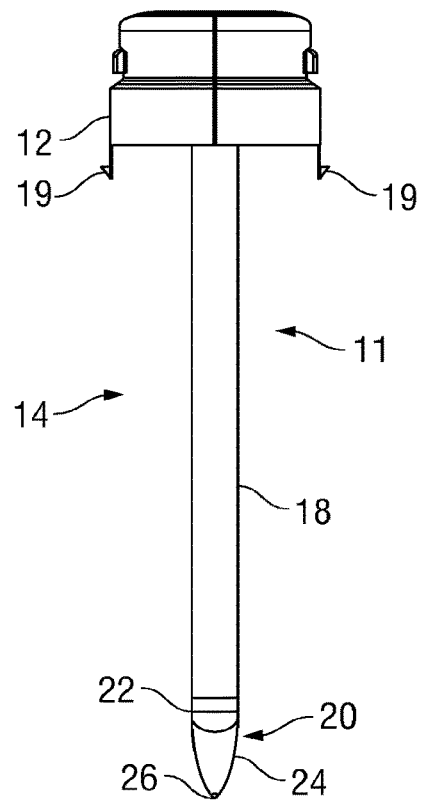
FIG. 2 is a side view of an obturator of the surgical access assembly of FIG. 1.
Figure 3:
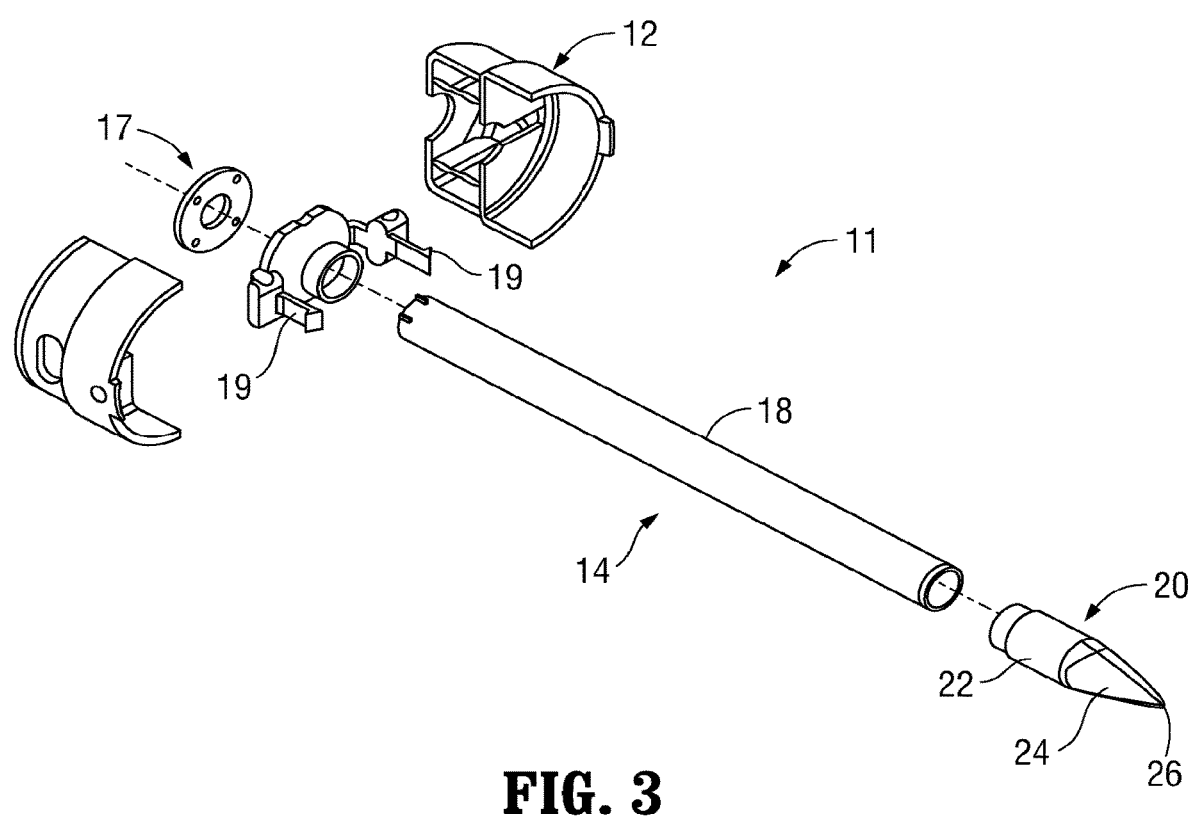
FIG. 3 is an exploded, perspective view of the obturator of FIG. 2.
Figure 4A:
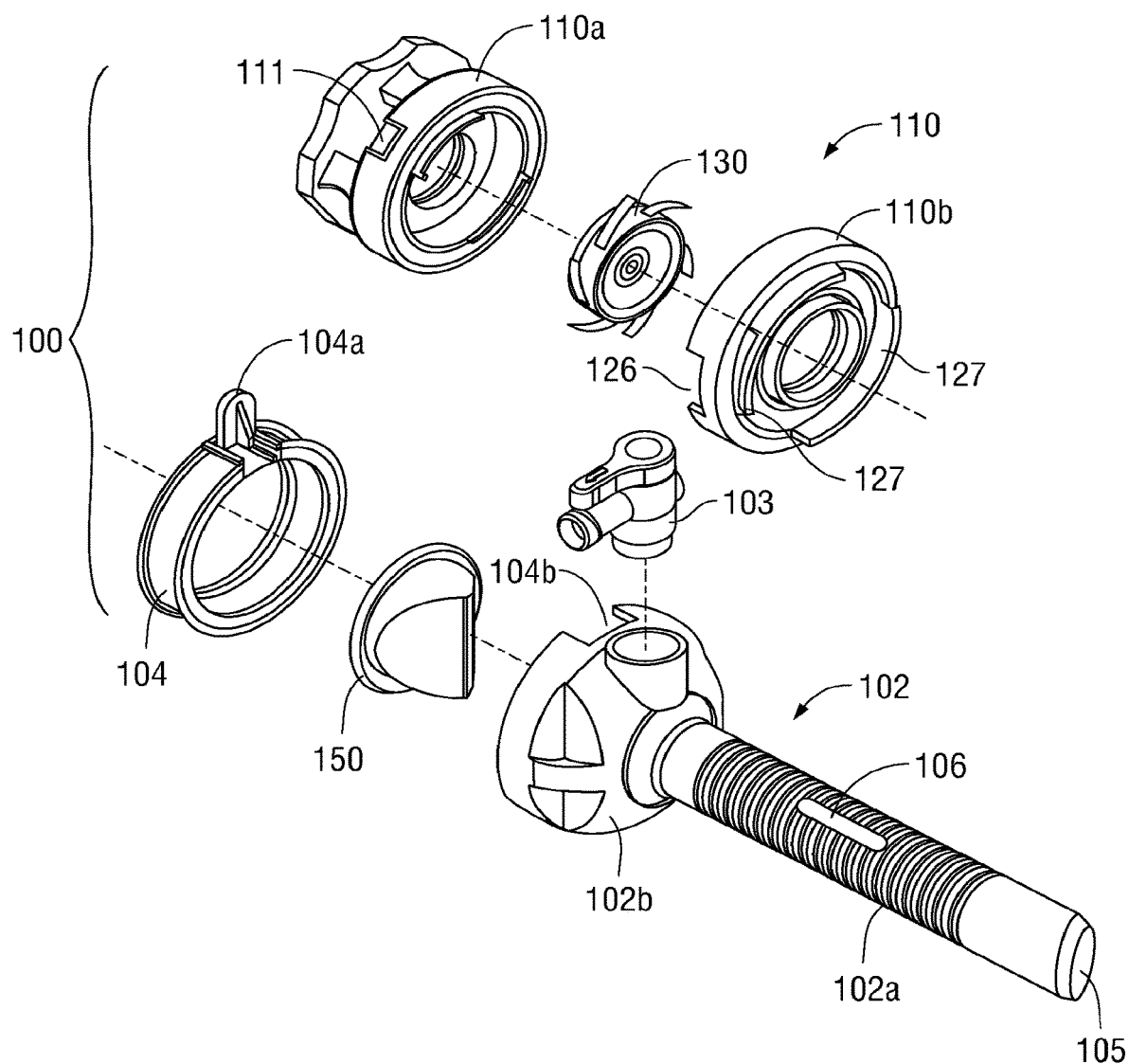
FIG. 4A is an exploded, perspective view of a cannula of the surgical access assembly of FIG. 1.
Figure 4B:
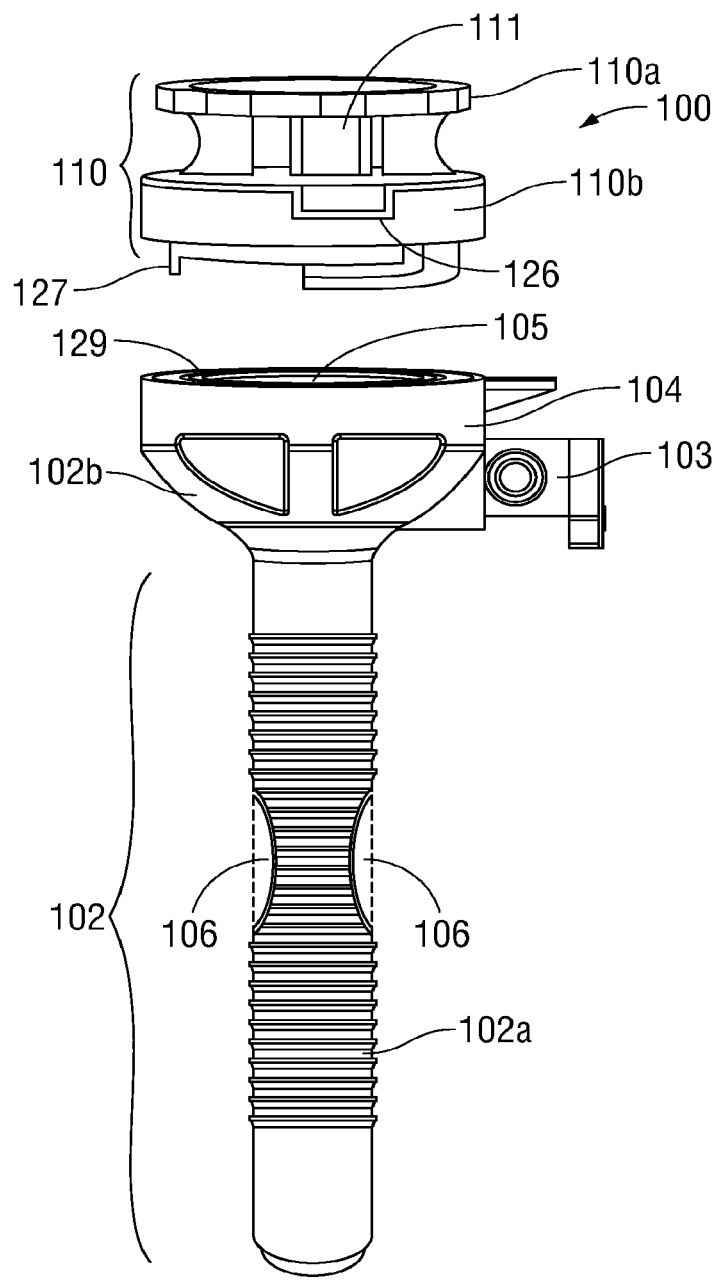
FIG. 4B is a perspective view of the cannula of FIG. 4A with the housing and elongated portion of the cannula shown separated from each other.

Referring to FIGS. 1-3, obturator 11 includes an obturator housing 12 disposed in mechanical cooperation with an elongated obturator member 14. Obturator housing 12 defines an opening 16 and includes a scope retention member 17 adjacent opening 16. Scope retention member 17 is fabricated from an elastomeric material and is configured to engage an outer surface of an endoscope (not shown) inserted therethrough in frictional engagement therewith to assist in retaining the relative positioning of the endoscope (not shown) within obturator 11.

Elongated obturator member 14 extends distally from obturator housing 12 and includes an obturator shaft 18 mechanically coupled to obturator housing 12, and an optical member 20 disposed at the distal end of obturator shaft 18. Obturator shaft 18 may be made from steel, a polymeric material, or any other suitable material. Optical member 20 defines a hollow interior and includes a proximal section 22, a central section 24, and an atraumatic guiding nub 26. Elongated obturator member 14 is configured for insertion through cannula 100 (FIG. 1) and defines a length greater than that of elongated tubular member 102a of cannula 100 such that optical member 20 of elongated obturator member 14 extends distally from elongated tubular member 102a of cannula 100 in a fully inserted position of obturator 11 relative to cannula 100 (see FIG. 1). Atraumatic guiding nub 26 of optical member 20 is configured to facilitate the initial insertion of obturator 11 and cannula 100 through an initial opening in tissue, e.g., a pre-cut scalpel incision, and the advancement thereof between tissue layers to gently enlarge tissue without cutting or incising tissue. After this initial insertion and with continued distal insertion, central section 24 and proximal portion 22 of optical member 20 continue to gently enlarge the opening in tissue to facilitate atraumatic passage of elongated obturator member 14 of obturator 11 and elongated tubular member 102a of cannula 100 through the opening in tissue. A distal viewing tip of the endoscope (not shown) is insertable through obturator shaft 18 and into the hollow interior of optical member 20 to facilitate visualization of tissue adjacent optical member 20 during insertion and advancement through tissue.

Referring to FIGS. 1 and 4A-5B, cannula 100 of surgical access assembly 10 includes an elongated portion 102 and a housing 110 including a proximal housing component 110a and a distal housing component 110b. Elongated portion 102 includes elongated tubular member 102a and a base member 102b. Base member 102b includes threading 129 configured to engage complementary threading 127 of distal housing component 110b, e.g., via a bayonet connection, to releasably engage housing 110 and elongated portion 102 to each other. Base member 102b further includes a valved insufflation port 103 allowing for the selective inflow and outflow of insufflation fluid. A collar 104 is configured to be seated within base member 102b to retain a zero-closure seal 150 within base member 102b. Zero-closure seal 150 maintains a substantially fluid-tight seal between the internal surgical site and the outside atmosphere in the absence of surgical instrumentation (not shown) inserted through cannula 100. Collar 104 further includes a tab 104a disposed within a recess 104b defined within base member 102b and selectively movable within recess 104b to unlock housing 110 from base member 102b, thus permitting disengagement of housing 110 from base member 102b. Elongated tubular member 102a extends distally from base member 102b and may be formed from a translucent material, although other configurations are also contemplated. Elongated tubular member 102a is described in detail below.

Proximal and distal housing components 110a, 110b, respectively, of housing 110 are selectively engagable with each other via snap-fit engagement or other suitable arrangement to form housing 110. Alternatively, these component may be integrally formed with each other. Proximal and distal housing components 110a, 110b cooperate to retain an insert seal assembly 130 therebetween. Insert seal assembly 130 is configured provide a substantially fluid-tight seal about the outer surface of surgical instrumentation (not shown) passing therethrough. Insert seal assembly 130 may further include a centering feature configured to bias insert seal assembly 130 and, thus, surgical instrumentation (not shown) passing therethrough, towards a radially centered position relative to housing 110. Proximal housing component 110a defines a pair of radially opposed apertures 111 extending therethrough, the importance of which will be detailed below. Distal housing component 110b includes a pair of notches 126 configured to mechanically engage a pair of corresponding latches 19 associated with obturator housing 12 (see FIGS. 2-3) to selectively lock and unlock obturator 11 to and from cannula 100. More specifically, obturator housing 12 is configured to receive proximal housing component 110a therein as elongated obturator member 14 (FIG. 2) is inserted into elongated tubular member 102a, ultimately such that latches 19 of obturator 11 are received within notches 126 of distal housing component 110b to lock obturator 11 and cannula 100 with each other. As noted above, housing 110 and elongated portion 102 are releasably engagable with each other, e.g., via engagement of threadings 127, 129, respectively. This releasable engagement facilitates the selective removal of housing 110 and, thus, insert seal assembly 130, from cannula 100 such that cannula assembly 100 may be utilized without insert seal assembly 130, and also ensures proper alignment of housing 110 with respect to elongated portion 102 upon engagement therebetween, the importance of which will be detailed below.

Figure 5A:
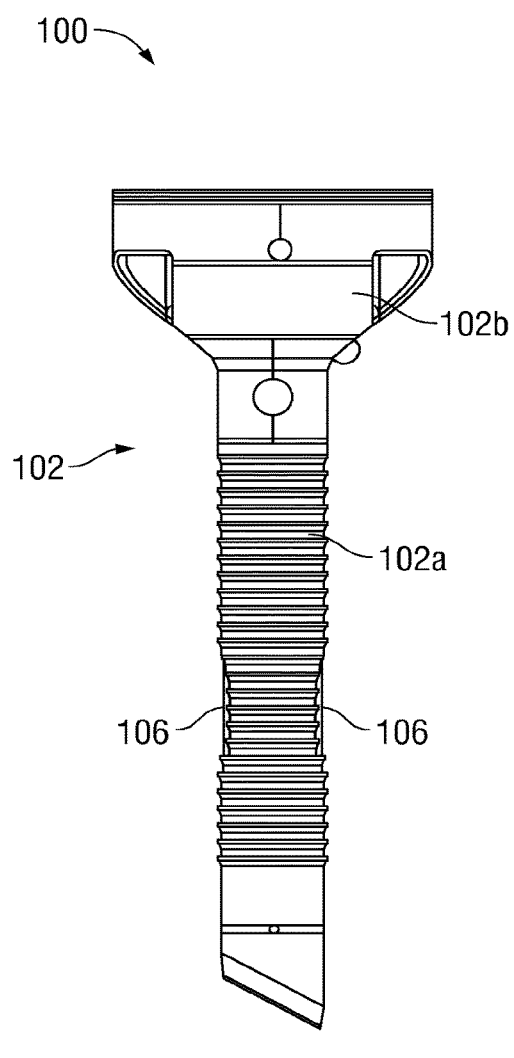
FIG. 5A is a first side view of the cannula of FIG. 4A with the housing removed.
Figure 5B:
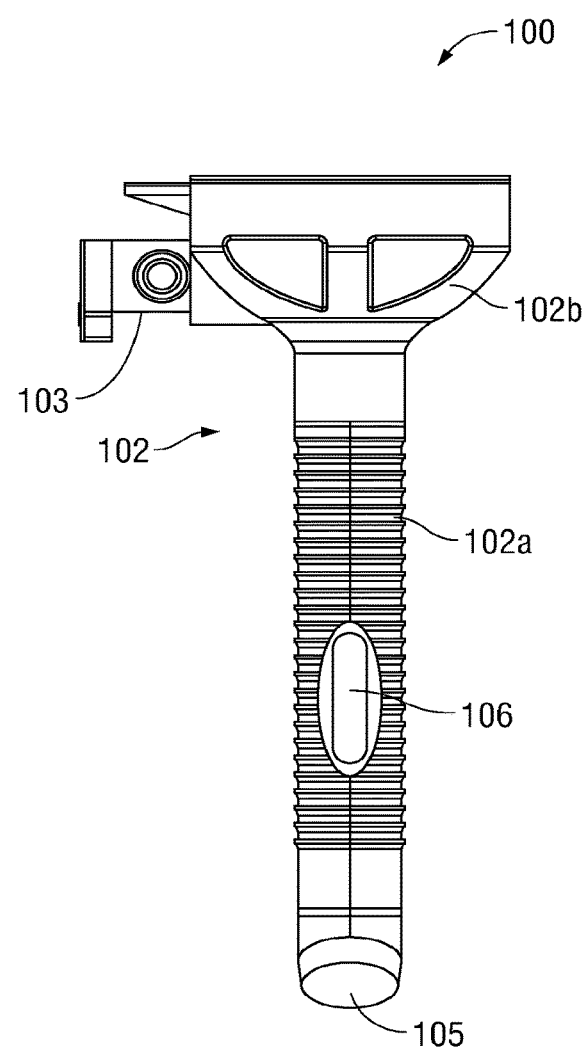
FIG. 5B is a second side view rotated 90 degrees of the cannula of FIG. 4A with the housing removed.

With reference in particular to FIGS. 5A-5B, elongated tubular member 102a of cannula 100 may be provided in various different configurations, e.g., various diameters between about 10 mm to about 15 mm and/or various lengths from about 70 mm to about 150 mm, although other suitable configurations are also contemplated. Elongated tubular member 102a may define a ribbed exterior (as shown) or may define a generally smooth exterior, depending on a particular purpose. Elongated tubular member 102a is configured for positioning within an opening in tissue and defines a longitudinal passageway 105 extending therethrough that is configured to receive surgical instrumentation (not shown) for guiding the surgical instrumentation (not shown) through the opening in tissue and into the internal surgical site. Passageway 105 of elongated tubular member 102a is further configured to receive elongated obturator member 14 of obturator 11 (see FIG. 1) to facilitate insertion of elongated tubular member 102a into the opening in tissue, as detailed above, and is also configured to receive one or more guide members 300, 400, 500, and 600 (FIGS. 7, 9, 11, and 13, respectively), to facilitate closure of the opening in tissue after completion of the surgical procedure, as detailed below.

A pair of opposed slots 106 extend through the annular side wall of elongated tubular member 102a, thus providing lateral access to and from longitudinal passageway 105 to and from the exterior of elongated tubular member 102a. Opposed slots 106 may be positioned along the length of elongated tubular member 102a at any suitable position, e.g., closer to or further from base 102b member of elongated portion 102 of cannula 100. Thus, a cannula 100 including a particular positioning of slots 106 may be selected based upon on the procedure being performed, the location of the opening in tissue, the patient's anatomy, the user's preference, and/or other factors. For some procedures, it has been found to be desirable that, once cannula 100 is positioned within the opening in tissue, slots 106 are positioned distally of the skin and fatty layers of tissue and adjacent to the fascia and muscle layers of tissue since fascia and muscle layers are better suited to receive and retain a suture for closing the opening in tissue. Thus, a cannula 100 having slots 106 positioned to achieve this configuration may be selected. However, other configurations are also contemplated. Further, as an alternative or in addition to providing multiple cannulas 100 having differently positioned slots 106, multiple pairs of opposed slots 106 may be spaced-apart along the length of elongated tubular member 102a such that an appropriately positioned pair of slots 106 may be utilized, e.g., depending on the procedure being performed, the location of the opening in tissue, the patient's anatomy, the user's preference, and/or other factors.

Referring momentarily to FIGS. 25-28, elongated tubular member 102a may further include a sealing feature, e.g., sealing member 107 (FIG. 25), sealing member 108 (FIG. 26), sealing member 109 (FIG. 27), or sealing member 160 (FIG. 28), sealingly disposed about each of slots 106 and configured to maintain a fluid-tight seal about elongated tubular member 102a to inhibit fluid exchange between longitudinal passageway 105 (FIG. 5B) and the exterior of elongated tubular member 102a via slots 106. As can be appreciated, such a configuration allows for the maintenance of an insufflated internal surgical site during the course of a surgical procedure. As detailed below, once maintaining insufflation is no longer necessary and/or where access through slots 106 is needed, e.g., after the surgical procedure has been completed, the respective sealing members 107, 108, 109, 160 (FIGS. 25-28, respectively) may be penetrated to facilitate closure of the opening in tissue. Each of the respective sealing members 107, 108, 109, 160 (FIGS. 25-28) is detailed, in turn, below.

Figure 25:
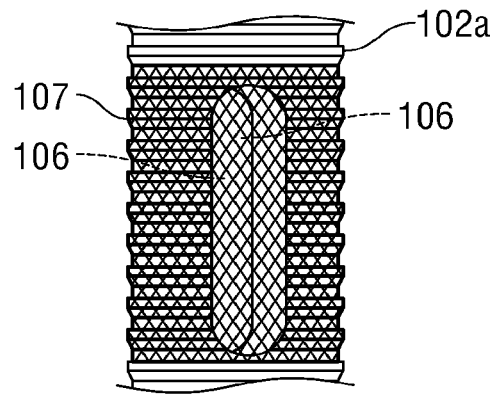
FIG. 25 is a side view of a portion of an elongated member of the cannula of FIG. 4A including a sealing member disposed thereabout.

As shown in FIG. 25, sealing member 107 is formed as a sleeve disposed about a portion of elongated tubular member 102a and is positioned so as to cover slots 106. Sealing member 107 may be formed from any suitable flexible, penetrable material, e.g., rubber, PVC, etc., and may be disposed about elongated tubular member 102a via heat shrink wrapping, overmolding, or any other suitable process. As shown in FIG. 25, sealing member 107 substantially conforms to the exterior configuration of elongated tubular member 102a so as to maintain the ribbed configuration of the exterior of elongated tubular member 102a.

Figure 26:
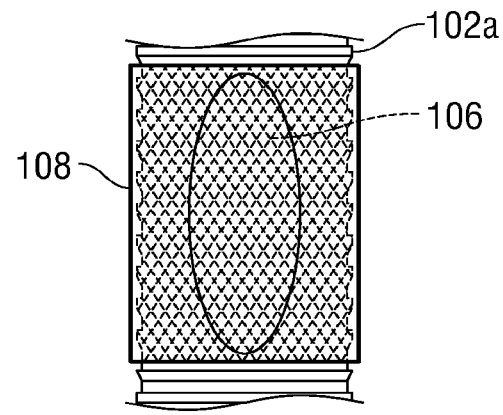
FIG. 26 is a side view of the portion of the elongated member of the cannula of FIG. 4A including another sealing member disposed thereabout.

Referring to FIG. 26, sealing member 108 is similar to sealing member 107 (FIG. 25) except that sealing member 108 is disposed about elongated tubular member 102a so as to define a substantially smooth exterior surface, e.g., without ribs. Sealing member 108 may be formed from similar materials and/or may be disposed about elongated tubular member 102a similarly as detailed above with respect to sealing member 107 (FIG. 25).

Figure 27:
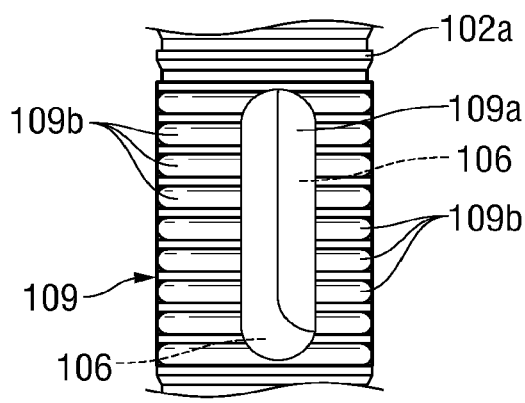
FIG. 27 is a side view of the portion of the elongated member of the cannula of FIG. 4A including yet another sealing member disposed thereabout.

With reference to FIG. 27, sealing member 109 is similar to sealing member 107 (FIG. 25) except that, rather than defining a sleeve disposed about elongated tubular member 102a, sealing member 109 includes a seal member 109a sealingly disposed over each of slots 106 and a plurality of spaced-apart bands 109b disposed about elongated tubular member 102a so as to maintain seal members 109a in position about slots 106. Bands 109b are disposed between the ribs defined on the exterior surface of elongated tubular member 102a so as to maintain the ribbed configuration of elongated tubular member 102a. Sealing member 109 may be formed from similar materials and/or may be disposed about elongated tubular member 102a similarly as detailed above with respect to sealing member 107 (FIG. 25). In some embodiments, bands 109b are positioned such that seal members 109a function as flaps, rather than being configured to be penetrated by a suture passer. In such embodiments, bands 109b bias seal members 109a against elongated tubular member 102a so as to maintain a seal about slots 106 in the absence of a suture passer. Upon insertion of a suture passer through one of the slots 106, the corresponding seal member 109a is deflected to permit passage of the suture passer therethrough. Upon withdrawal of the suture passer, the seal member 109a is returned to its biased position, once again sealing the slot 106.

Figure 28:
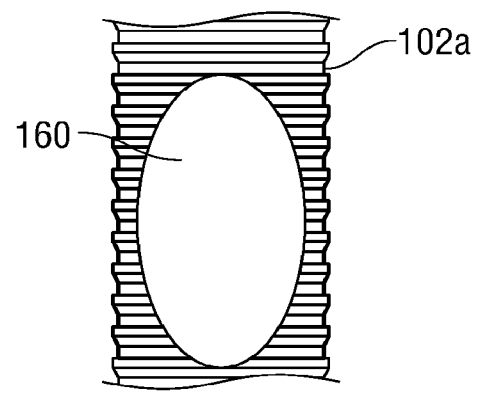
FIG. 28 is a side view of the portion of the elongated member of the cannula of FIG. 4A including another sealing member disposed about one of the slots defined therethrough.

As shown in FIG. 28, sealing member 160 is shown disposed about one of the slots 106 (FIGS. 5A-5B) defined through elongated tubular member 102a. Although only one of sealing members 160 is shown, it is envisioned that a sealing member 160 be provided for sealing each of the slots 106 (FIGS. 5A-5B) defined through elongated tubular member 102a. Rather than being annularly disposed about elongated tubular member 102a, each sealing member 160 is localized about one of the slots 106 (FIGS. 5A-5B), and is sealingly disposed thereabout via overmolding or other suitable process. Sealing members 160 may be formed from any suitable flexible, penetrable material for this purpose, e.g., any of the materials noted above.

Figure 6A:
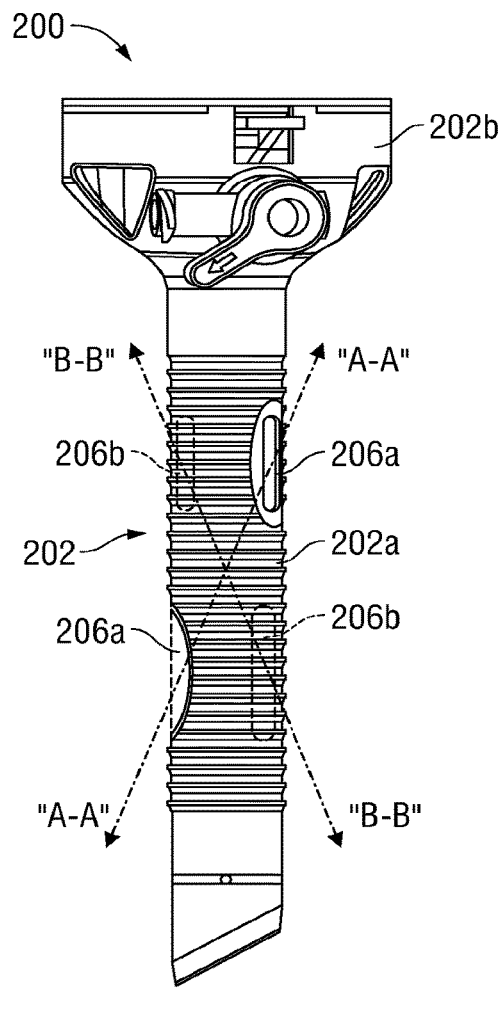
FIG. 6A is a first side view of another cannula provided in accordance with the present disclosure with the housing removed.
Figure 6B:
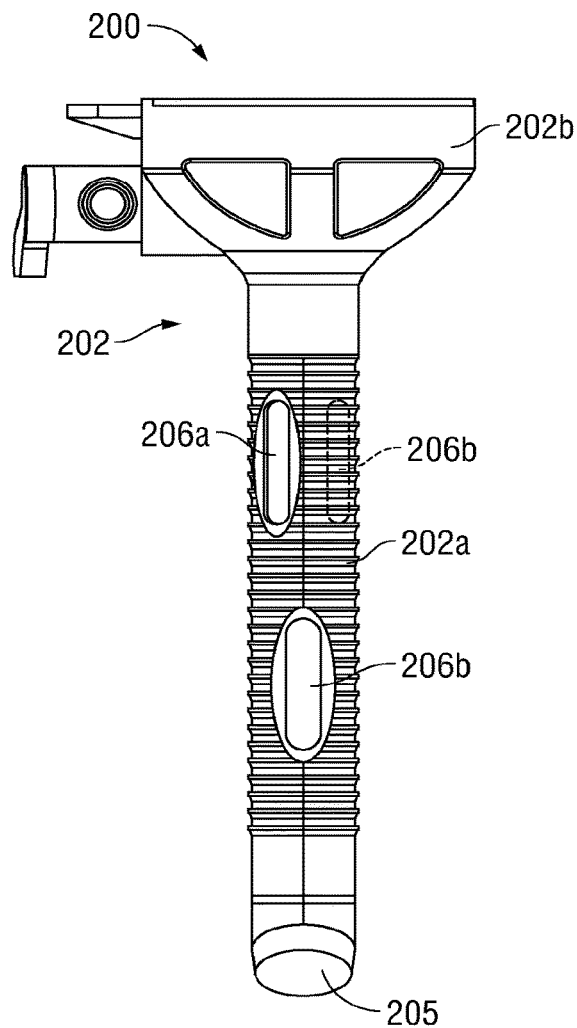
FIG. 6B is a second side view rotated 90 degrees of the cannula of FIG. 6A with the housing removed.

Referring to FIGS. 6A-6B, another embodiment of a cannula configured for use with surgical access assembly 10 (FIG. 1) is shown generally as cannula 200. Cannula 200 includes a housing having proximal and distal components (not shown, similar to housing 110 of cannula 100 (FIGS. 4A-4B)), and an elongated portion 202 extending distally from the housing (not shown). Elongated portion 202 includes a base member 202b configured to releasably receive the housing (not shown) and an elongated tubular member 202a extending distally from base member 202b. Cannula 200 is similar to cannula 100 (FIGS. 4A-5B) and, thus, only the differences between cannula 200 and cannula 100 (FIGS. 4A-5B) will be described in detail below for purposes of brevity.

Elongated tubular member 202a of cannula 200 defines a longitudinal passageway 205 extending therethrough and two pairs of offset slots 206a, 206b extending through the annular side wall of elongated tubular member 202a, thus providing lateral access to and from longitudinal passageway 205 to and from the exterior of elongated tubular member 202a. Each pair of slots 206a, 206b includes a more-proximally disposed slot and a more-distally disposed slot. The proximal and distal slots of each pair of slots 206a, 206b are diagonally offset from one another. More specifically, the proximal and distal slots of the first pair of slots 206a define a first slot axis "A-A" disposed at an oblique angle relative to the longitudinal axis of cannula 200, while the proximal and distal slots of the second pair of slots 206b define a second, different slot axis "B-B" that is also disposed at an oblique angle relative to the longitudinal axis of cannula 200, although these oblique angles need not be the same. The pairs of slots 206a, 206b may be positioned along the length of elongated tubular member 202a in various different positions and/or multiple sets of paired slots 206a, 206b may be provided, similarly as detailed above with respect to cannula 100 (FIGS. 5A-5B). Elongated tubular member 202a may further include one or more penetrable sealing features, e.g., any of sealing members 107, 108, 109, 160 (FIGS. 25-28, respectively), disposed about slots 206a, 206b and/or elongated tubular member 202a and configured to seal slots 206a, 206b.

Detailed below with respect to FIGS. 7-14B are various embodiments of guide members configured for use with surgical access assembly 10 (FIG. 1) to facilitate closure of an opening in tissue after completion of one or more surgical tasks. More specifically, each of the guide members 300, 400, 500, 600 is configured for releasable engagement within cannula 100 (FIGS. 5A-5B) and/or cannula 200

(FIGS. 6A-6B) to guide passage of a suitable suture passer, e.g., suture passers 700, 800, 900 (see FIGS. 15-22B), through tissue and into the internal surgical site to deposit and/or retrieve a portion of a suture, thus facilitating closing the opening in tissue. Each guide member 300, 400, 500, 600 will be described in turn below. As can be appreciated, any or all of guide members 300, 400, 500, 600 may be provided for use in conjunction with either or both cannulas 100 and 200 (FIGS. 5A-5B and 6A-6B, respectively), any of the other components of surgical access assembly 10 (FIG. 1), and/or any of the suture passers 700, 800, 900 (see FIGS. 15-22B) detailed below as part of a system or kit that facilitates accessing an internal surgical site through an opening in tissue, performing one or more minimally-invasive surgical tasks within the internal surgical site, and closing the opening in tissue once the surgical task(s) is complete. As an alternative to a suture passer, needles, wires, or other suitable instrument may also be used with respect to any of the embodiments detailed herein for similar or different purposes.

Figure 7:
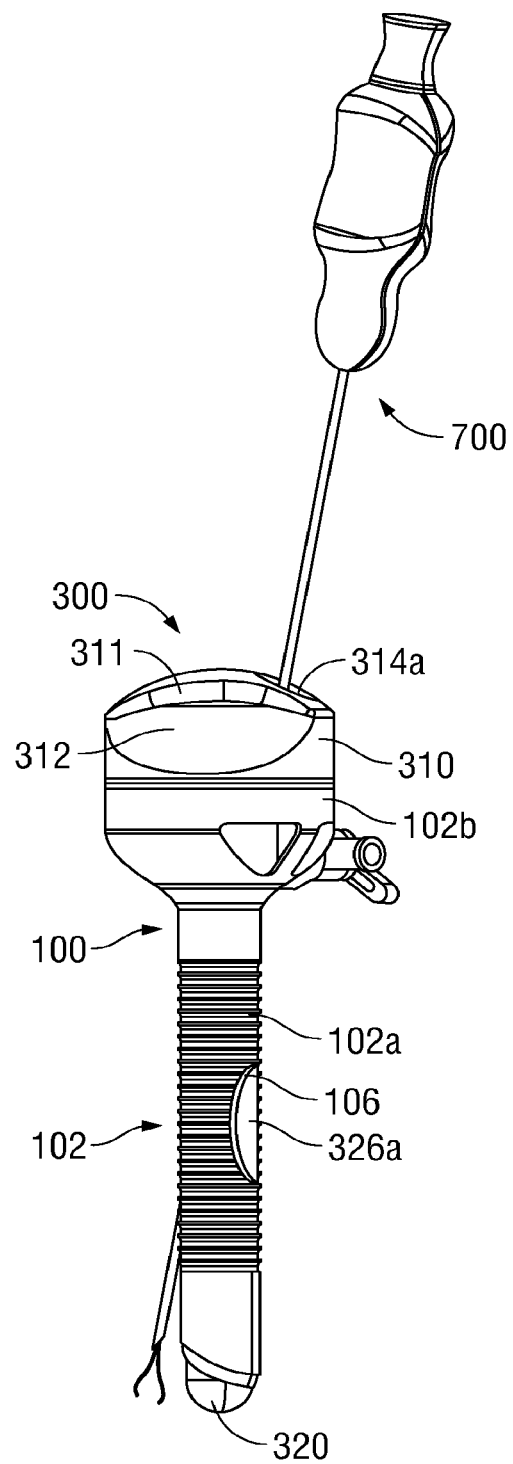
FIG. 7 is a side view of the cannula of FIG. 4A with the housing removed, a guide member engaged with the cannula, and a suture passer inserted through the guide member and cannula.
Figure 8A:
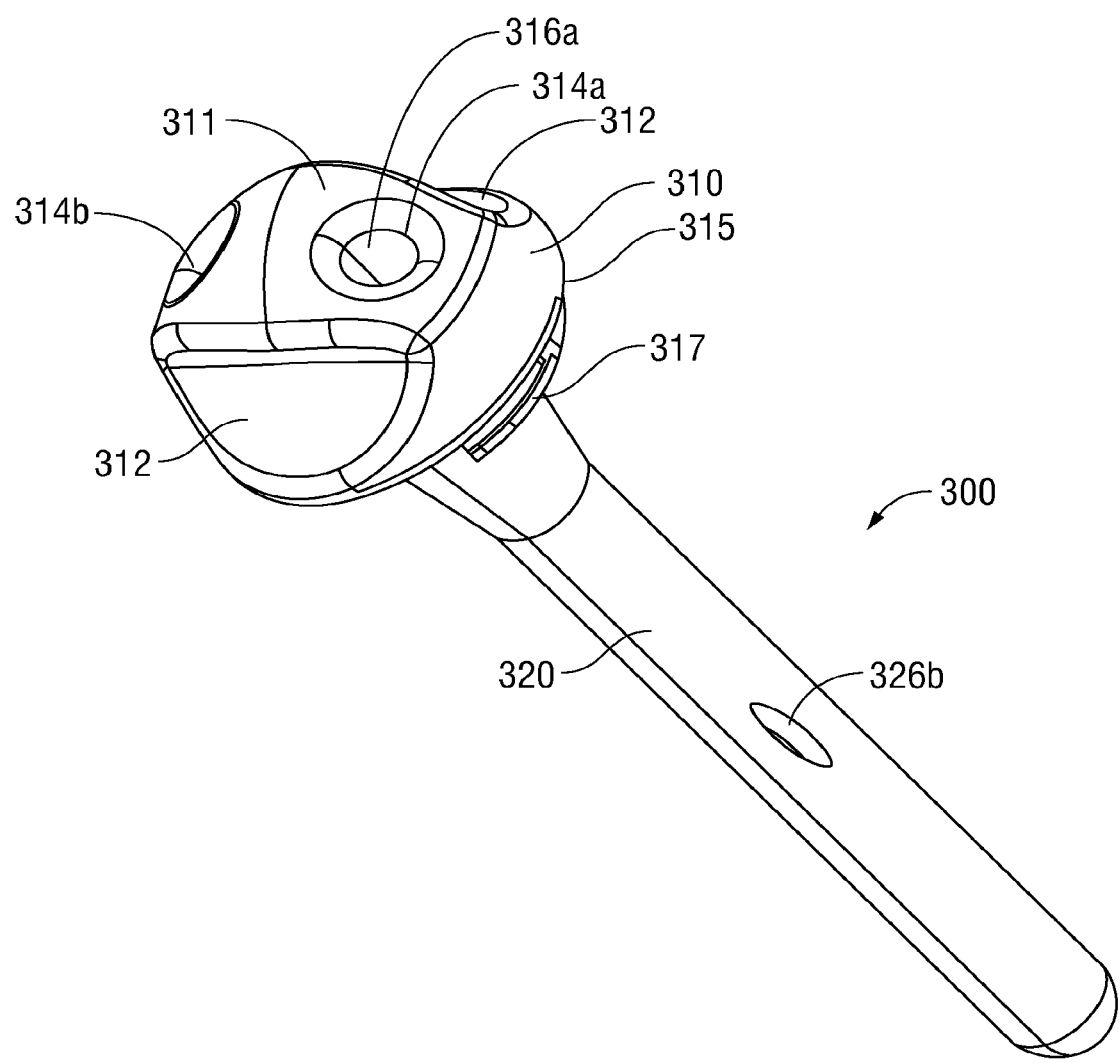
FIG. 8A is a first perspective view of the guide member of FIG. 7.
Figure 8B:
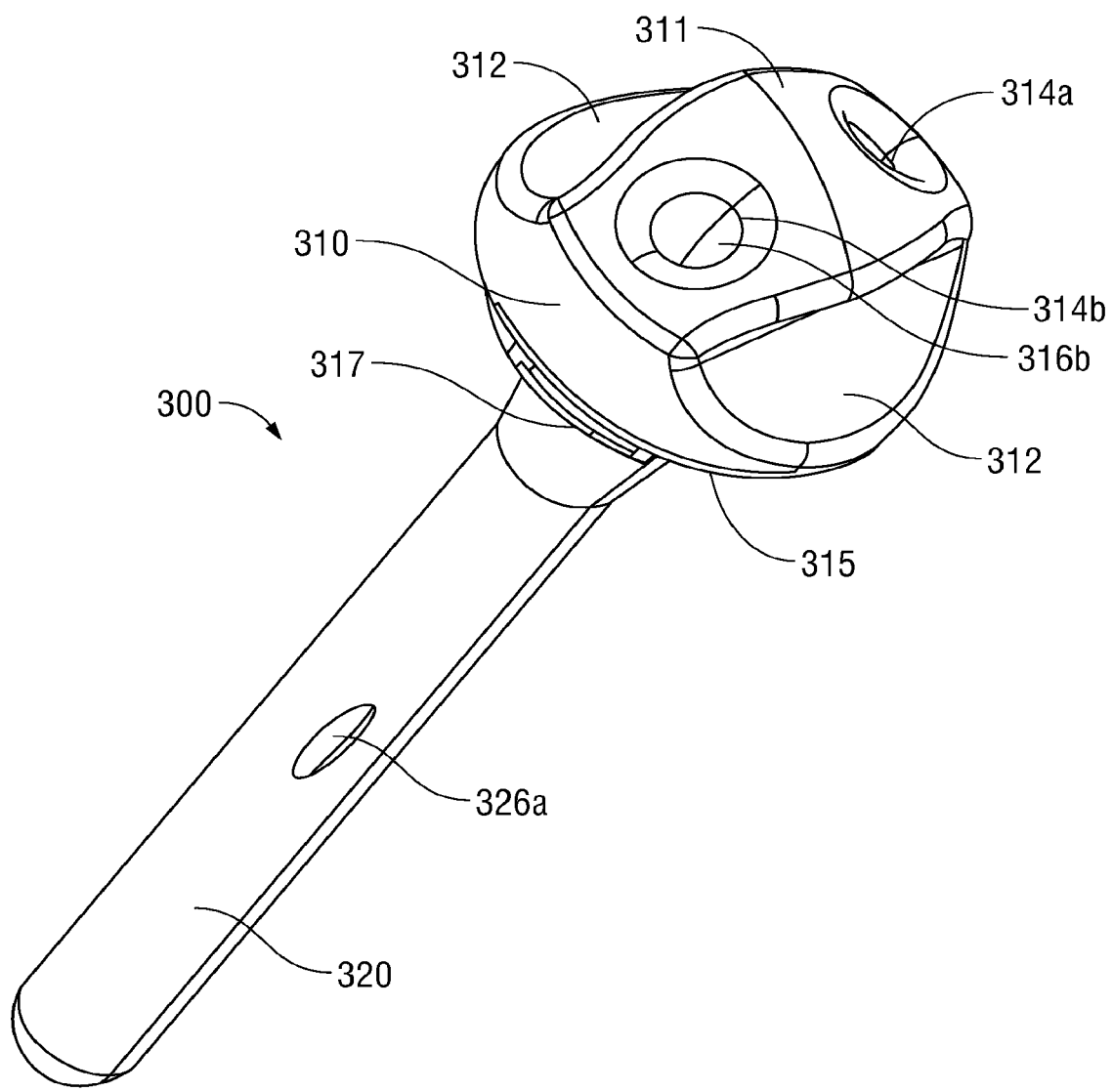
FIG. 8B is a second perspective view of the guide member of FIG. 7.

Turning to FIGS. 7-8B, one embodiment of a guide member configured for use with cannula 100 and a suture passer, e.g., suture passer 700 or any other suitable suture passer, for closing an opening in tissue is shown generally identified by reference numeral 300. Guide member 300 generally includes a guide housing 310 disposed in mechanical cooperation with an elongated guide shaft 320. Guide member 300 further includes a pair of guide lumens 316a, 316b extending therethrough.

Guide housing 310 defines a proximally-facing portion 311 including a pair of recesses 312 that facilitate grasping and manipulation of guide member 300 and a pair of apertures 314a, 314b that communicate with the proximal ends of respective lumens 316a, 316b extending through guide member 300. Guide housing 310 further includes threading 317 defined on a distally-facing portion 315 thereof that is configured to engage complementary threading 129 of base member 102b of cannula 100 (see FIG. 4B), e.g., via a bayonet connection, to releasably engage and align guide housing 310 and elongated portion 102 of cannula 100 relative to one another, as detailed below.

Elongated guide shaft 320 of guide member 300 extends distally from guide housing 310 and is configured for insertion through passageway 105 (FIG. 5B) of elongated tubular member 102a of cannula 100. Elongated shaft 320 includes a pair of opposed slots 326a, 326b defined through the annular side wall of elongated shaft 320 that communicate with the distal ends of respective lumens 316a, 316b extending through guide member 300. That is, lumens 316a, 316b extend between respective apertures 314a, 314b defined through proximally-facing portion 311 of guide housing 310 and respective slots 326a, 326b defined through guide shaft 320. Each lumen 316a, 316b is curved to define a radius of curvature, and interconnects a respective aperture 314a, 314b with a respective slot 326a, 326b disposed on an opposite side of guide member 300 (see, e.g., suture passer 700 in FIG. 7). As such, a suture passer having a flexible shaft and/or a suture passer having a corresponding radius of curvature may be used in conjunction with guide member 300. Further, lumens 316a, 316b are radially staggered relative to one another such that, despite the fact that lumens 316a, 316b cross over one another, lumens 316a, 316b do not intersect one another.

Continuing with reference to FIGS. 7-8B, when using guide member 300 with cannula 100, housing 110 of cannula 100 is first disengaged from base member 102b and removed. Thereafter, guide member 300 is inserted into cannula 100 such that guide shaft 320 is advanced into elongated tubular member 102a and guide housing 310 is approximated relative to base member 102b. Upon sufficient insertion, guide member 300 may be rotated relative to cannula 100 to engage threading 317 of guide member 300 with complementary threading 129 of base member 102b (see FIG. 4B) to both secure guide member 300 in position relative to cannula 100 and to align guide member 300 relative to cannula 100. Grasping and rotating guide housing 310 to achieve this threaded engagement is facilitated by recesses 312, as noted above. With guide member 300 and cannula 100 properly aligned relative to one another, each slot 326a, 326b of guide shaft 320 is aligned with one of the slots 106 defined through elongated tubular member 102a of cannula 100. As such, and as will be detailed below, a suture passer, e.g., suture passer 700 or any other suitable suture passer, may then be inserted through one of lumens 316a, 316b of guide member 300, the corresponding slot 106 of cannula 100 (penetrating the sealing member disposed thereabout), tissue, and into the internal surgical site to facilitate closure of the opening in tissue.

Figure 9:
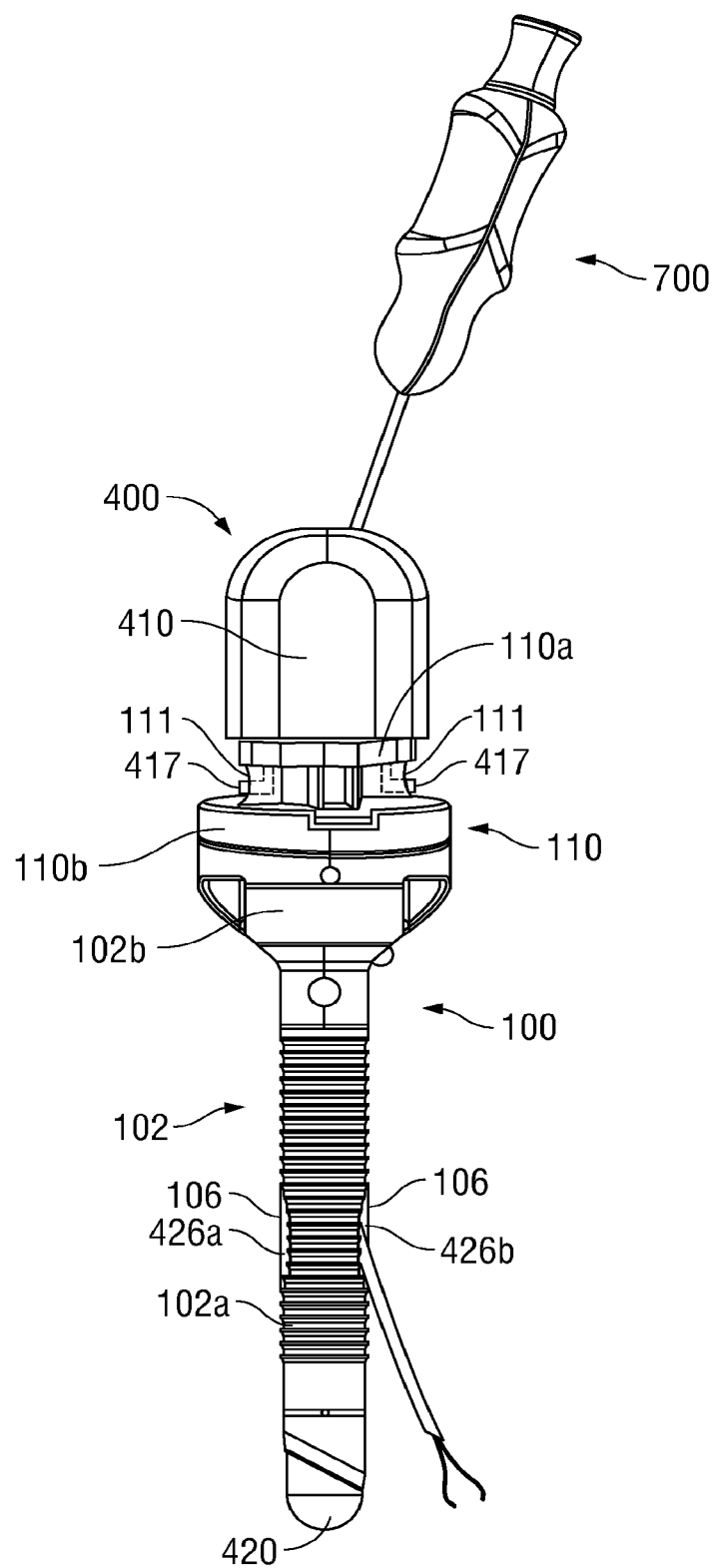
FIG. 9 is a side view of the cannula of FIG. 4A with the housing removed, another guide member engaged with the cannula, and the suture passer of FIG. 7 inserted through the guide member and cannula.
Figure 10A:
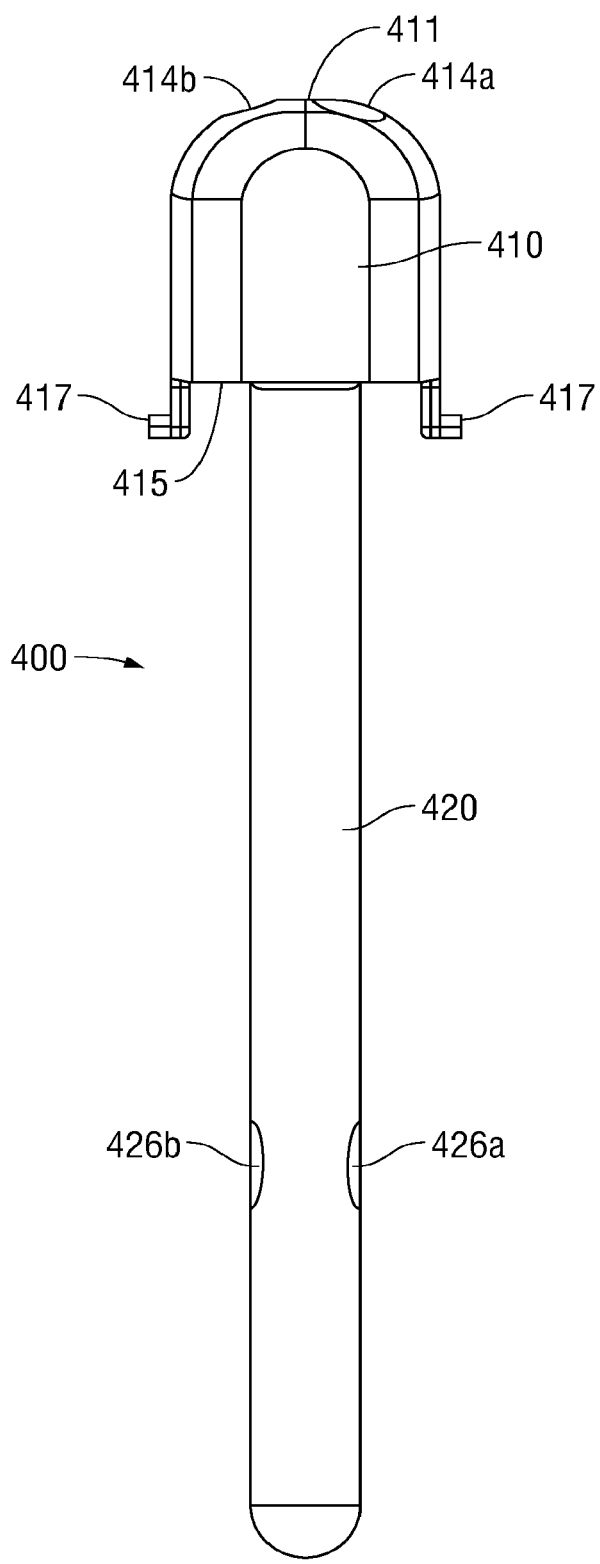
FIG. 10A is a side view of the guide member of FIG. 9.
Figure 10B:
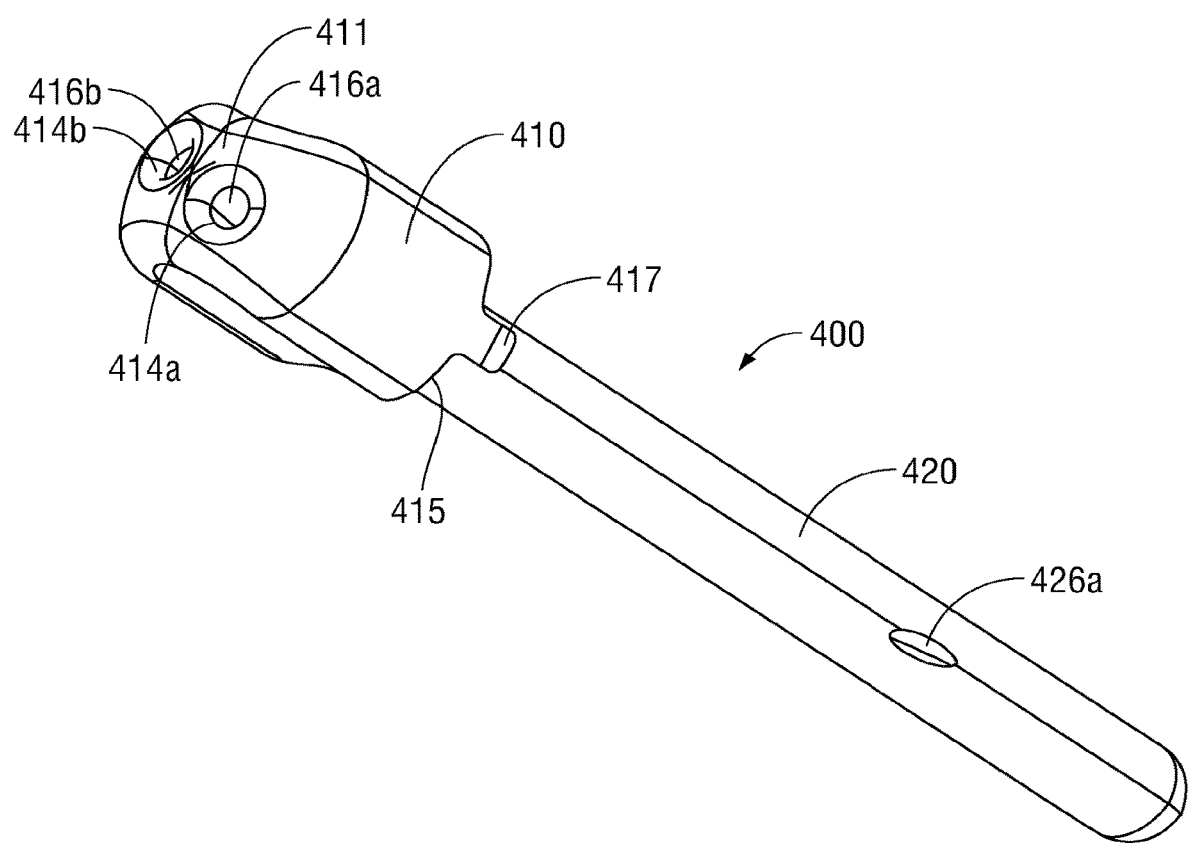
FIG. 10B is a first perspective view of the guide member of FIG. 9.
Figure 10C:
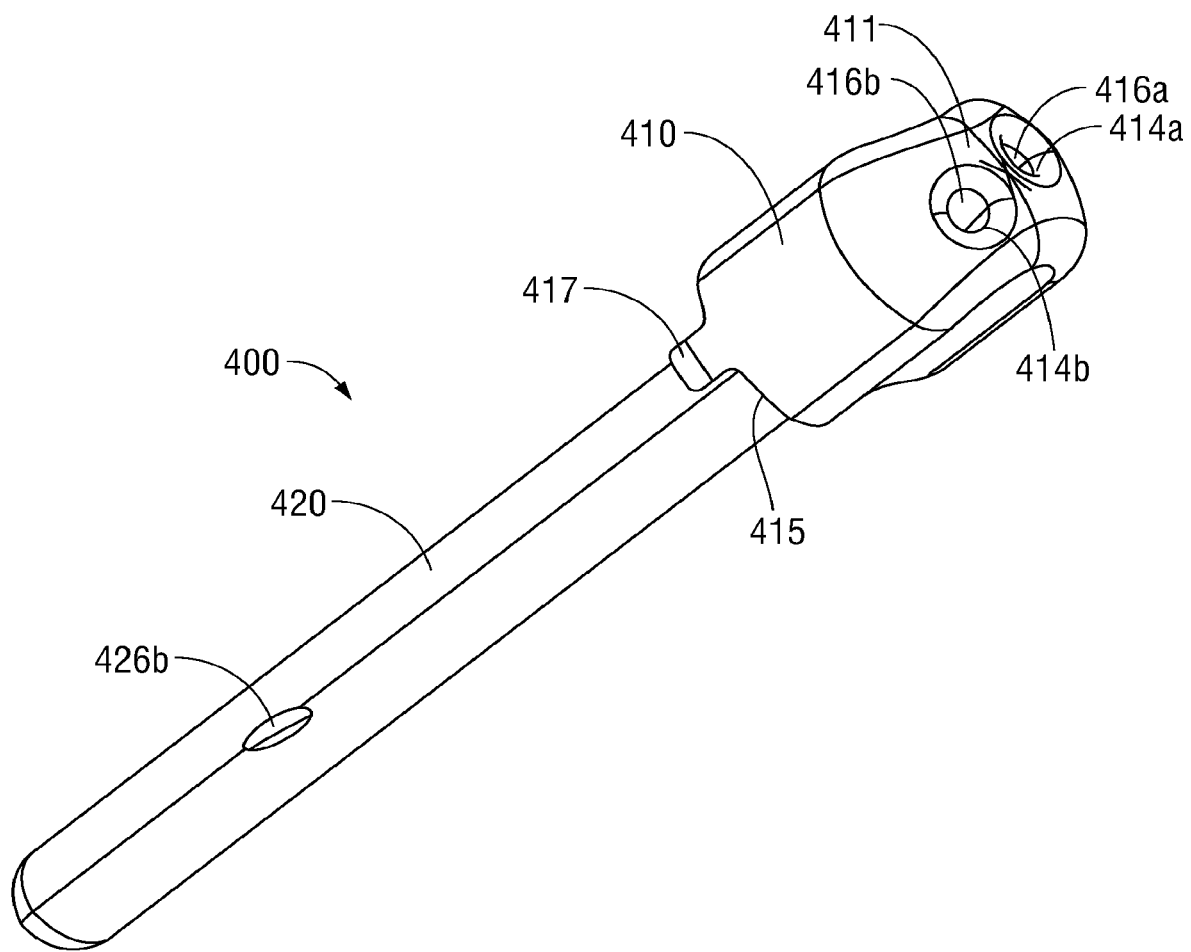
FIG. 10C is a second perspective view of the guide member of FIG. 9.

Turning to FIGS. 9-10C, another embodiment of a guide member configured for use with cannula 100 and a suture passer, e.g., suture passer 700 or any other suitable suture passer, for closing an opening in tissue is shown generally identified by reference numeral 400. Guide member 400 generally includes a guide housing 410 disposed in mechanical cooperation with an elongated guide shaft 420. Guide member 400 further includes a pair of guide lumens 416a, 416b extending therethrough.

Guide housing 410 defines a proximally-facing portion 411 including a pair of apertures 414a, 414b that communicate with the proximal ends of respective lumens 416a, 416b extending through guide member 400. Guide housing 410 further includes a pair of engagement tabs 417 disposed on opposite sides of guide housing 410 and extending distally from a distally-facing portion 415 of guide housing 410. Engagement tabs 417 are configured for releasable engagement within the radially opposed apertures 111 defined though proximal housing component 110a of housing 110 of cannula 100 (see FIGS. 4A-4B) to permit releasable engagement and alignment of guide member 400 with cannula 100, as detailed below.

Elongated guide shaft 420 of guide member 400 extends distally from guide housing 410 and is configured for insertion through passageway 105 (FIG. 5B) of elongated tubular member 102a of cannula 100. Elongated shaft 420 includes a pair of opposed slots 426a, 426b defined through the annular side wall of elongated shaft 420 that communicate with the distal ends of respective lumens 416a, 416b extending through guide member 400. Lumens 416a, 416b of guide member 400 define a radius of curvature that is smaller than that of lumens 316a, 316b of guide member 300 (see FIGS. 7-8B). This smaller radius of curvature is enabled by the fact that, different from guide member 300 (FIGS. 7-8B), each lumen 416a, 416b interconnects a respective aperture 414a, 414b with a respective slot 426a, 426b disposed on the same side of guide member 400 (see, e.g., suture passer 700 in FIG. 9). Accordingly, lumens 416a, 416b do not intersect one another. Similarly as detailed above with respect to guide member 300 (FIGS. 7-8B), a suture passer having a flexible shaft and/or a suture passer having a corresponding radius of curvature may be used in conjunction with guide member 400.

Continuing with reference to FIGS. 9-10C, when using guide member 400 with cannula 100, guide member 400 is inserted into cannula 100 (with housing 110 engaged to base member 102b) such that guide shaft 420 is advanced into elongated tubular member 102a and guide housing 410 is approximated relative to housing 110. Upon sufficient insertion, and with proper alignment between guide member 400 and cannula 100, engagement tabs 417 of guide housing 410 are releasably engaged within apertures 111 of proximal housing component 110a of housing 110 of cannula 100 to both secure guide member 400 in position relative to cannula 100 and to ensure and maintain alignment of guide member 400 relative to cannula 100. With guide member 400 and cannula 100 properly aligned relative to one another, each slot 426a, 426b of guide shaft 420 is aligned with one of the slots 106 defined through elongated tubular member 102a of cannula 100. As such, a suture passer, e.g., suture passer 700 or any other suitable suture passer, may be inserted through one of lumens 416a, 416b of guide member 400, the corresponding slot 106 of cannula 100 (penetrating the sealing member disposed thereabout), tissue, and into the internal surgical site to facilitate closure of the opening in tissue.

Figure 11:
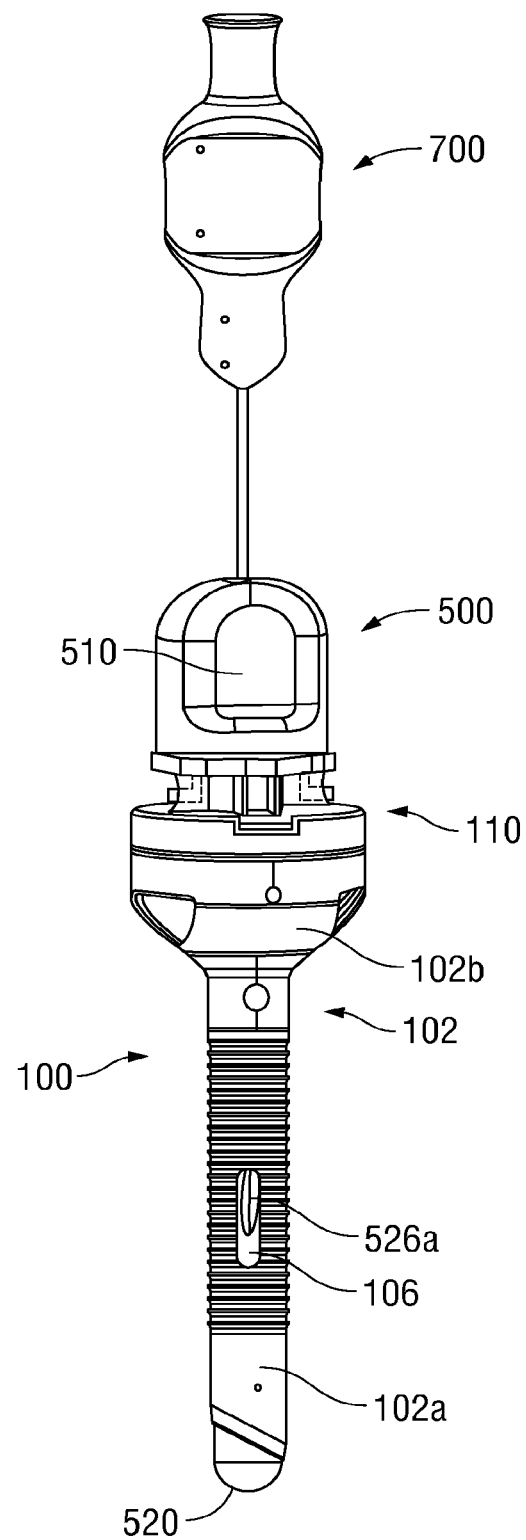
FIG. 11 is a side view of the cannula of FIG. 4A including another guide member engaged with the cannula and the suture passer of FIG. 7 inserted through the guide member and cannula.
Figure 12A:
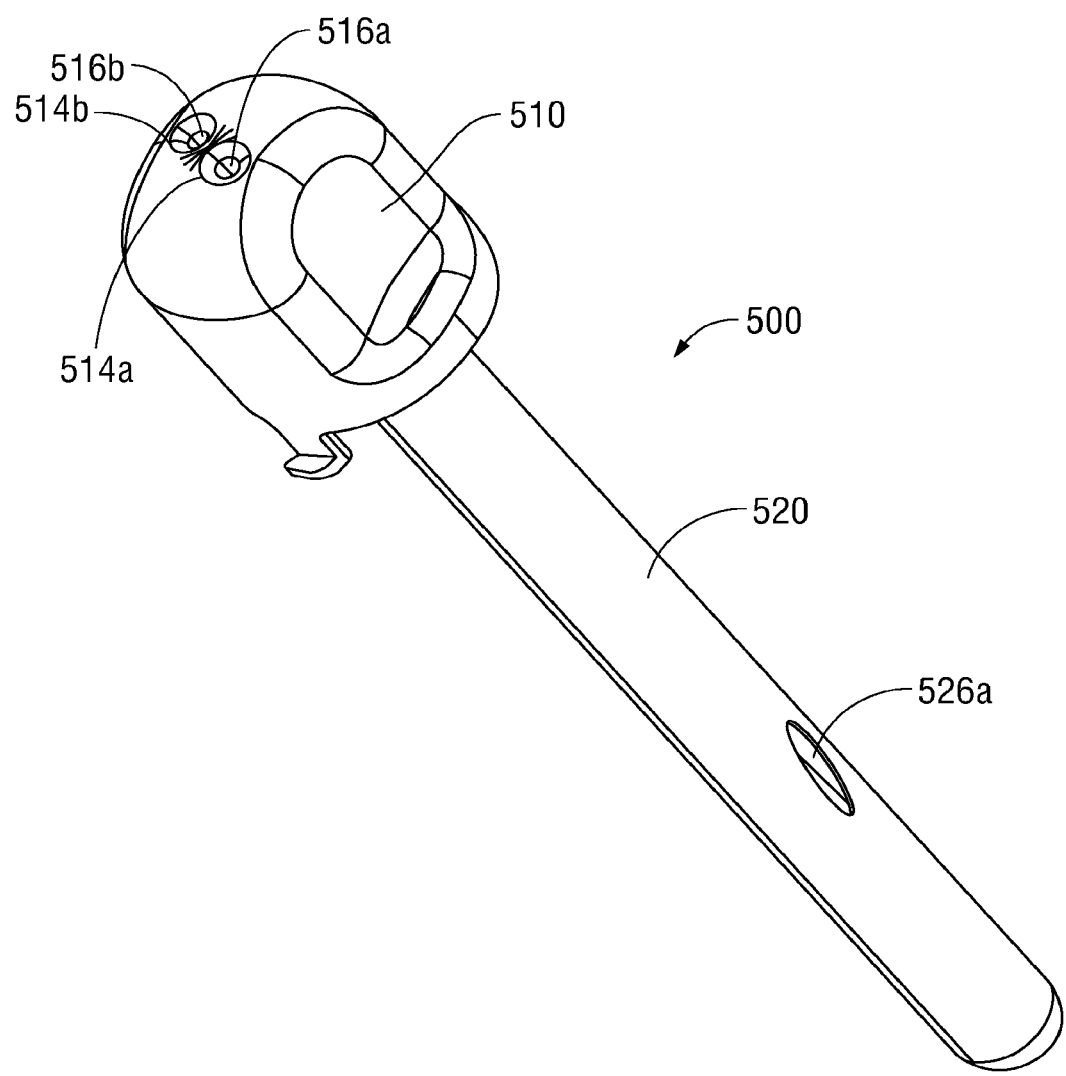
FIG. 12A is a first perspective view of the guide member of FIG. 11.
Figure 12B:
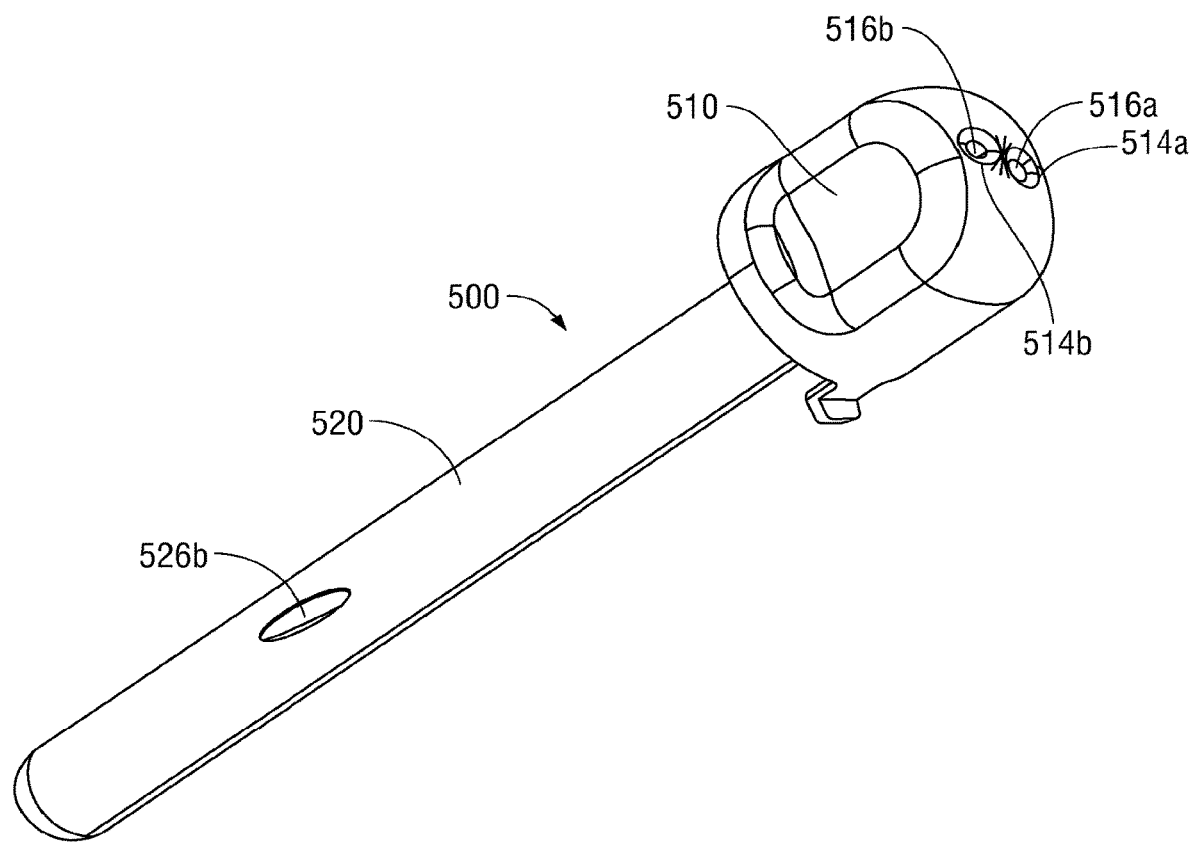
FIG. 12B is a second perspective view of the guide member of FIG. 11.

Turning to FIGS. 11-12B, another embodiment of a guide member configured for use with cannula 100 and a suture passer, e.g., suture passer 700 or any other suitable suture passer, for closing an opening in tissue is shown generally identified by reference numeral 500. Guide member 500 generally includes a guide housing 510 disposed in mechanical cooperation with an elongated guide shaft 520. Guide member 500 further includes a pair of guide lumens 516a, 516b extending between respective apertures 514a, 514b defined through guide housing 510 and respective slots 526a, 526b defined through guide shaft 520. Guide member 500 is similar to guide member 400 (FIGS. 9-10C) except that lumens 516a, 516b of guide member 500 do not define radii of curvature but, rather, define curved configurations that vary in degree of curvature along the length of lumens 516a, 516b, e.g., lumens 516a, 516b define "J"-shaped configurations. More specifically, the proximal portions of lumens 516a, 516b define a lesser degree of curvature, thus enabling insertion of suture passer 700 therethrough in substantially parallel alignment with the longitudinal axis of guide member 500 (see, e.g., FIG. 11), while the distal portions of lumens 516a, 516b define a greater degree of curvature to route suture passer 700 therethrough at an appropriate angle relative to tissue (see, e.g., FIG. 11). As such, guide member 500 is configured for use with a suture passer having a flexible shaft that enables the suture passer to conform to the varying curvature of lumens 516a, 516b upon insertion therethrough.

Figure 13:
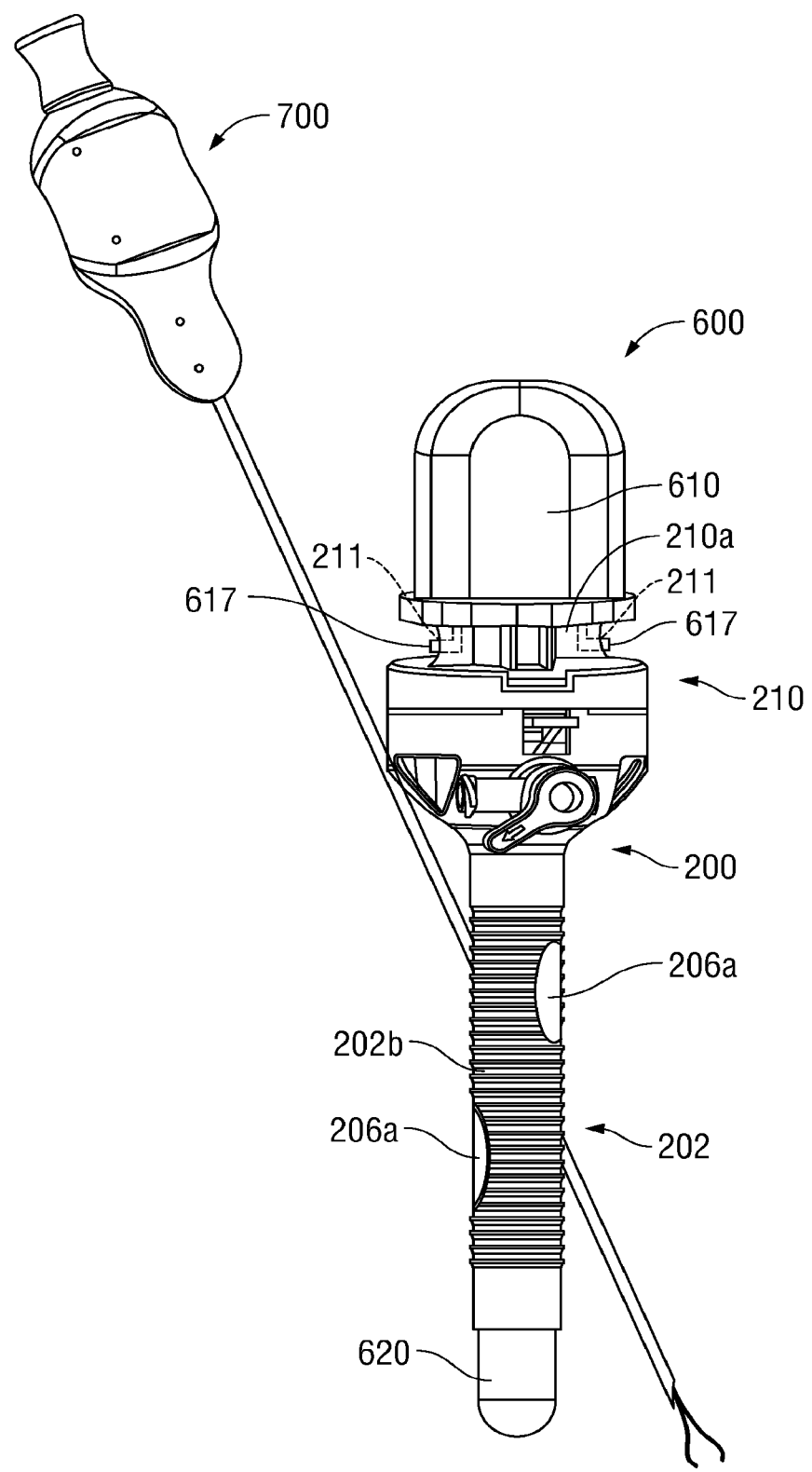
FIG. 13 is a side view of the cannula of FIGS. 6A-6B including another guide member engaged with the cannula and the suture passer of FIG. 7 inserted through the guide member and cannula.

Referring to FIGS. 13-14B, another embodiment of a guide member provided in accordance with the present disclosure is shown generally identified by reference numeral 600. Guide member 600 is configured for use with cannula 200 and a suture passer, e.g., suture passer 700 or any other suitable suture passer, for closing an opening in tissue. Guide member 600 generally includes a guide housing 610 disposed in mechanical cooperation with an elongated guide shaft 620.

Guide housing 610 includes a pair of engagement tabs 617 disposed on opposite sides of guide housing 610 and extending therefrom. Engagement tabs 617, similarly as detailed above with respect to guide member 400 (FIGS. 9-10C), are configured for releasable engagement within radially opposed apertures 211 defined though proximal housing component 210a of housing 210 of cannula 200 to permit releasable engagement and alignment of guide member 600 with cannula 200.

Elongated guide shaft 620 of guide member 600 extends distally from guide housing 610 and is configured for insertion through passageway 205 (FIG. 6B) of elongated tubular member 202a of cannula 200. Elongated shaft 620 includes a pair of angled lumens 626a, 626b extending therethrough. Although lumens 626a, 626b cross over one another, lumens 626a, 626b are radially staggered relative to one another such that lumens 626a, 626b do not intersect. Upon insertion and engagement of guide member 600 within cannula 200, angled lumens 626a, 626b are aligned with first and second slot axes "A-A," "B-B," respectively (see FIG. 6A). That is, angled lumens 626a, 626b are disposed between the proximal and distal slots of respective pairs of slots 206a, 206b. As such, a suture passer, e.g., suture passer 700 or any other suitable suture passer, may be inserted through the proximal slot of either of the pairs of slots 206a, 206b (penetrating the sealing member disposed thereabout), the corresponding lumen 616a, 616b, the distal slot of the corresponding pair of slots 206a, 206b (penetrating the sealing member disposed thereabout), tissue, and into the internal surgical site to facilitate closure of the opening in tissue.

Figure 15:
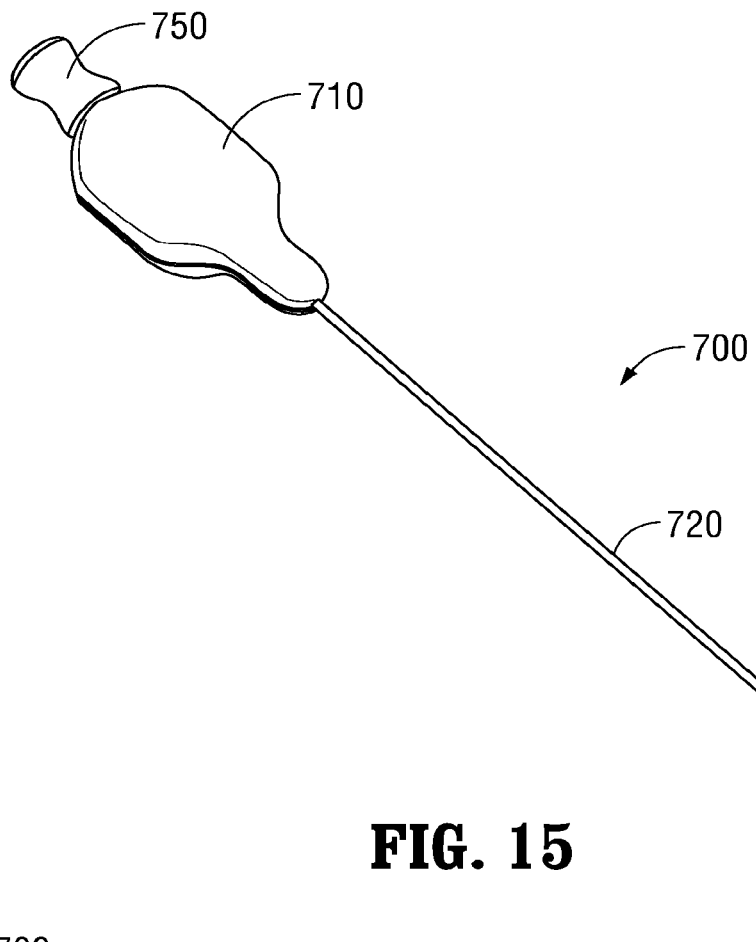
FIG. 15 is a perspective view of the suture passer of FIG. 7.
Figure 16A:
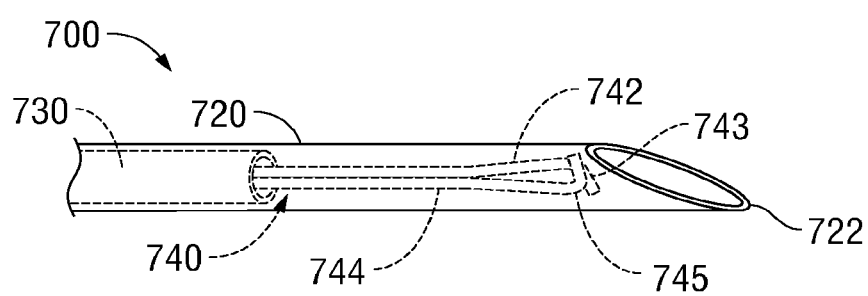
FIG. 16A is an enlarged, perspective view of the distal end of the suture passer of FIG. 7 disposed in an insertion/withdrawal condition.
Figure 16B:
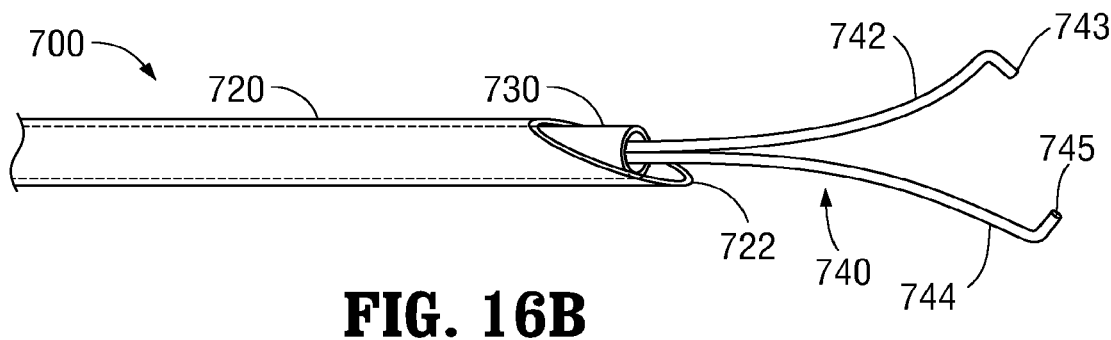
FIG. 16B is an enlarged, perspective view of the distal end of the suture passer of FIG. 7 disposed in a deployed condition.

With reference to FIGS. 15-16B, suture passer 700 is described. As noted above, suture passer 700 may be configured for use with any or all of guide members 300, 400, 500, 600 (FIGS. 7-14B). Suture passer 700 generally includes a handle 710, an elongated sleeve 720, an inner shaft 730, an end effector assembly 740, and a plunger 750. Elongated sleeve 720 and inner shaft 730 are both flexible to permit insertion through any of the lumens of guide members 300, 400, 500, 600 (FIGS. 7-14). Alternatively, elongated sleeve 720 and inner shaft 730 may define rigid, curved configurations have a radius of curvature equal to that of the lumens of guide member 300 or guide member 400 (FIGS. 78B and 9-10C, respectively) for use therewith, or may define rigid, linear configurations. Further, elongated sleeve 720 defines a distal tip 722 configured to facilitate penetration of elongated sleeve 720 through tissue (and through the sealing member(s) of cannula 100). Distal tip 722 may define a sharpened configuration or may define a blunt configuration.

Elongated sleeve 720 of suture passer 700 is fixed relative to handle 710 and extends distally from handle 710. Inner shaft 730 is slidably disposed within elongated sleeve 720 and is coupled to plunger 750 within handle 710. As such, inner shaft 730 is selectively slidable relative to handle 710 and elongated sleeve 720 upon manual translation of plunger 750 relative to handle 710 between a retracted position (FIG. 16A) and an extended position (FIG. 16B). A biasing member (not shown) may be provided for biasing inner shaft 730 towards the retracted position (FIG. 16A).

End effector assembly 740 is disposed at the distal end of inner shaft 730 and includes a pair of spring arms 742, 744 extending from the distal end of inner shaft 730. Spring arms 742, 744 are biased towards a spaced-apart position relative to one another and define bent fingers 743, 745 at the respective free ends thereof. In the retracted position of inner shaft 730, spring arms 742, 744 are retained within the interior of elongated sleeve 720 such that spring arms 742, 744 are disposed in close approximation with each other and fingers 743, 745 at least partially overlap each other. This position corresponds to the insertion/withdrawal condition of suture passer 700, wherein a portion of suture disposed between spring arms 742, 744 is retained therebetween for insertion into and/or withdrawal from the internal surgical site and wherein distal tip 722 of elongated sleeve 720 is exposed to facilitate tissue penetration. In the extended position of inner shaft 730 (FIG. 16B), spring arms 742, 744 extend distally from elongated sleeve such that spring arms 742, 744 are uninhibited by elongated sleeve 720, thus permitting spring arms 742, 744 to achieve the spaced-apart position corresponding to a deployed condition of suture passer 700. In this deployed condition, end effector assembly 740 may be manipulated into position such that a portion of suture to be grasped is positioned between spring arms 742, 744. Once this position has been achieved, plunger 750 may be grasped and translated proximally relative to handle 710 to translate inner shaft 730 proximally relative to elongated sleeve 720 from the extended position (FIG. 16B) back to the retracted position (FIG. 16A).

As an alternative to elongated sleeve 720 being fixed relative to handle 710 and inner shaft 730 being selectively slidable relative to handle 710 and elongated sleeve 720 to transition suture passer 700 between the insertion/withdrawal condition and the deployed condition, this configuration may be reversed. That is, inner shaft 730 may be fixed relative to handle 710 and plunger 750 may be coupled to elongated sleeve 720 such that manual translation of plunger 750 relative to handle 710 effects translation of elongated sleeve 720 relative to handle 710 and inner shaft 730 between the position shown in FIG. 16A, wherein spring arms 742, 744 are retained within the interior of elongated sleeve 720, and the position shown in FIG. 16B, wherein spring arms 742, 744 are permitted to achieve the spaced-apart position.

Figure 17A:
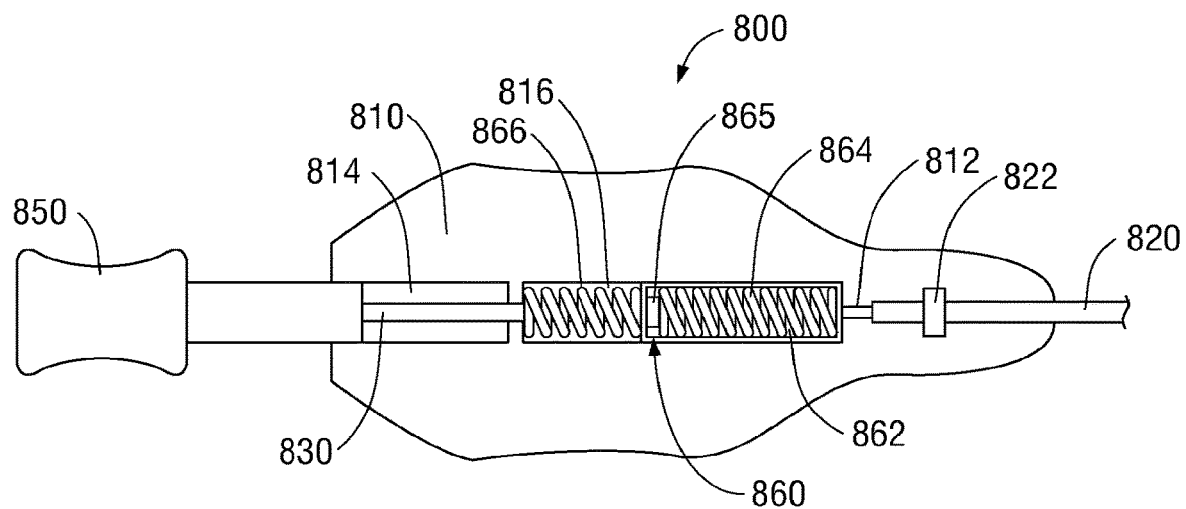
FIG. 17A is a side, cut-away view of the proximal end of another suture passer provided in accordance with the present disclosure disposed in an insertion/withdrawal condition.
Figure 17B:
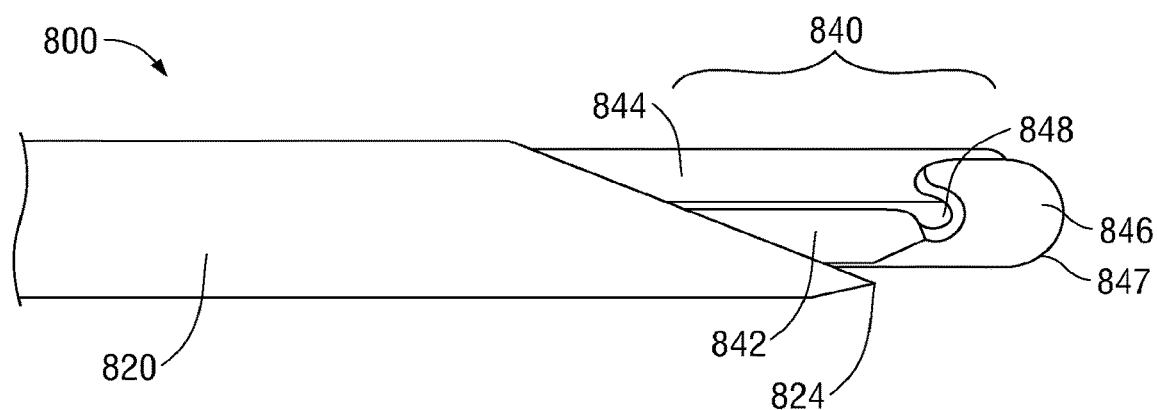
FIG. 17B is a perspective view of the distal end of the suture passer of FIG. 17A disposed in the insertion/withdrawal condition.
Figure 18A:
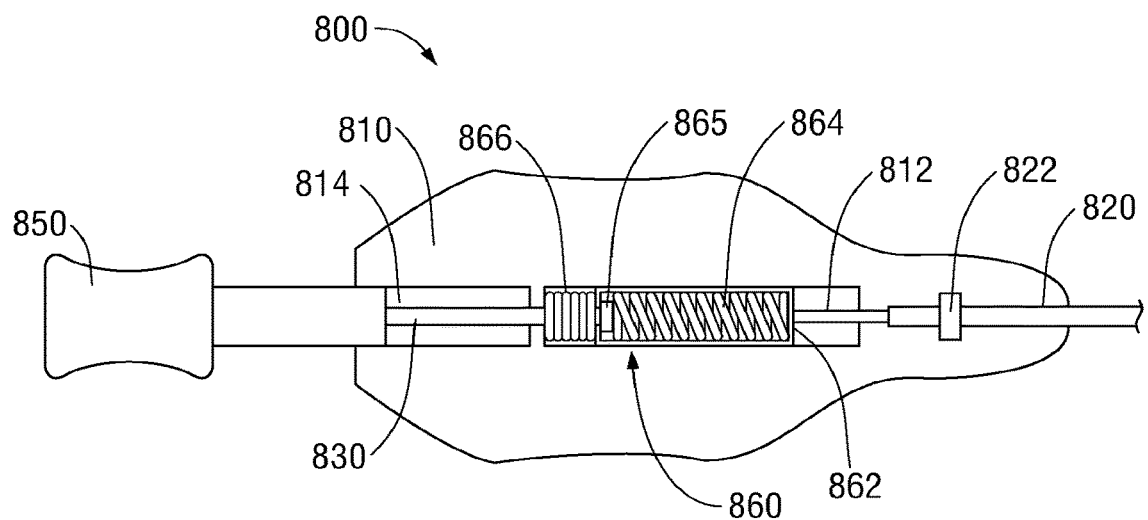
FIG. 18A is a side, cut-away view of the proximal end of the suture passer of FIG. 17A disposed in a piercing condition.
Figure 18B:
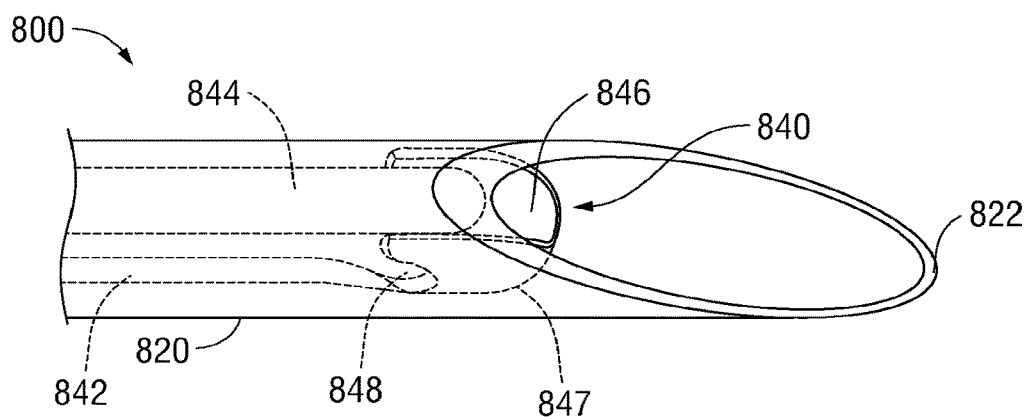
FIG. 18B is a perspective view of the distal end of the suture passer of FIG. 17A disposed in the piercing condition.
Figure 19A:
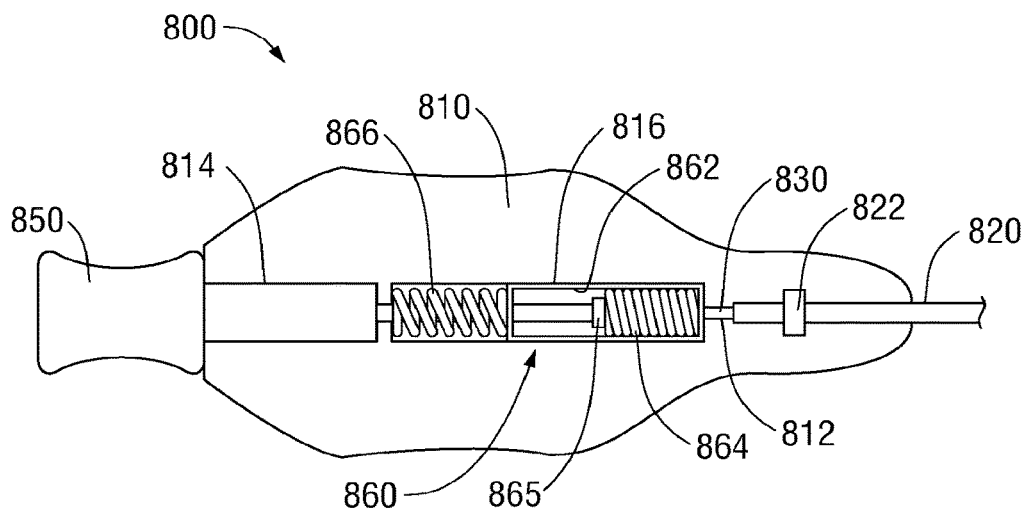
FIG. 19A is a side, cut-away view of the proximal end of the suture passer of FIG. 17A disposed in a deployed condition.
Figure 19B:
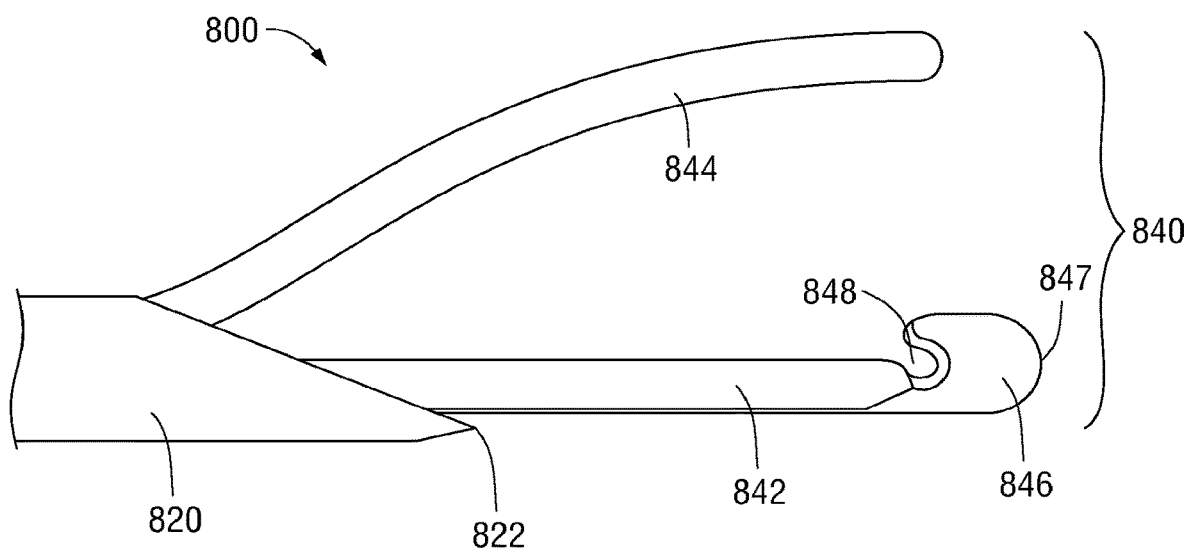
FIG. 19B is a perspective view of the distal end of the suture passer of FIG. 17A disposed in the deployed condition.

With reference to FIGS. 17A-19B, another embodiment of a suture passer 800 configured for use with any or all of guide members 300, 400, 500, 600 (FIGS. 7-14B) is described. As detailed below, suture passer 800 is transitionable between an insertion/withdrawal condition (FIGS. 17A-17B), a piercing condition (FIGS. 18A-18B), and a deployed condition (FIGS. 19A-19B). Suture passer 800 generally includes a handle 810, an elongated sleeve 820, an inner shaft 830, an end effector assembly 840, and a plunger 850. Elongated sleeve 820 and inner shaft 830 are both flexible to permit insertion through any of the lumens of guide members 300, 400, 500, 600 (FIGS. 7-14). Alternatively, elongated sleeve 820 and inner shaft 830 may define rigid, curved configurations having a radius of curvature equal to that of the lumens of guide member 300 or guide member 400 (FIGS. 7-8B and 9-10C, respectively) for use therewith, or may define rigid, linear configurations.

Elongated sleeve 820 of suture passer 800 is fixed within handle 810 via a bushing 822 and extends distally from handle 810. Elongated sleeve 820 defines a sharpened distal tip 824 configured to facilitate piercing tissue upon advancement of elongated sleeve 820 through tissue (and for penetrating the sealing members of cannula 100 (FIGS. 5A-5B)), although distal tip 824 may alternatively define a blunt configuration.

Inner shaft 830 of suture passer 800 is slidably disposed within elongated sleeve 820 and a longitudinal lumen 812 extending through handle 810. Longitudinal lumen 812 includes first and second chambers 814, 816. First chamber 814 is configured to slidably receive a distal portion of plunger 850 to permit longitudinal reciprocation of plunger 850 relative to handle 810 between a proximal position (FIG. 18A), an intermediate position (FIG. 17A) and a distal position (FIG. 19A). The distal end of plunger 850 is engaged to the proximal end of inner shaft 830 such that reciprocation of plunger 850 relative to handle 810 translates inner shaft 830 through and relative to handle 810 and elongated sleeve 820.

A biasing assembly 860 is disposed within second chamber 816 of longitudinal lumen 812 of handle 810 of suture passer 800. Biasing assembly 860 includes a cartridge 862, a first biasing member 864, and a second biasing member 866. Cartridge 862 is slidably disposed about inner shaft 830 and slidably disposed within second chamber 816. First biasing member 864 is disposed about inner shaft 830 within cartridge 862 and is fixed to inner shaft 830 at a proximal end of first biasing member 864 via a collar 865. Second biasing member 866 is disposed about inner shaft 830 within second chamber 816 between the proximal end of second chamber 816 and cartridge 862. As a result of this configuration, biasing assembly 860 biases suture passer 800 towards the insertion/withdrawal condition (FIGS. 17A-17B).

End effector assembly 840 is disposed at the distal end of inner shaft 830 and includes a receiver shaft 842 and a spring arm 844. Receiver shaft 842 defines a semi-cylindrical hollow interior that is configured to receive spring arm 844 in the insertion/withdrawal and piercing conditions of suture passer 800 (FIGS. 17B and 18B, respectively). Receiver shaft 842 further includes a distal cap 846 disposed at a distal end thereof. Distal cap 846 defines a blunt distal end 847 and proximally-facing hook-shaped cut-outs 848 on each side thereof that are configured to receive a portion of suture therein. Spring arm 844 is biased towards a spaced-apart position relative to receiver shaft 842 corresponding to the deployed condition (FIG. 19B) of suture passer 800. Upon proximal retraction of end effector assembly 840 into elongated sleeve 820, spring arm 844 is urged via camming engagement with elongated sleeve 820 towards an approximated position wherein spring arm 844 is disposed within the hollow interior of receiver shaft 842 and the distal end of spring arm 844 is positioned within distal cap 846 of receiver shaft 842. Spring arm 844 is disposed in this approximated position in both the piercing condition (FIG. 18B) and the insertion/withdrawal condition (FIG. 17B) of suture passer 800.

In use, with reference to FIGS. 17A-17B, suture passer 800 is initially disposed, at-rest, in the insertion/withdrawal condition, wherein end effector assembly 840 extends distally from distal tip 824 of elongated sleeve 820 so as to inhibit distal tip 824 from inadvertently piercing, catching, or otherwise causing damage. In the insertion/withdrawal condition of suture passer 800, plunger 850 is disposed in the intermediate position. As detailed above, in the insertion/withdrawal condition, spring arm 844 is disposed in the approximated position within the hollow interior of receiver shaft 842. Depending on a particular purpose, a portion of suture may be disposed within hook-shaped cut-outs 848 of receiver shaft 842 for insertion through tissue and into the internal surgical site. Alternatively, where a portion of suture is to be retrieved, suture passer 800 may remain empty.

Referring additionally to FIGS. 18A-18B, with suture passer 800 disposed in the insertion/withdrawal condition (FIGS. 17A-17B), suture passer 800 may be inserted through a lumen of a guide member, e.g., any of guide members 300, 400, 500, 600 (FIGS. 7-14), and into contact with tissue surrounding the opening. Upon contacting tissue, the resistance force of tissue acting on suture passer 800 urges end effector assembly 840 proximally relative to elongated sleeve 820 against the bias of second biasing member 866 such that end effector assembly 840 is pushed into elongated sleeve 820 to expose distal tip 824 of elongated sleeve 820. As end effector assembly 840 is pushed proximally into elongated sleeve 820, inner shaft 830 and plunger 850 are also translated proximally such that plunger 850 is moved to the proximal position. This position of end effector assembly 840 corresponds to the piercing condition of suture passer 800 (FIG. 18A-18B). Thus, upon further advancement of suture passer 800 though tissue, distal tip 824 facilitates the piercing of tissue. Upon reaching the internal surgical site, e.g., once tissue is no longer providing a suitable resistance force, suture passer 800 is returned under the bias of second biasing member 866 to the at-rest, insertion/withdrawal condition (FIGS. 17A-17B), wherein end effector assembly 840 extends distally from distal tip 824 of elongated sleeve 820 so as to inhibit distal tip 824 from inadvertently piercing, catching, or otherwise causing damage. As noted above, plunger 850 is disposed in the intermediate position in the insertion/withdrawal condition of suture passer 800 (FIGS. 17A-17B).

With additional reference to FIGS. 19A-19B, once suture passer 800 has been inserted through the guide member, tissue, and into the internal surgical site, suture passer 800 may be transitioned from the insertion/withdrawal condition (FIGS. 17A-17B) to the deployed condition (FIGS. 19A-19B) by translating plunger 850 distally relative to handle 810 from the intermediate position to the distal position against the bias of first biasing member 864. Translating plunger 850 to the distal position extends end effector assembly 840 from elongated sleeve 820 such that spring arm 844 is permitted to return under bias to the spaced-apart position relative to receiver shaft 842, corresponding to the deployed condition of suture passer 800. In this position, suture passer 800 may be manipulated to release a portion of suture retained via end effector assembly 840 or to position a portion of suture to be retrieved between receiver shaft 842 and spring arm 844. Thereafter, plunger 850 may be released to allow suture passer 800 to return under bias to the insertion/withdrawal condition (FIGS. 17A-17B), wherein spring arm 844 is approximated within the hollow interior of receiver shaft 842. Where a portion of suture is to be retrieved, transitioning suture passer 800 back to the insertion/withdrawal condition (FIGS. 17A-17B) and withdrawing suture passer 800 urges the portion of suture into hook-shaped cut-outs 848 to permit withdrawal of the portion of suture along with suture passer 800.

Figure 20A:
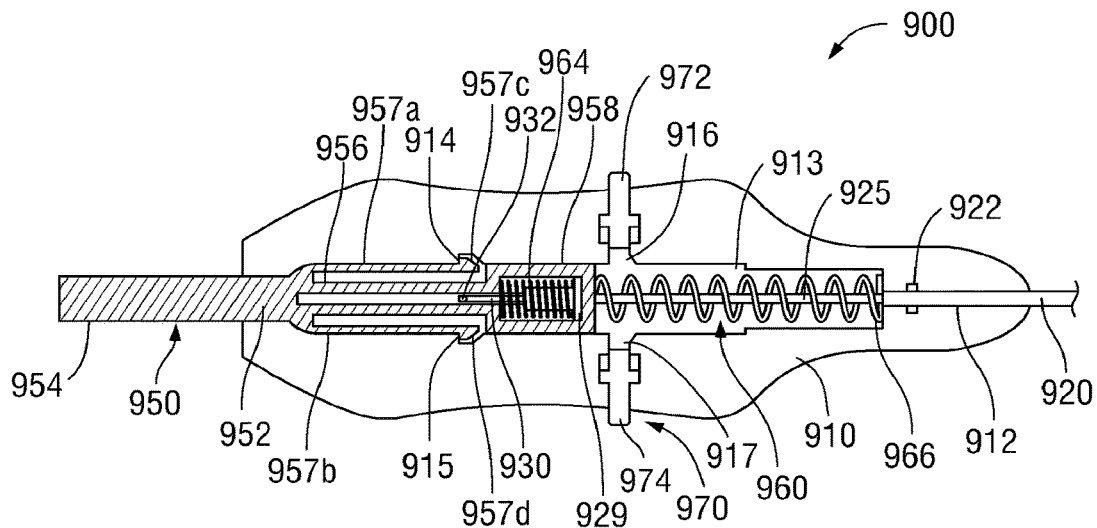
FIG. 20A is a side, cut-away view of the proximal end of another suture passer provided in accordance with the present disclosure, disposed in a deployed condition.
Figure 20B:
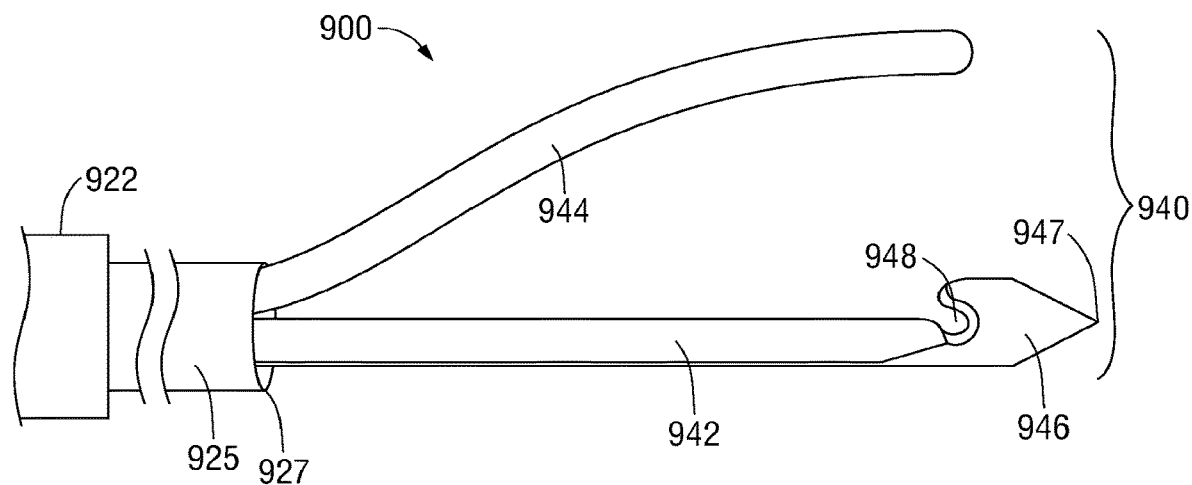
FIG. 20B is a perspective view of the distal end of the suture passer of FIG. 20A, disposed in the deployed condition.
Figure 21A:
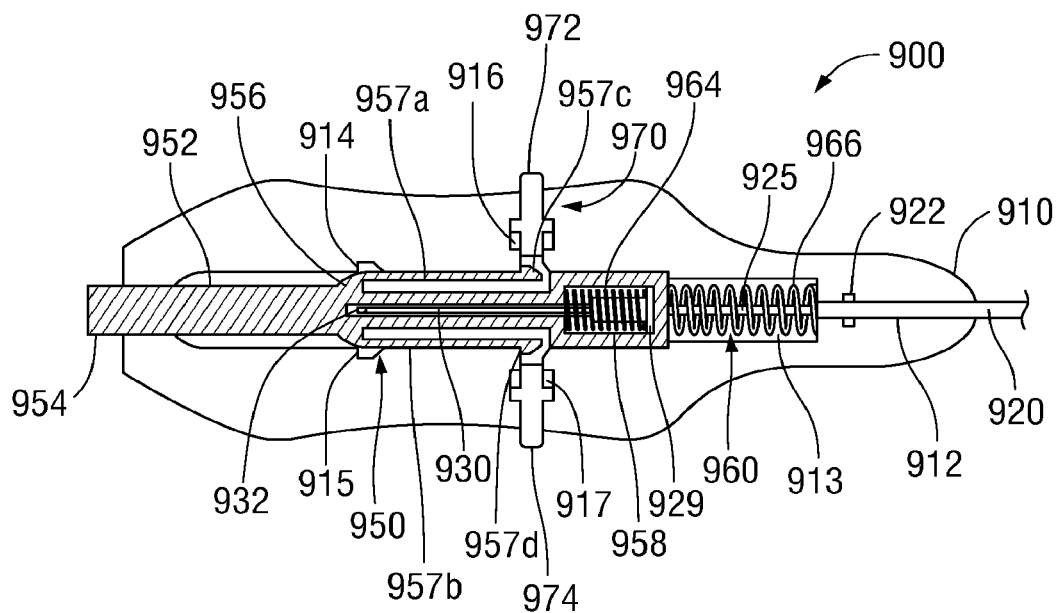
FIG. 21A is a side, cut-away view of the proximal end of the suture passer of FIG. 20A, disposed in an insertion/withdrawal condition.
Figure 21B:
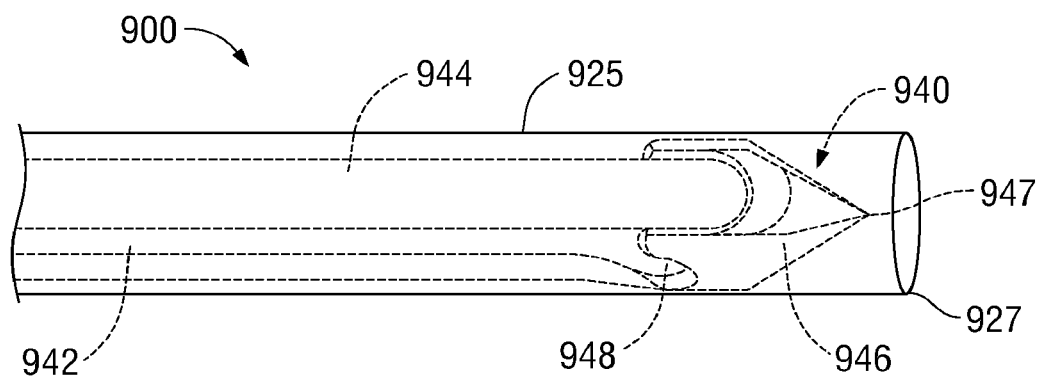
FIG. 21B is a perspective view of the distal end of the suture passer of FIG. 20A, disposed in the insertion/withdrawal condition.
Figure 22A:
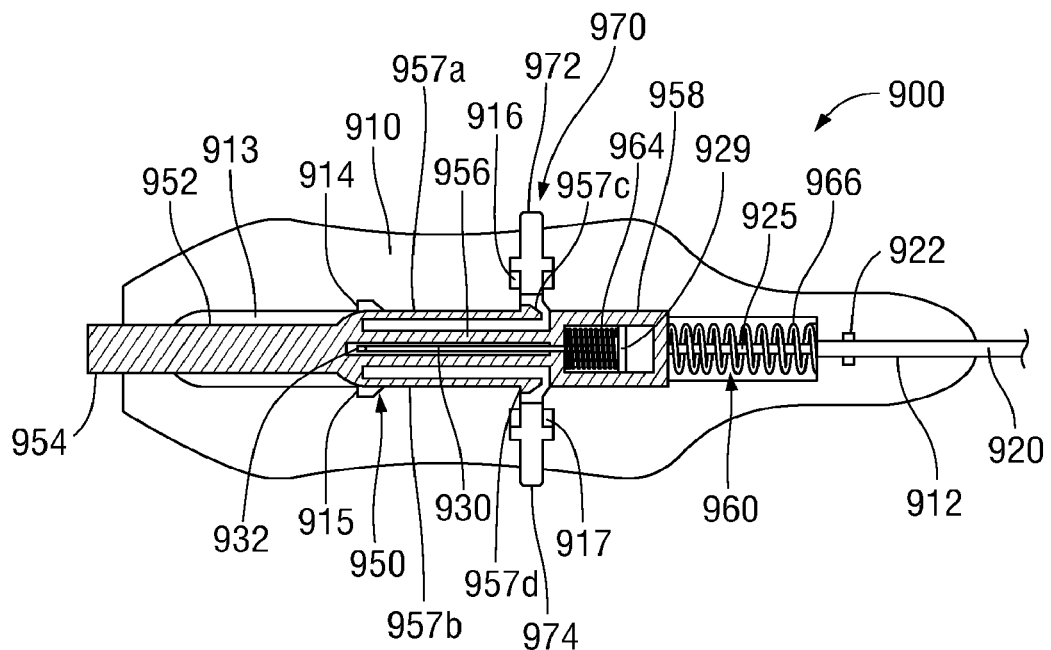
FIG. 22A is a side, cut-away view of the proximal end of the suture passer of FIG. 20A, disposed in a piercing condition.
Figure 22B:
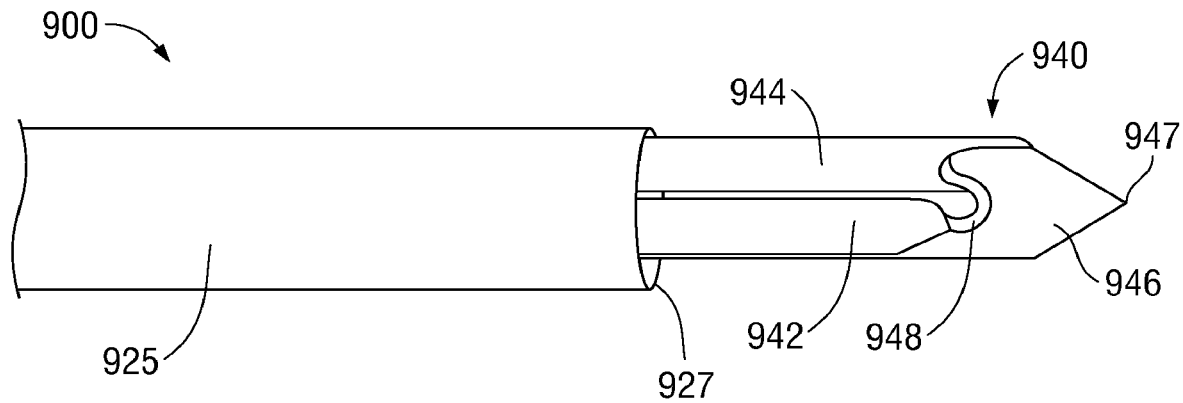
FIG. 22B is a perspective view of the distal end of the suture passer of FIG. 20B, disposed in the piercing condition.

With reference to FIGS. 20A-22B, another embodiment of a suture passer 900 configured for use with any or all of guide members 300, 400, 500, 600 (FIGS. 7-14B) is described. As detailed below, suture passer 900 is transitionable between a deployed condition (FIGS. 20A-20B), an insertion/withdrawal condition (FIGS. 21A-21B), and a piercing condition (FIGS. 22A-22B). Suture passer 900 generally includes a handle 910, a fixed sleeve 920, a movable sleeve 925, an inner shaft 930, an end effector assembly 940, a plunger assembly 950, a biasing assembly 960, and a release assembly 970. Fixed sleeve 920, movable sleeve 925, and inner shaft 930 are flexible to permit insertion through any of the lumens of guide members 300, 400, 500, 600 (FIGS. 7-14). Alternatively, these components may define rigid, curved configurations having a radius of curvature equal to that of the lumens of guide member 300 or guide member 400 (FIGS. 7-8B and 9-10C, respectively) for use therewith, or may define rigid, linear configurations.

Fixed sleeve 920 of suture passer 900 is fixed within handle 910 via a bushing 922 and extends distally from handle 910. Movable sleeve 925 is slidable disposed within fixed sleeve 920 and a lumen 912 defined through handle 910. Movable sleeve 925 extends distally from fixed sleeve 920 and is slidable relative thereto to vary the amount movable sleeve 925 extends from fixed sleeve 920 (see FIG. 20B). Fixed sleeve 920 (see FIG. 20B) serves as a barrier to inhibit contact between movable sleeve 925 and surgical instrumentation (not shown) and/or tissue through which suture passer 900 is inserted, thus inhibiting rubbing or catching of movable sleeve 925 upon translation relative to the surgical instrumentation (not shown) and/or tissue. Movable sleeve 925 defines a blunt distal end 927 and is coupled to plunger assembly 950 within handle 910 via a ferrule 929 disposed at the proximal end thereof, as detailed below.

Inner shaft 930 of suture passer 900 extends distally from lumen 912 of handle 910 through movable sleeve 925. Inner shaft 930 is fixed to handle 910 at its proximal end via a pin 932, although other securement mechanisms are also contemplated. End effector assembly 940 is disposed at the distal end of inner shaft 930 and includes a receiver shaft 942 and a spring arm 944. Receiver shaft 942 defines a semi-cylindrical hollow interior that is configured to receive spring arm 944 in both the insertion/withdrawal condition (FIGS. 21A-21B) and the piercing condition (FIGS. 22A-22B) of suture passer 900. Receiver shaft 942 further includes a distal cap 946 disposed at a distal end thereof. Distal cap 946 defines a sharpened or pointed distal piercing tip 947 configured to facilitate piercing through tissue (and the sealing members of cannula 100 (FIGS. 5A-5B)), and proximally-facing hook-shaped cut-outs 948 on each side thereof that are configured to receive a portion of suture therein. Spring arm 944 is biased towards a spaced-apart position relative to receiver shaft 942 corresponding to the deployed condition (FIG. 20B) of suture passer 900. Upon distal extension of movable sleeve 925 about end effector assembly 940, as detailed below, spring arm 944 is urged via camming engagement with movable sleeve 925 towards an approximated position wherein spring arm 944 is disposed within the hollow interior of receiver shaft 942 and the distal end of spring arm 944 is positioned within distal cap 946 of receiver shaft 942. Spring arm 944 is disposed in this approximated position in both the insertion/withdrawal condition (FIGS. 21A-21B), and the piercing condition (FIGS. 22A-22B) of suture passer 900.

Plunger assembly 950 includes a plunger member 952 slidably disposed within a chamber 913 of lumen 912 of handle 910. Plunger member 952 includes a proximal shaft 954 that extends proximally from handle 910 to enable manual depression of proximal shaft 954 into handle 910, a locking component 956 configured to substantially lock suture passer 900 in the insertion/withdrawal condition (FIGS. 21A-21B), and a distal cartridge 958 disposed about ferrule 929 of movable shaft 925. Locking component 956 interconnects proximal shaft 954 and distal cartridge 958. Plunger member 952 may be formed as a monolithic component or the components thereof may otherwise be secured to each other in any suitable fashion. Locking component 956 of plunger member 952 includes first and second spring legs 957a, 957b each including an engagement toe 957c, 957d, respectively, disposed at the free end thereof. As detailed below, engagement toes 957c, 957d are configured to abut shoulders 914, 915 defined within handle 910 to inhibit further proximal travel of plunger member 952 relative to handle 910, and to spring into engagement within slots 916, 917 defined through handle 910 to substantially lock suture passer 900 in the insertion/withdrawal condition (FIGS. 21A-21B).

Biasing assembly 960 is disposed within chamber 913 of lumen 912 of handle 910 and includes a first biasing member 964 and a second biasing member 966. First biasing member 964 is disposed within distal cartridge 958 of plunger assembly 950 between the proximal end of distal cartridge 958 and ferrule 929, which is disposed at the proximal end of movable sleeve 925. As such, plunger member 952 is operably coupled to movable sleeve 925 to effect translation thereof upon translation of plunger member 952 in a similar direction. However, this coupling also provides a degree of play, that is, movable sleeve 925 is translatable relative to plunger member 952 via movement of ferrule 929 within distal cartridge 958, e.g., under or against the bias of first biasing member 964. Second biasing member 966 is disposed about movable sleeve 925 between distal cartridge 958 and the distal end of chamber 913 of lumen 912 so as to bias plunger member 952 proximally.

Release assembly 970 includes a pair of opposed release members 972, 974 slidably disposed within respective slots 916, 917 defined through handle 910. Release members 972, 974 are movable relative to handle 910 between an initial position (FIG. 20A), wherein release members 972, 974 extend only partially into slots 916, 917, respectively, and a release position (not shown), wherein release member 972, 974 extend further into slots 916, 917, respectively to ultimately contact respective engagement toes 957c, 957d and urge respective engagement toes 957c, 957d out of engagement with respective slots 916, 917 to unlock suture passer 900 from the insertion/withdrawal condition (FIGS. 21A-21B), as detailed below. Biasing members (not shown) may be provided for biasing release members 972, 974 towards the initial position, although other configurations are also contemplated.

In use, initially referring to FIGS. 20A-20B, suture passer 900 is disposed in the deployed condition, wherein movable shaft 925 is proximally spaced from end effector assembly 940 such that spring arm 944 of end effector assembly 940 is disposed in the spaced-apart position relative to receiver shaft 942. As such, a portion of suture may be positioned within or removed from end effector assembly 940, similarly as detailed above with respect to suture passer 800 (FIGS. 17A-19B). In the deployed condition, plunger member 952 is biased proximally by second biasing member 966 such that engagement toes 957c, 957d abut shoulders 914, 915 defined within handle 910, thereby inhibiting plunger member 952 from translating further proximally relative to handle 910. At this point, release members 972, 974 remain disposed in the initial position.

With additional reference to FIGS. 21A-21B, in order to prepare suture passer 900 for insertion, suture passer 900 is transitioned to the insertion/withdrawal condition by depressing or translating plunger member 952 distally relative to handle 910. Distal translation of plunger member 952 relative to handle 910 translates movable sleeve 925 distally about and relative to inner shaft 930 and end effector assembly 940 such that movable sleeve 925 urges spring arm 944 to the approximated position and, ultimately, fully encloses end effector assembly 940. By fully enclosing end effector assembly 940, distal piercing tip 947 of end effector assembly 940 is inhibited from inadvertently piercing, catching, or otherwise causing damage. Concomitantly with the distal translation of movable sleeve 925, locking component 956 of plunger member 952 is translated distally, ultimately such that engagement toes 957c, 957d are positioned adjacent respective slots 916, 917 of handle 910, thus permitting engagement toes 957c, 957d to spring into engagement within slots 916, 917. Plunger member 952 may then be released as the engagement of engagement toes 957c, 957d within slots 916, 917 substantially locks suture passer 900 in the insertion/withdrawal condition (FIGS. 21A-21B). Suture passer 900 is only substantially locked in the insertion/withdrawal condition (FIGS. 21A-21B) since movable sleeve 925 is still translatable relative to plunger member 952 via movement of ferrule 929 within distal cartridge 958. The importance of this feature is detailed below.

Referring additionally to FIGS. 22A-22B, with suture passer 900 disposed in the insertion/withdrawal condition (FIGS. 21A-21B), suture passer 900 may be inserted through a lumen of a guide member, e.g., any of guide members 300, 400, 500, 600 (FIGS. 7-14), and into contact with tissue surrounding the opening. Upon contacting tissue, the resistance force of tissue acting on suture passer 900 urges movable sleeve 925 proximally relative to end effector assembly 940 against the bias of first biasing member 964 such that distal piercing tip 947 of end effector assembly 940 is at least partially exposed, corresponding to the piercing condition of suture passer 900 (FIGS. 22A-22B). This movement is permitted by the play provided in the coupling between distal cartridge 985 of plunger member 952 and ferrule 929 of movable sleeve 925. With distal piercing tip 947 of end effector assembly 940 exposed, advancement of suture passer 900 though tissue can be more readily achieved. Upon reaching the internal surgical site, e.g., once tissue is no longer providing a suitable resistance force, suture passer 900 is returned under the bias of first biasing member 964 to the insertion/withdrawal condition (FIGS. 21A-21B), wherein movable sleeve 925 once again encloses end effector assembly 940 so as to inhibit distal piercing tip 947 of end effector assembly 940 from inadvertently piercing, catching, or otherwise causing damage.

Once suture passer 900 has been inserted through the guide member, tissue, and into the internal surgical site, suture passer 900 may be returned to the deployed condition (FIGS. 20A-20B) by squeezing release members 972, 974 inwardly relative to handle 910 such that release members 972, 974 are advanced further into slots 916, 917, respectively, to urge engagement toes 957c, 957d, respectively, out of engagement with respective slots 916, 917, thereby unlocking suture passer 900 from the insertion/withdrawal condition (FIGS. 21A-21B) and permitting suture passer 900 to return to the deployed position (FIGS. 20A-20B) under the bias of second biasing member 966. In the deployed position, a portion of suture may be positioned within or removed from end effector assembly 940, similarly as detailed above with respect to suture passer 800 (FIGS. 17A-19B). Ultimately, suture passer 900 may be returned to the insertion/withdrawal condition (FIGS. 21A-21B) as detailed above, and withdrawn from the internal surgical site.

Any of the above-detailed suture passers may further include one or more flush ports to enable flush-cleaning of the interior of the suture passer. Further, seals may be provided on or within the suture passers to separate the insertable portions from the handle or exterior portions, thus helping to contain contaminants, e.g., tissue, blood, fluids, and/or debris, to limited portions of the suture passer to facilitate cleaning. The suture passers may additionally or alternatively be configured for selective disassembly (and be made of sterilizable reusable and/or disposable components) to facilitate cleaning and/or replacement of disposable components. Likewise, the internal working components disposed within the handles of the suture passers may be exposed, e.g., via windows, openings, and/or cut-outs in the handles, to facilitate cleaning.

As can be appreciated, the various cannulas, guide members, and suture passers detailed above, to the extent compatible with one another, can be utilized in any suitable combination with obturator 11 (FIG. 2) or other suitable obturator to access an internal surgical site through an opening in tissue, perform one or more minimally-invasive surgical tasks within the internal surgical site (under insufflation if required), and close the opening in tissue once the surgical task(s) is complete. Alternatively, any of the guide members may incorporate the features of obturator 11 (FIG. 2), e.g., an atraumatic guiding nub 26 (FIG. 2), and, thus, may function as both the obturator and the guide member, obviating the need for a separate obturator. In use, the cannula and obturator (or guide member, in embodiments where the guide member also functions as the obturator) are first utilized to create and/or expand the opening in tissue and for positioning the cannula therein; the cannula, after withdrawal of the obturator (or guide member), is utilized to protect surrounding tissue, maintain insufflation, and/or guide surgical instrumentation (not shown) into the internal surgical site; the guide member is inserted into the cannula to and utilized to facilitate insertion and withdrawal of one of the suture passers through tissue adjacent the opening; and the suture passers are utilized to deposit and/or retrieve a portion of suture to/from the internal surgical site on either side of the opening in tissue to enable tying off of the suture to close the opening.

Any suitable suture or sutures may be utilized in conjunction with the above. In particular, the suture(s) may be provided in any suitable form and/or include any suitable feature(s) to facilitate insertion through and depositing the suture within the internal surgical site on one side of the opening in tissue, and retrieval and withdrawal of the portion of suture from the other side of the opening in tissue. Such a configuration establishes a "U"-shaped suture extending through tissue on either side of the opening and across the opening on the internal side of tissue. This configuration enables tying off of the externally-disposed free ends of the suture and provides sufficient holding strength to permit healing and resist re-opening of the sutured tissue. One particular embodiment of a suture retention and positioning member is detailed below with respect to FIGS. 23-24E.

Figure 23:
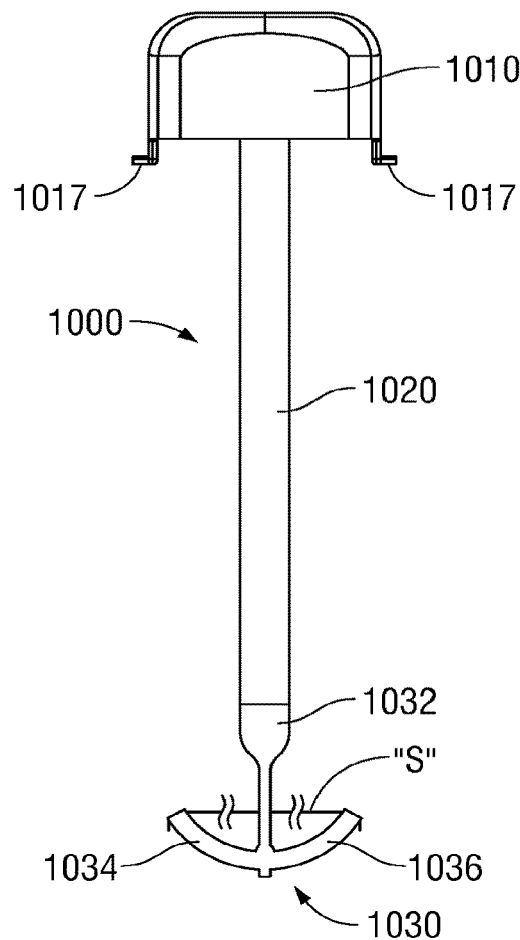
FIG. 23 is a side view of another guide member provided in accordance with the present disclosure.

Turning to FIGS. 23-24E, another embodiment of a guide member configured for use with cannula 100 and a suture passer, e.g., any of the suture passers detailed above or any other suitable suture passer, for closing an opening in tissue is shown generally identified by reference numeral 1000. As can be appreciated, guide member 1000 may alternatively be configured for use with cannula 200 (FIGS. 6A-6B). Guide member 1000 generally includes a guide housing 1010 disposed in mechanical cooperation with an elongated guide shaft 1020, and a suture retention and positioning member 1030 disposed at a distal end of elongated guide shaft 1020. Suture retention and positioning member 1030 may be permanently affixed to elongated guide shaft 1020 or may be releasably coupled thereto, e.g., via friction-fitting or other suitable releasable engagement. In embodiments where suture retention and positioning member 1030 is removable, suture retention and positioning member 1030 may similarly be coupled to any of the other guide members detailed herein for similar use therewith.

Guide housing 1010 and elongated guide shaft 1020 of guide member 1000 may be configured similar to any of the embodiments detailed above. That is, elongated guide shaft 1020 and/or guide housing 1010 may define lumens extending therethrough of any suitable configuration for routing a suture passer through guide member 1000, cannula 100, and tissue, similarly as detailed above. Guide housing 1010 further includes engagement tabs 1017 extending therefrom that are configured for releasable engagement within the radially opposed apertures 111 defined though proximal housing component 110a of housing 110 of cannula 100 (see FIGS. 4A-4B) to permit releasable engagement and alignment of guide member 1000 with cannula 100, similarly as detailed above. Alternatively, guide housing 1010 may include threading configured to engage base member 102b of cannula 100 (with housing 110 removed therefrom), as also detailed above. As these features are detailed above with respect to the other embodiments of guide members, they will not be repeated below.

Suture retention and positioning member 1030 includes a body portion 1032 disposed about the distal end of elongated guide shaft 1020 and first and second flexible arms 1034, 1036 extending from either side of body portion 1032. Arms 1034, 1036 are monolithically formed with body portion 1032 (or otherwise engaged thereto) to define living hinges (or other suitable hinge structure) therebetween, thus permitting arms 1034, 1036 to bend or flex relative to body portion 1032. Each arm 1034, 1036 further includes a slot (not explicitly shown) defined therein towards the free end thereof that is configured to frictionally retain a portion of a suture "S" therebetween. As shown in FIG. 23, suture "S" extends between the free ends of arms 1034, 1036. Further, arms 1034, 1036, at rest, define pre-bent configurations wherein the free ends of arms 1034, 1036 are curved proximally towards guide member 1000. As a result of this configuration, the portion of suture "S" extending between the free ends of arms 1034, 1036 is spaced-apart from arms 1034, 1036, facilitating the grasping of suture "S." This configuration also facilitates insertion of guide member 1000 into cannula 100, as detailed below. Suture "S" defines sufficient length so as to enable suture "S" to extend across the opening on the internal side of tissue, through the opening in tissue on either side thereof, and proximally from tissue sufficiently so as to enable tying off of the suture "S." The intermediate portion of suture "S" may be adhered, tacked, or otherwise stored within or on suture retention and positioning member 1030 during insertion of guide member 1000.

Figure 24A:
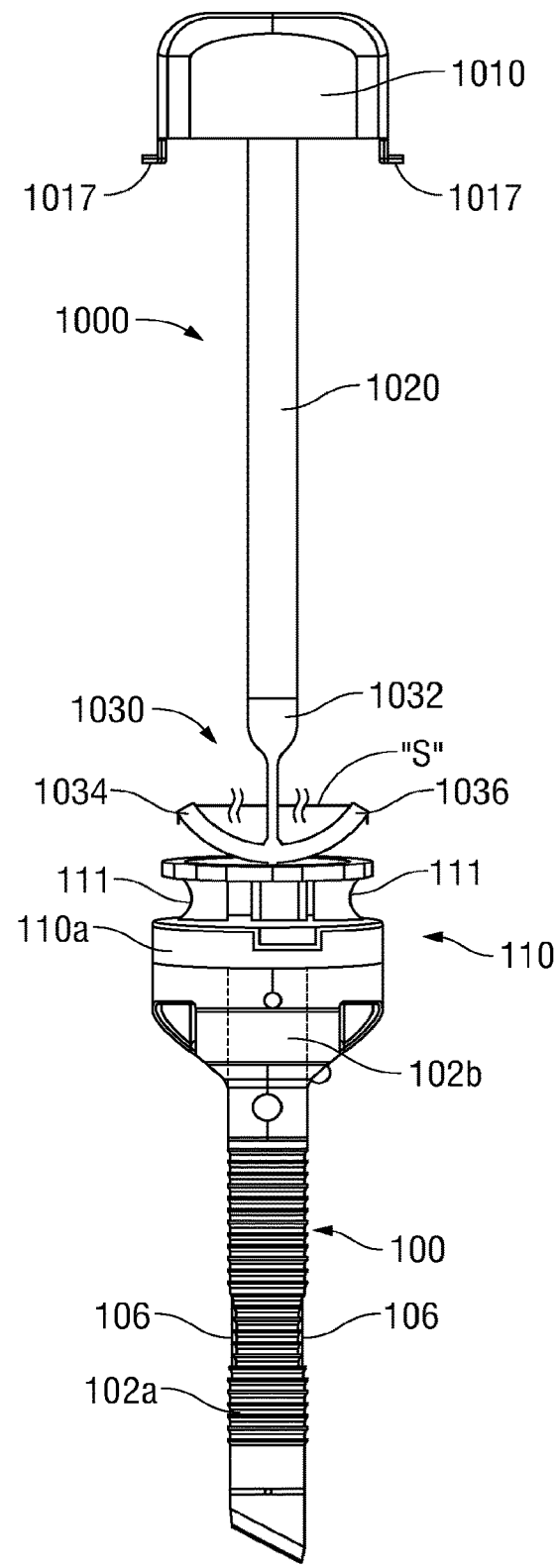
FIG. 24A is a side view of the guide member of FIG. 23 positioned for insertion into the cannula of FIG. 4A.
Figure 24B:
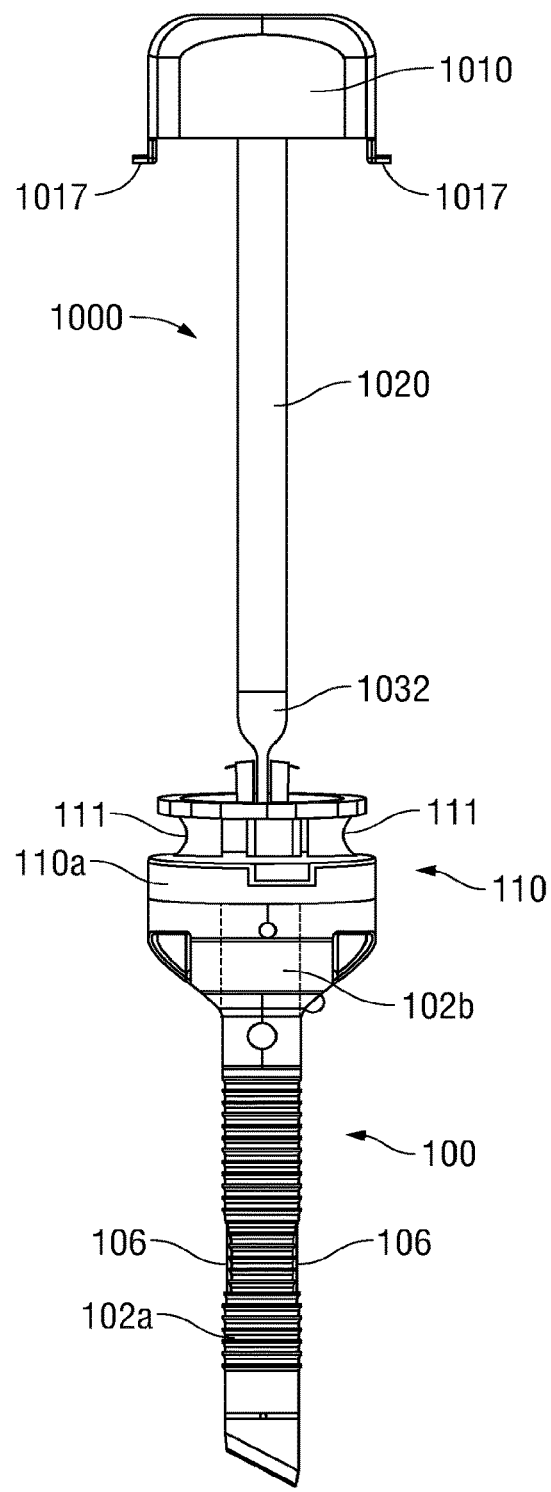
FIG. 24B is a side view of the guide member of FIG. 23 being inserted into the cannula of FIG. 4A.
Figure 24C:
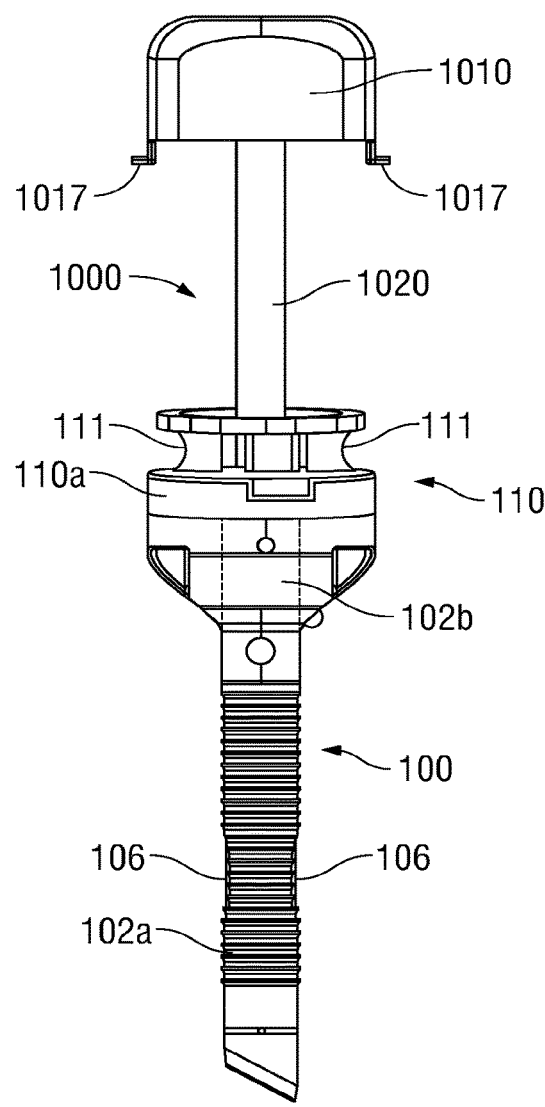
FIG. 24C is a side view of the guide member of FIG. 23 being inserted further into the cannula of FIG. 4A.

Turning now to FIGS. 24A-24E, the use of guide member 1000 in conjunction with cannula 100 is detailed. Initially, as shown in FIGS. 24A-C, guide member 1000, lead by suture retention and positioning member 1030 is inserted into cannula 100. As guide member 1000 is inserted into cannula 100, arms 1034, 1036 of suture retention and positioning member 1030 are flexed inwardly towards elongated guide shaft 1020 to permit insertion through cannula 100.

Referring to FIG. 24D, guide member 1000 is further inserted into cannula 100 until arms 1034, 1036 of suture retention and positioning member 1030 emerge from the distal end of cannula 100 and engagement tabs 1017 are engaged with apertures 111 to engage and align guide member 1000 with cannula 100. In this fully inserted position, arms 1034, 1036 are permitted to return to their at-rest positions such that a portion of suture "S" is presented on either side of cannula 100. The presented portions of suture "S" are operably positioned to enable grasping by a suture passer inserted through cannula 100 and guide member 1000. More specifically, a suture passer may be inserted through guide member 1000, cannula 100, and tissue on a first side of the opening in tissue to grasp a first portion of suture "S" and withdraw the first portion of suture "S" through tissue on the first side of the opening, followed by the suture passer being inserted through guide member 1000, cannula 100, and tissue on a second, opposite side of the opening in tissue to grasp a second portion of suture "S" and withdraw the second portion of suture "S" through tissue on the second side of the opening.

With reference to FIG. 24E, once the first and second portions of suture "S" have been retrieved on either side of the opening, as detailed above, guide member 1000 may be withdrawn from cannula 100. In order to withdraw guide member 1000, guide housing 1010 is grasped and translated proximally with sufficient force so as to disengage engagement tabs 1017 from apertures 111 and to flex arms 1034, 1036 distally and into approximation with one another so as to allow suture retention and positioning member 1030 to pass proximally through cannula 100. Once guide member 1000 has been removed, cannula 100 may likewise be removed and the first and second portions of suture "S" tied off to close the opening in tissue.

Figure 29:
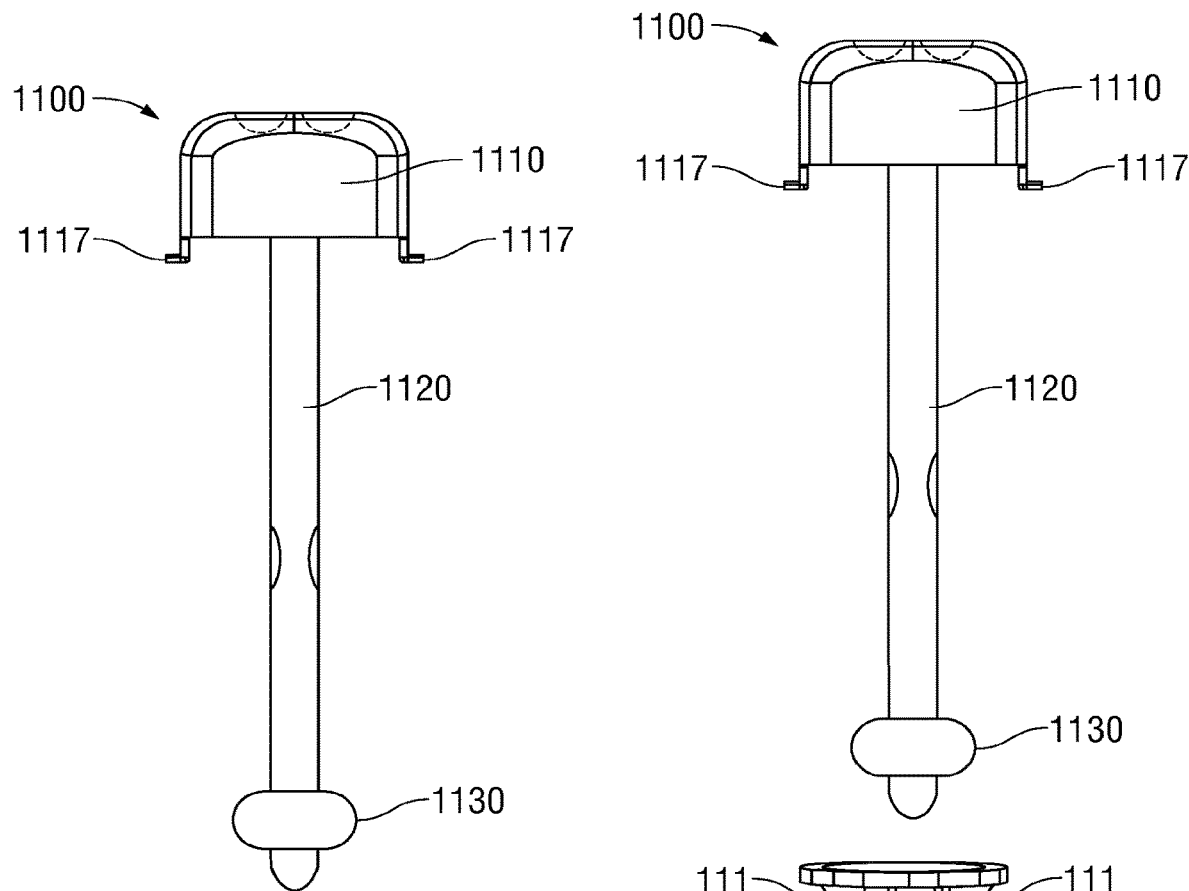
FIG. 29 is a side view of another guide member provided in accordance with the present disclosure.

Turning now to FIGS. 29-30C, another embodiment of a guide member configured for use with cannula 100 and a suture passer, e.g., any of the suture passers detailed above or any other suitable suture passer, for closing an opening in tissue is shown generally identified by reference numeral 1100. As can be appreciated, guide member 1100 may alternatively be configured for use with cannula 200 (FIGS. 6A and 6B). Guide member 1100 generally includes a guide housing 1110 disposed in mechanical cooperation with an elongated guide shaft 1120, and a cleaning member 1130 disposed towards a distal end of elongated guide shaft 1120. Cleaning member 1130 may be permanently affixed to elongated guide shaft 1120 or may be releasably coupled thereto. In embodiments where cleaning member 1130 is removable, cleaning member 1130 may similarly be coupled to any of the other guide members detailed herein for similar use therewith.

Guide housing 1110 and elongated guide shaft 1120 of guide member 1100 may be configured similar to any of the embodiments detailed above. That is, elongated guide shaft 1120 and/or guide housing 1110 may define lumens extending therethrough of any suitable configuration for routing a suture passer through guide member 1100, cannula 100, and tissue, similarly as detailed above. Guide housing 1110 further includes engagement tabs 1117 extending therefrom that are configured for releasable engagement within the radially opposed apertures 111 defined though proximal housing component 110a of housing 110 of cannula 100 (see FIGS. 4A and 4B) to permit releasable engagement and alignment of guide member 1100 with cannula 100, similarly as detailed above. Alternatively, guide housing 1110 may include bayonet fitting configured to engage base member 102b of cannula 100 (with housing 110 removed therefrom), as also detailed above. As these features are detailed above with respect to the other embodiments of guide members, they will not be repeated below.

Referring to FIG. 29, cleaning member 1130 is generally annular in shape and, as mentioned above, is positioned about elongated guide shaft 1120 towards the distal end thereof. Cleaning member 1130 may be formed from any suitable resiliently compressible material, e.g., biocompatible foam, and defines a bulbous configuration such that cleaning member 1130 bulges radially outwardly from the outer annular surface of elongated guide shaft 1120. Cleaning member 1130 defines a maximum diameter, in its at-rest position, that is greater than the diameter of longitudinal passageway 105 of elongated tubular member 102a of cannula 100 (see FIG. 30B). Cleaning member 1130 is resiliently compressible from this at-rest position to a compressed position, wherein cleaning member 1130 defines a minimum diameter that is less than or equal to the diameter of longitudinal passageway 105 of elongated tubular member 102a of cannula 100 (see FIG. 30B).

Figure 30A:
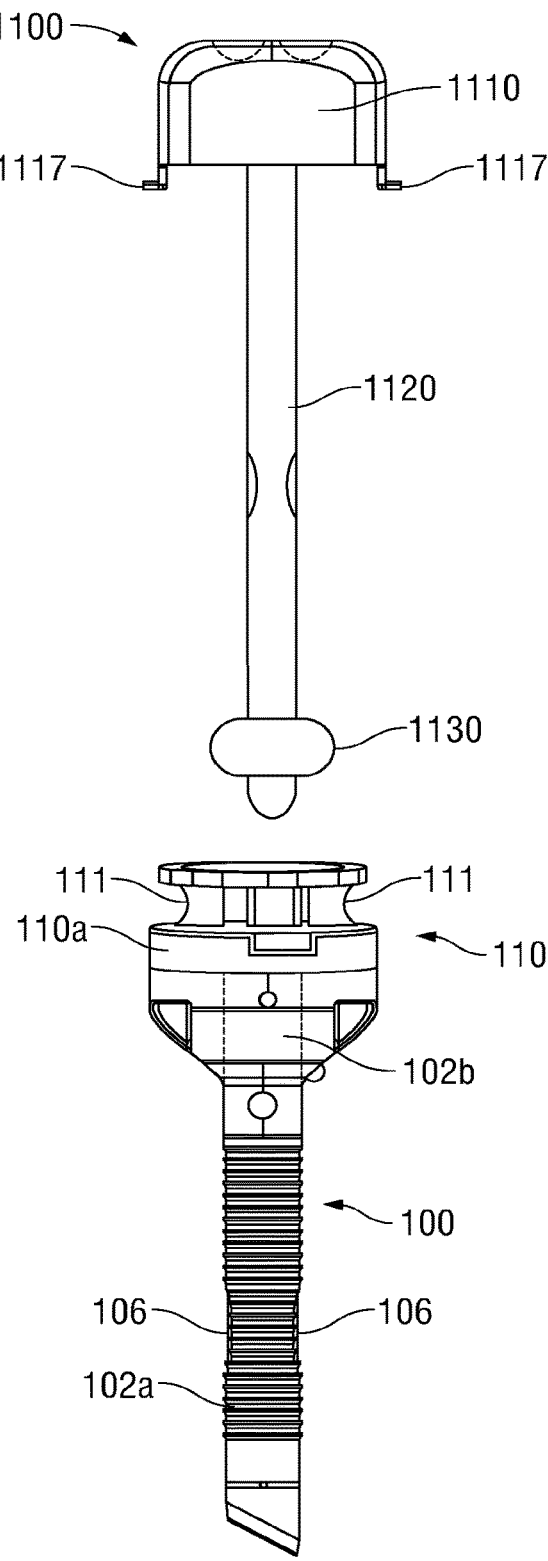
FIG. 30A is a side view of the guide member of FIG. 29 positioned for insertion into the cannula of FIG. 4A.

With reference to FIGS. 30A and 30B, in use, guide member 1100 is inserted through longitudinal passageway 105 of elongated tubular member 102a of cannula 100, similarly as detailed above with respect to the previous guide members. As guide member 1100 is initially inserted through longitudinal passageway 105 of elongated tubular member 102, cleaning member 1130 is sufficiently compressed to permit insertion through longitudinal passageway 105 while also being resiliently biased into contact with the interior surface of elongated tubular member 102a that surrounds longitudinal passageway 105. As a result, during insertion, cleaning member 1130 wipes the interior surface of elongated tubular member 102a to remove fluids, debris, tissue, etc. therefrom. In addition to being resiliently compressible, cleaning member 1130 may further be absorbent and/or may otherwise be configured to facilitate wiping and cleaning the interior surface of elongated tubular member 102a during translation of guide member 1100 therethrough.

It is envisioned that guide member 1100 be inserted through and/or reciprocated relative to elongated tubular member 102a of cannula 100 to clean the interior surface of elongated tubular member 102a before, during, and/or after a surgical procedure, as required. In particular, cleaning elongated tubular member 102a may be advantageous prior to insertion of an endoscope (not shown) or other device where fluids, debris, tissue, etc. may affect the performance thereof. In addition to cleaning elongated tubular member 102a of cannula 100 without requiring the removal of cannula 100 from the opening in tissue, guide member 1100 may also be utilized to facilitate closure of the opening in tissue, once the surgical procedure is complete.

Referring to FIG. 30C, for use in facilitating closure of the opening in tissue, guide member 1100 is inserted into elongated tubular member 102a of cannula 100 until both the distal end of elongated guide shaft 1120 and cleaning member 1130 emerge from the distal end of cannula 100 and engagement tabs 1117 are engaged with apertures 111 to engage and align guide member 1100 with cannula 100. In this fully inserted position, cleaning member 1130 serves as a proximal stop to ensure proper positioning of cannula 100 and guide member 1100 within the opening in tissue. More specifically, the at-rest diameter of cleaning member 1130 is sufficiently large relative to the opening in tissue such that cleaning member 1130 abuts the internal surface of tissue surrounding the opening in tissue. This abutment serves as a proximal stop member to inhibit further proximal movement of cannula 100 and guide member 1100 relative to tissue, thus ensuring proper positioning of cannula and guide member 1100 relative to tissue during suturing.

Once cannula 100 and guide member 1100 are properly positioned as detailed above, a suture passer may be inserted through guide member 1100, cannula 100, and tissue, on both sides of the opening in tissue, to pass a suture therethrough and enable tying off of the suture to close the opening in tissue, similarly as detailed above with respect to any of the previous embodiments.

Turning to FIGS. 31A-37B, various configurations and methods provided in accordance with the present disclosure that facilitate the manufacture and/or assembly of the guide members are described. Although detailed with reference to exemplary guide members, the configurations and methods detailed hereinbelow are equally applicable for use with any of the guide members detailed above. That is, any of the guide members detailed above may be manufactured and/or assembled similarly as detailed below.

Referring to FIGS. 31A and 31B, guide member 1200 is formed from three components: an outer sleeve 1210, an inner shaft 1220, and a cap 1230. Outer sleeve 1210 defines a hollow, generally tubular configuration including a pair of opposed, elongated slots 1212 extending through the peripheral wall of outer sleeve 1210. Slots 1212 provide access to the hollow interior of outer sleeve 1210 from the outer periphery thereof. Outer sleeve 1210 further includes a distal aperture 1214 defined at the distal end of outer sleeve 1210, and a collar 1215 disposed at the proximal end of outer sleeve 1210. Collar 1215 includes a pair of opposed, resilient fingers 1216 each having a free end 1217, and a transverse cut-out 1218 having a pair of opposed engagement recesses 1219.

Inner shaft 1220 of guide member 1200 includes an elongated body 1222, a head 1225 disposed at the proximal end of elongated body 1222, and a tip 1229 extending from the distal end of elongated body 1222. Elongated body 1222 defines a plate-like configuration and is configured for insertion into slots 1212 and the hollow interior of outer sleeve 1210 such that the narrow edges of elongated body 1222 form a portion of the outer peripheral surface of guide member 1200. Elongated body 1222 further includes channels 1224 defined within and extending along the wide edges of elongated body 1222. When inner shaft 1220 is engaged within outer sleeve 1210, elongated body 1222 of inner shaft 1220 and the interior surface of outer sleeve 1210 cooperate to enclose channels 1224 to form guide lumens configured to receive a suture passer, similarly as detailed above. The distal ends of channels 1224 are defined through the narrow edges of elongated body 1222 such that a suture passer inserted through channels 1224 exits the outer peripheral surface of guide member 1200 to pass through tissue surrounding the opening in tissue, similarly as detailed above. Channels 1224 may be formed in any suitable configuration, e.g., straight, curved, etc., to achieve a guide lumen having a particular configuration (such as any of those detailed above). Further, since channels 1224 are disposed on opposite sides of elongated body 1222, elongated body 1222 serves as a barrier to separate the guide lumens such that the guide lumens may crossover one another without intersecting.

Continuing with reference to FIGS. 31A and 31B, as mentioned above, head 1225 of inner shaft 1220 is disposed at the proximal end of elongated body 1222 and is configured for at least partial receipt within cut-out 1218 of collar 1215 of outer sleeve 1210. Head 1225 includes a pair of guide lumen apertures 1226 defined therethrough that cooperate with channels 1224 of elongated body 1222 to enable insertion of a suture passer through apertures 1226 and into channels 1224. Head 1225 further includes a pair of resilient arms 1227 extending distally therefrom adjacent the short edges of elongated body 1222. Each resilient arm 1227 includes an engagement protrusion 1228 configured for snap-fit engagement within engagement recesses 1219 of collar 1215 of outer sleeve 1210 to engage inner shaft 1220 and outer sleeve 1210 to one another. Tip 1229 of inner shaft 1220 is configured for insertion through distal aperture 1214 of outer sleeve 1210 and to extend therefrom, as shown in FIG. 31B. Tip 1229 may define a blunt configuration or may define a sharpened configuration, depending on a particular purpose.

Cap 1230 of guide member 1200 includes a base 1232 defining a lumen 1233 extending longitudinally therethrough. Base 1232 has a pair of tabs 1234 extending distally therefrom, defines a pair of opposed grasping recesses 1236, and defines a proximal slot 1238 in communication with lumen 1233. Tabs 1234 of base 1232 are configured for releasable engagement within the radially opposed apertures 111 defined though proximal housing component 110a of housing 110 of cannula 100 (see FIGS. 4A and 4B), or other suitable cannula, to permit releasable engagement and alignment of guide member 1200 with cannula 100 (FIGS. 4A and 4B), similarly as detailed above.

Grasping recesses 1236 of base 1232 of cap 1230 are configured to facilitate the grasping and manipulation of guide member 1200 once assembled. Base member 1232 further includes a transverse aperture 1237 extending therethrough in the vicinity of each of grasping recess 1236, although other positions for transverse apertures 1237 are also contemplated. Transverse apertures 1237 are configured to receive free ends 1217 of resilient fingers 1216 in snap-fit engagement to engage cap 1230 and outer sleeve 1210 to one another. Proximal slot 1238 of base 1232 of cap 1230 is configured to receive head 1225 of inner shaft 1220 therein.

Referring still to FIGS. 31A and 31B, in order to assemble guide member 1200, inner shaft 1220, lead by tip 1229, is inserted into the proximal end of outer sleeve 1210 and translated distally through the hollow interior of outer sleeve 1210 until engagement protrusions 1228 of resilient arms 1227 of head 1225 of inner shaft 1220 are biased into snap-fit engagement with engagement recesses 1219 of collar 1215 of outer sleeve 1210 to engage inner shaft 1220 and outer sleeve 1210 to one another. In this position, as mentioned above, tip 1229 extends distally from outer sleeve 1210, and the narrow edges of elongated body 1222 of inner shaft 1220 form a portion of the outer peripheral surface of guide member 1200 by occupying slots 1212. Once outer sleeve 1210 and inner shaft 1220 are engaged with one another, or prior thereto, cap 1230 is slid over the distal end of outer sleeve 1210 and translated proximally about outer sleeve 1210 until free ends 1217 of resilient fingers 1216 of outer sleeve 1210 are biased into snap-fit engagement with transverse apertures 1237 of cap 1230 to engage cap 1230 and outer sleeve 1210 with one another.

With both inner shaft 1220 and cap 1230 engaged with outer sleeve 1210 as detailed above, guide member 1200 is ready for use. In order to disassemble guide member 1200, cap 1230 is squeezed inwardly at grasping recesses 1236 to disengage free ends 1217 of resilient fingers 1216 of outer sleeve 1210 from transverse apertures 1237 of cap 1230, thus allowing cap 1230 to be slid distally about and ultimately removed from outer sleeve 1210. Thereafter, resilient arms 1227 of head 1225 of inner shaft 1220 are squeezed inwardly at a position proximal of engagement protrusions 1228 to disengage engagement protrusions 1228 from engagement recesses 1219 of collar 1215 of outer sleeve 1210, thus allowing inner shaft 1220 to be withdrawn proximally from outer sleeve 1210. However, in other embodiments, guide member 1200 may be configured as a disposable component that resists disassembly.

Outer sleeve 1210, inner shaft 1220, and cap 1230 of guide member 1200 may be formed from any suitable material, e.g., biocompatible polymers, via any suitable manufacturing process. Forming guide member 1200 from these three components facilitates manufacturing in that each component may be made in relatively simple fashion; that is, the relatively complex processes required to form the features of guide member 1200 on a single component are obviated. Outer sleeve 1210, inner shaft 1220, and/or cap 1230 may be configured as disposable components, or may be configured to be sterilized for re-use. With respect to embodiments where one or more of outer sleeve 1210, inner shaft 1220, and cap 1230 are sterilizable for re-use, forming guide member 1200 from these releasable components facilitates the cleaning and sterilization of each component.

With reference to FIGS. 32A and 32B, guide member 1300 is formed from three components: an outer sleeve 1310, an inner shaft 1320 having a cap 1330, and a ring 1340. Outer sleeve 1310 is similar to outer sleeve 1210 of guide member 1200 (see FIGS. 31A and 31B) and defines a hollow, generally tubular configuration including a pair of opposed, elongated slots 1312 extending through the peripheral wall of outer sleeve 1310 and a distal aperture 1314 defined at the distal end of outer sleeve 1310. However, outer sleeve 1310 differs from outer sleeve 1210 (see FIGS. 31A-31B) in that collar 1315 of outer sleeve 1310 simply defines an annular, ring-like configuration disposed about the proximal end of the body of outer sleeve 1310.

Inner shaft 1320 of guide member 1300 includes an elongated body 1322, a cap 1330 disposed at the proximal end of elongated body 1322, and an engagement member 1329 extending from the distal end of elongated body 1322. Elongated body 1322 of inner shaft 1320 is similar to elongated body 1222 of inner shaft 1220 of guide member 1200 (see FIGS. 31A and 31B), defines a plate-like configuration, and includes channels 1324 that cooperate with outer sleeve 1310 to define the guide lumens of guide member 1300.

Cap 1330 of inner shaft 1320 includes a base 1332 and a pair of arms 1334 extending distally from base 1332. Each arm 1334 includes an engagement protrusion 1336 disposed at the free end of the respective arm 1334 and extending outwardly therefrom. Base 1332 of cap 1330 includes a pair of guide lumen apertures 1338 defined therethrough that cooperate with channels 1324 of elongated body 1322 to enable insertion of a suture passer through cap 1330 and into channels 1324.

As shown in FIG. 32B, engagement member 1329 of inner shaft 1320 includes a rod 1329a extending distally from elongated body 1322 of inner shaft 1320 and a tip member 1329b disposed at a free end of rod 1329a. As such, tip member 1329b is spaced-apart from the distal end of elongated body 1322. Tip member 1329b is bifurcated to form a pair of resiliently flexible components (or may otherwise be configured to be resiliently flexible) and defines a frusto-conical or other tapered configuration. As such, a proximally-facing shoulder 1329c is formed at the interface between rod 1329a and tip member 1329b. Rod 1329a is dimensioned to at least partially pass through distal aperture 1314 of outer sleeve 1310, while at least a portion of tip member 1329b defines an at-rest diameter that is greater than the diameter of distal aperture 1314. Thus, as inner shaft 1320 is inserted through outer sleeve 1310 and tip member 1329b is urged into distal aperture 1314, tip member 1329b is resiliently compressed to permit passage through distal aperture 1314. Once tip member 1329b fully passes through distal aperture 1314, tip member 1329b resiliently returns to its at-rest position, wherein proximal withdrawal of tip member 1329b through distal apertures 1314 is inhibited via shoulder 1329c and, thus, outer sleeve 1310 and inner shaft 1320 are retained in engagement with one another.

Referring again to FIGS. 32A and 32B, ring 1340 of guide member 1300 defines a longitudinal bore 1342 and includes a helical track 1344 formed on the inwardly-facing surface that defines longitudinal bore 1344. Helical track 1344 is configured to receive engagement protrusions 1336 of arms 1334 of cap 1330 of inner shaft 1320 upon relative rotation of proximal ring 1340 and inner shaft 1320 to engage proximal ring 1340 and inner shaft 1320 to one another via bayonet coupling. Longitudinal bore 1342 of ring 1340 defines a diameter greater than that of the tubular body of outer sleeve 1310 but less than that of collar 1315 such that, upon engagement of ring 1340 and inner shaft 1320 to one another, collar 1315 is retained therebetween to fix ring 1340 in position relative to outer sleeve 1310. Ring 1340 further includes a pair of tabs 1346 extending distally therefrom. Tabs 1346 are configured for releasable engagement within the radially opposed apertures 111 defined though proximal housing component 110a of housing 110 of cannula 100 (see FIGS. 4A and 4B), or other suitable cannula, to permit releasable engagement and alignment of guide member 1300 with cannula 100 (FIGS. 4A and 4B), similarly as detailed above.

In order to assemble guide member 1300, inner shaft 1320, lead by engagement member 1329, is inserted into the proximal end of outer sleeve 1310 and urged distally through the hollow interior of outer sleeve 1310 until tip member 1329b fully passes through distal aperture 1314 and is resiliently returned to its at-rest position, thereby engaging outer sleeve 1310 and inner shaft 1320 with one another. Thereafter, ring 1340 is slid over the distal end of outer sleeve 1310 and translated proximally about outer sleeve 1310 until engagement protrusions 1336 of arms 1334 of cap 1330 of inner shaft 1320 are positioned within longitudinal bore 1342 of ring 1340 adjacent helical track 1344. Once this position has been achieved, ring 1340 is rotated relative to inner shaft 1320 such that engagement protrusions 1336 are translated along helical track 1344 sufficiently so as to engage ring 1340 and inner shaft 1320 to one another via bayonet coupling.

Guide member 1300 may be disassembled via first rotating ring 1340 relative to inner shaft 1320 in the opposite direction to disengage and ultimately remove ring 1340. Thereafter, tip member 1329b of inner shaft 1320 may be squeezed inwardly and urged proximally relative to outer sleeve 1310 sufficiently so as to disengage tip member 1329b from aperture 1314 of outer sleeve 1310. Alternatively, guide member 1300 may be configured as a disposable component that resists disassembly. Guide member 1300 may be formed from similar materials and provides similar advantages to those detailed above with respect to guide member 1200 (FIGS. 31A and 31B).

Guide member 1400, shown in FIGS. 33A and 33B, is similar to guide member 1300 (FIGS. 32A and 32B) and includes an outer sleeve 1410, an inner shaft 1420 having a cap 1430, and a ring 1440. However, guide member 1400 differs from guide member 1300 (FIGS. 32A and 32B) in that guide member 1400 is formed from two components, while guide member 1300 (FIGS. 32A and 32B) is formed from three components. More specifically, ring 1440 of guide member 1400 is integrally formed or permanently affixed about outer sleeve 1410 at the proximal end of outer sleeve 1410. To assembly guide member 1400, inner shaft 1420 is inserted distally into outer sleeve 1410 sufficiently so as to urge tip member 1429 through aperture 1415 such that tip member 1429 resiliently returns to its at-rest position to engage outer sleeve 1410 and inner shaft 1420 to one another. As ring 1440 is formed with or fixed to outer sleeve 1410, ring 1440 need not be separately engaged to inner shaft 1420. Guide member 1400 is otherwise similar to guide member 1300 (FIGS. 32A and 32B) and may include any or all of the features thereof.

Referring to FIGS. 34A and 34B, guide member 1500 is integrally formed in two stages: first, tubes 1510, 1520 are formed, separately or together, via any suitable process, e.g., casting, welding, injection molding, etc. Tubes 1510, 1520 may be formed from a metal, e.g., stainless steel, or other suitable material. Tubes 1510, 1520 includes lumens 1512, 1522, respectively, extending therethrough that serve as the guide lumens of guide member 1500. As such, tubes 1510, 1520 may define any suitable individual configuration, e.g., straight or curved, and may be disposed in any suitable configuration relative to one another, e.g., side-by-side or overlapping (once or multiple times), to achieve a desired configuration of the guide lumens of guide member 1500 (such as any of those detailed above). Once tubes 1510, 1520 are formed, guide housing 1540 is over-molded or otherwise formed about tubes 1510, 1520 to from the complete guide member 1500. Guide housing 1540 is formed from a biocompatible polymer, or other suitable material, and may include any of the features of any of the guide members detailed above. Over-molding guide housing 1540 about tubes 1510, 1520 is advantageous in that it obviates the need to form the guide lumens within guide housing 1540, which may require complex manufacturing processes. Rather, tubes 1510, 1520 serve as an insert that defines lumens 1512, 1522, which function as the guide lumens of guide member 1500, while guide housing 1540 is simply formed about tubes 1510, 1520 to a desired configuration.

Figure 35:
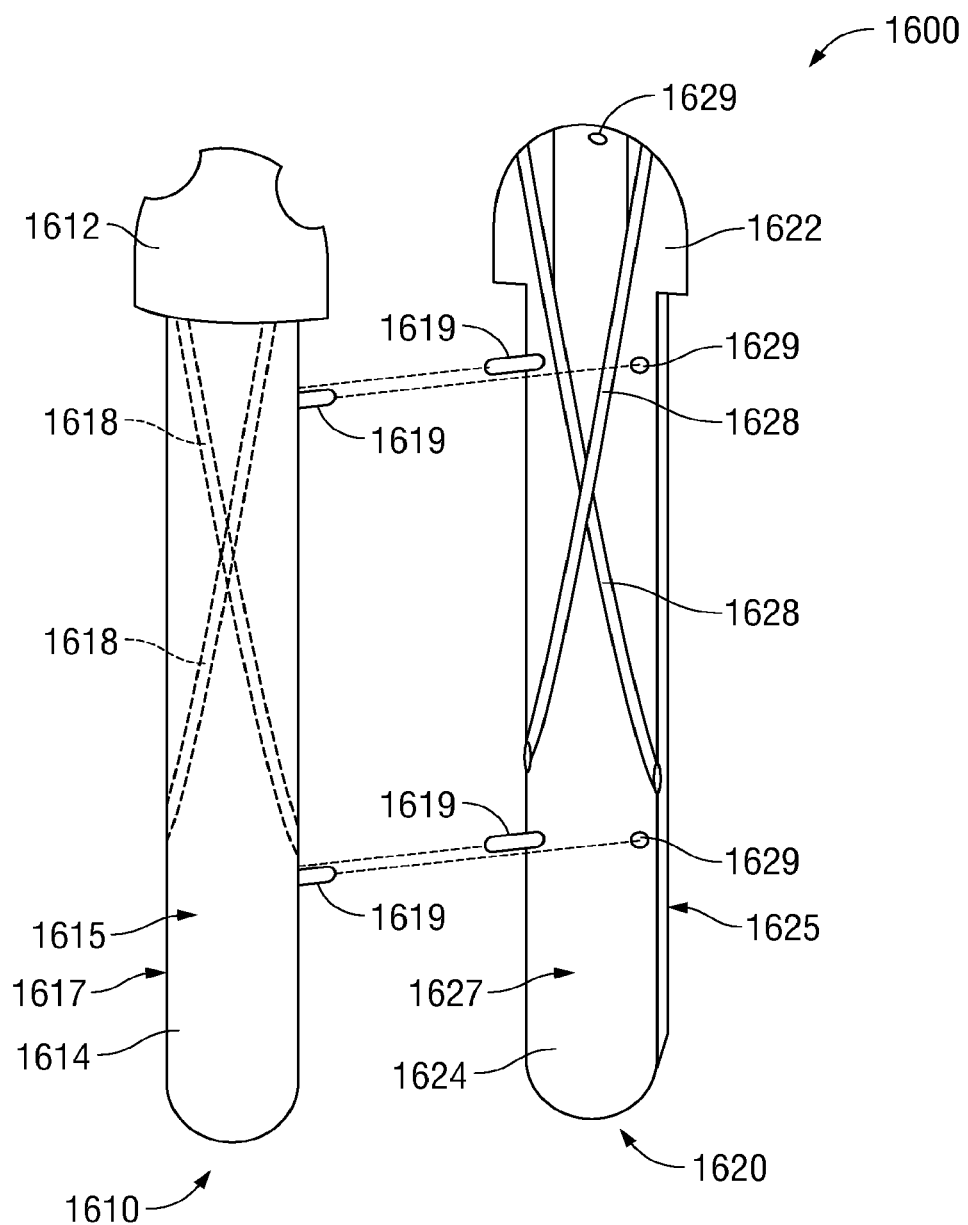
FIG. 35 is an exploded, perspective view of another guide member provided in accordance with the present disclosure.

With reference to FIG. 35, guide member 1600 is formed from two components 1610, 1620. Components 1610, 1620 may each form half of guide member 1600 or may define unequal portions thereof. Each component 1610, 1620 includes a head portion 1612, 1622 and a shaft portion 1614, 1624 extending distally from the head portion 1612, 1622. Further, each component 1610, 1620 includes a semi-annular surface 1615, 1625 and a planar surface 1617, 1627. Planar surfaces 1617, 1627 are configured to mate with one another upon engagement of components 1610, 1620 with one another, while semi-annular surfaces 1615, 1625 cooperate to define the generally circular tubular exterior surface of guide member 1600 upon engagement of components 1610, 1620 with one another.

Each component 1610, 1620 of guide member 1600 includes one or more channels 1618, 1628 defined within planar surfaces 1617, 1627 thereof and extending from head portions 1612, 1622 at least partially through shaft portions 1614, 1624. When components 1610, 1620 are engaged with one another, channels 1618, 1628 cooperate to form guide lumens configured to receive a suture passer, similarly as detailed above. The distal ends of channels 1618, 1628 are defined through semi-annular surfaces 1615, 1625 such that a suture passer inserted through channels 1618, 1628 exits the outer peripheral surface of guide member 1600, similarly as detailed above. Channels 1618, 1628 may be formed in any suitable configuration, e.g., straight, curved, etc., to achieve a guide lumen having a particular configuration (such as any of those detailed above).

Continuing with reference to FIG. 35, each component 1610, 1620 of guide member 1600 includes one or more posts 1619 extending from and/or one or more lumens 1629 defined within the planar surface 1617, 1627 thereof. Posts 1619 are configured for receipt within corresponding lumens 1629 to secure components 1610, 1620 to one another. Corresponding posts 1619 and lumens 1629 are aligned with one another such that, upon engagement of components 1610, 1620 with one another, guide member 1600 is fully formed wherein channels 1618, 1628 cooperate to form the guide lumens extending through guide member 1600.

Referring to FIGS. 36A and 36B, another guide member 1700 provided in accordance with the present disclosure is formed from an outer sleeve 1710 and an inner shaft 1730. In some embodiments, guide member 1700 may further include an O-ring 1740, as detailed below. Outer sleeve 1710 defines a hollow, generally tubular configuration including a pair of opposed arms 1712 disposed towards the proximal end of outer sleeve 1710 and extending radially outwardly from outer sleeve 1710. Arms 1712 of sleeve 1710 include tabs 1714 disposed at the free ends thereof that are configured for releasable engagement within the radially opposed apertures 111 defined though proximal housing component 110*a* of housing 110 of cannula 100 (see FIGS. 4A and 4B), or other suitable cannula, to permit releasable engagement and alignment of guide member 1700 with cannula 100 (FIGS. 4A and 4B), similarly as detailed above. Outer sleeve 1710 further includes a pair of slots 1718 (only one of which is shown) defined therethrough towards the proximal end thereof that provides access to the hollow interior of outer sleeve 1710 from the outer periphery thereof. A pair of opposed protrusions 1720 (only one of which is shown) is disposed on the interior surface of outer sleeve 1710 and extends radially inwardly into the hollow interior of outer sleeve 1710.

Inner shaft 1730 of guide member 1700 defines a pair of opposed recessed tracks 1732 (only one of which is shown) within the exterior annular surface of inner shaft 1730 towards the proximal end thereof. Tracks 1732 each include a longitudinal portion 1733 and a transverse portion 1734 disposed substantially normal to the longitudinal portion 1733, although other configurations are also contemplated. A retention rib 1735 is disposed within the transverse portion 1734 of each track 1732 towards the closed end thereof, i.e., opposite the interconnection between the longitudinal portion 1733 and the transverse portion 1734. As detailed below, tracks 1732 are configured to receive and retain protrusions 1720 to secure outer sleeve 1710 about inner shaft 1730. Inner shaft 1730 further defines an elongated channel 1736 extending along inner shaft 1730. Channel 1736 is defined completely through inner shaft 1730 such that a suture passer may be inserted through either opposed side of inner shaft 1730 and exit the same or opposite side of inner shaft 1730. In embodiments where O-ring 1740 is provided, inner shaft 1730 may define an annular recess 1742 towards the distal end thereof that is configured to receive and retain O-ring 1740 therein.

Continuing with reference to FIGS. 36A and 36B, the assembly of guide member 1700 is detailed. Initially, outer sleeve 1710 is slid over inner shaft 1730 and translated distally about inner shaft 1730 until protrusions 1720 of outer sleeve 1710 are received within longitudinal portions 1733 of tracks 1732. Once this position has been achieved, outer sleeve 1710 is rotated relative to inner shaft 1730 such that protrusions 1720 are translated along transverse portions 1734 of tracks 1732. Under sufficient rotational urging of outer sleeve 1710 relative to inner shaft 1730, protrusions 1720 traverse retention ribs 1735 and are seated at the closed ends of transverse portions 1734 of tracks 1732, thereby securing outer sleeve 1710 and inner shaft 1730 relative to one another in fixed translational and rotational orientation. In this secured position of outer sleeve 1710 and inner shaft 1730, slots 1718 of outer sleeve 1710 are aligned with channel 1736 of inner shaft 1730 to permit passage of a suture passer into either of slots 1718, through guide member 1700, and out the distal end of channel 1736 on either side thereof. As shown in FIG. 36B, a distal portion of channel 1736 is exposed, i.e., uncovered via outer sleeve 1710, when outer sleeve 1710 is secured about inner shaft 1730, to permit the suture passer to exit guide member 1700 via the distal portion of channel 1736.

Once outer sleeve 1710 has been secured about inner shaft 1730, or prior thereto, O-ring 1740 is resiliently expanded and slid over the distal end of inner shaft 1730 into position about annular recess 1742. Once positioned about annular recess 1742, O-ring 1740 is resiliently returned towards is at-rest position, thereby retaining O-ring 1740 at least partially within annular recess 1742. In use, O-ring 1740 helps establish a seal between guide member 1700 and the cannula, e.g., cannula 100 (see FIGS. 4A and 4B) through which guide member 1700 is inserted, thereby helping to maintain the internal surgical site in an insufflated condition. As opposed to an O-ring 1740, a resilient sleeve, or other suitable sealing member, may be provided for similar purposes. Although detailed with respect to guide member 1700, the O-ring 1740 (or other sealing member) may similarly be provided for use with any of the other guide members detailed herein. Further, instead of providing the O-ring 1740 (or other sealing member) on guide member 1700, such may alternatively be provided on an interior surface of the cannula, e.g., cannula 100 (see FIGS. 4A and 4B). Other features provided to establish a seal between the guide member and cannula to help maintain the internal surgical site in an insufflated condition are detailed below.

Turning to FIGS. 37A and 37B, guide member 1800 includes an outer sleeve 1810 and an inner shaft 1820. Outer sleeve 1810 defines a hollow, generally tubular configuration and includes a pair of opposed, arch-shaped cut-outs 1812 towards the distal end thereof that define a pair of opposed fingers 1814 therebetween. Each finger 1814 includes an inwardly-extending protrusion 1815 disposed towards the free end thereof (although fingers 1814 may alternatively define apertures towards the free ends thereof).

Inner shaft 1820 of guide member 1800 includes an elongated body 1822 and a head 1824 disposed at the proximal end of elongated body 1822. Head 1824 and elongated body 1822 cooperate to define a pair of opposed channels 1825 (only one of which is shown) extending longitudinally from the proximal end towards the distal end of inner shaft 1820. Channels 1825 terminate prior to reaching distal cap 1830 of inner shaft 1820. Inner shaft 1820 further includes a pair of opposed recesses 1828 (only one of which is shown) defined within elongated body 1822 towards the distal end of elongated body 1822. Alternatively, instead of recesses 1828, protrusions may be provided. Head 1824 of inner shaft 1820 includes a pair of tabs 1829 configured for releasable engagement within the radially opposed apertures 111 defined though proximal housing component 110a of housing 110 of cannula 100 (see FIGS. 4A and 4B), or other suitable cannula, to permit releasable engagement and alignment of guide member 1800 with cannula 100 (FIGS. 4A and 4B), similarly as detailed above.

Continuing with reference to FIGS. 37A and 37B, the assembly of guide member 1800 is detailed. Initially, outer sleeve 1810 is slid over elongated body 1822 of inner shaft 1820 and translated proximally about inner shaft 1820 until the proximal end of outer sleeve 1810 is positioned adjacent to or abuts head 1824 of inner shaft 1820. Once this position has been achieved, prior thereto, or concurrently with the advancement of outer sleeve 1810 about elongated body 1822, outer sleeve 1810 and elongated body 1822 are rotationally aligned with one another such that protrusions 1815 are aligned with recesses 1828. Accordingly, upon positioning outer sleeve 1810 about elongated body 1822 as detailed above, protrusions 1815 are received within recesses 1828 to secure outer sleeve 1810 about elongated body 1822 of inner shaft 1820. In this assembled condition, outer sleeve 1810 encloses channels 1825 such that channels 1825 form the guide lumens of guide member 1800. With particular reference to FIG. 37B, a distal portion of each channel 1825 is exposed, i.e., uncovered via outer sleeve 1810, when outer sleeve 1810 is secured about inner shaft 1820, thus permitting a suture passer to exit the guide lumens of guide member 1800 through the exposed portions of channels 1825.

With respect to any of the embodiments of guide members detail herein, the various components thereof may be formed from any suitable process, e.g., injection molding machining, extruding, 3D printing, Direct Metal Laser Sintering (DMLS), etc., and may be formed from any suitable materials, e.g., plastics, metals, combinations thereof, etc.

Figure 37C:
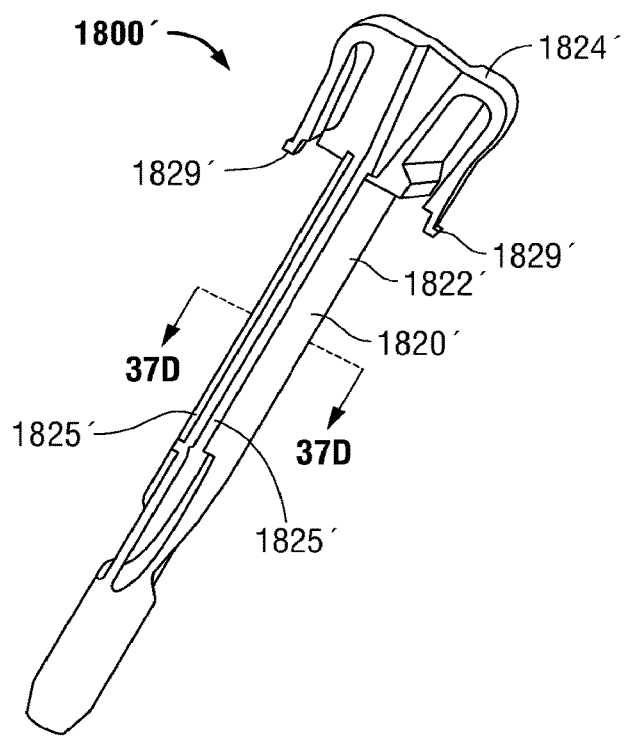
FIG. 37C is a perspective view of another guide member provided in accordance with the present disclosure.
Figure 37D:
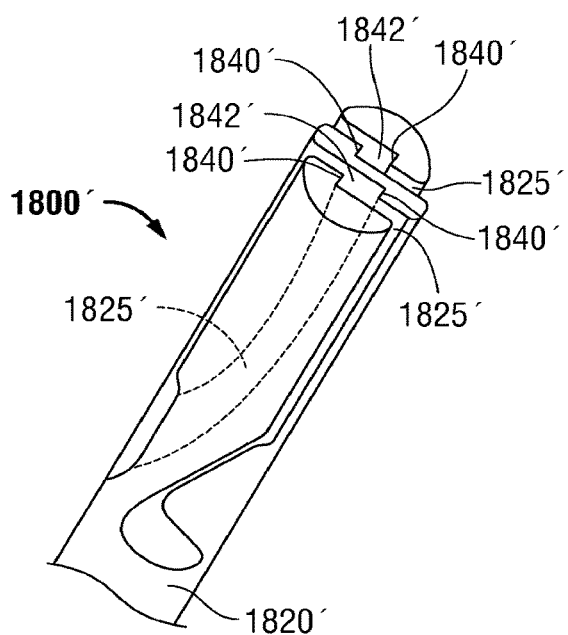
FIG. 37D is a perspective, cross-sectional view of the guide member of FIG. 37C taken along section line 37D-37D of FIG. 37C.
Figure 37E:
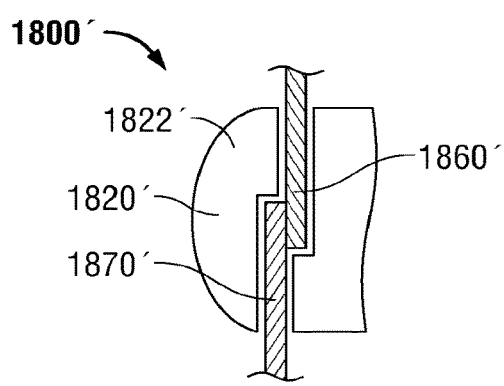
FIG. 37E is a transverse, cross-sectional view of the guide member of FIG. 37C illustrating molding plates utilized to facilitate formation of the guide member.

FIGS. 37C-37E illustrate another embodiment of a guide member 1800' provided in accordance with the present disclosure. Guide member 1800' is similar to guide member 1800 (FIGS. 37A and 37B) in that guide member 1800' includes a shaft 1820' having an elongated body 1822' and a head 1824' disposed at the proximal end of elongated body 1822'. Head 1824' and elongated body 1822' cooperate to define a pair of channels 1825' extending longitudinally from the proximal end towards the distal end of shaft 1820' on either side of shaft 1820'. Head 1824' of shaft 1820' includes a pair of tabs 1829' configured for releasable engagement within the radially opposed apertures 111 defined though proximal housing component 110a of housing 110 of cannula 100 (see FIGS. 4A and 4B), or other suitable cannula, to permit releasable engagement and alignment of guide member 1800' with cannula 100 (FIGS. 4A and 4B), similarly as detailed above.

Different from guide member 1800 (FIGS. 37A and 37B), guide member 1800' need not include an outer sleeve, but rather, includes features defined on shaft 1820' that are configured to retain a suture passer inserted therethrough within opposed channels 1825' without the need to fully enclose channels 1825'. Specifically, with particular reference to FIG. 37D, pairs of opposed shoulders 1840' are defined within shaft 1020' adjacent channels 1825' and extend longitudinally therealong so as to define a suture passer-receiving portion 1842' within each channel 1825'. Suture passer-receiving portions 1842' are dimensioned larger than the remainder of channels 1825'. As can be appreciated, as a result of this configuration, upon insertion of a suture passer into one of the channels 1825', the suture passer is inhibited from exiting the suture passer-receiving portion 1842' and, thus, is retained within the channel 1825' during translation therethrough, ensuring that the suture passer only exits guide member 1800' via the distal end of channels 1825'.

Referring to FIG. 37E, in conjunction with FIGS. 37C and 37D, to achieve the above-noted configuration of guide member 1800', guide member 1800' is formed from a monolithic piece of material via molding. In order to define each of the channels 1825' and suture passer-receiving portions 1842' thereof, separate molding plates 1860', 1870' are utilized (other portions (not shown) of molding plates 1860', 1870' and/or additional molding components (not shown) may be utilized to form the remainder of guide member 1800'). More specifically, molding plates 1860', 1870' (or the relevant portions thereof) are positioned so as to partially overlap and abut one another. As a result of this configuration, during formation of guide member 1800', the overlapping portions of molding plates 1860', 1870' define suture passer-receiving portion 1842', the ends of each of the molding plates 1860', 1870' together with the portion of the other molding plate 1860', 1870' extending adjacent thereto cooperate to define shoulders 1840', and the non-overlapping portions of molding plates 1860', 1870' define the remainder of channel 1825' on either side of suture passer-receiving portion 1842'.

Referring to FIGS. 38A-43B, as mentioned above, in some instances, it is desirable to maintain the internal surgical site in an insufflated state. Accordingly, the various guide members detailed below are configured to facilitate maintaining the internal surgical site in an insufflated state by sealing open lumens and/or helping to eliminate leak paths between the guide member, the cannula, e.g., cannula 100 (see FIGS. 4A and 4B) or other suitable cannula, the suture passer, and/or tissue. The guide members detailed below may incorporate any of the features of any of the guide members detailed above, and vice versa.

Figure 38A:
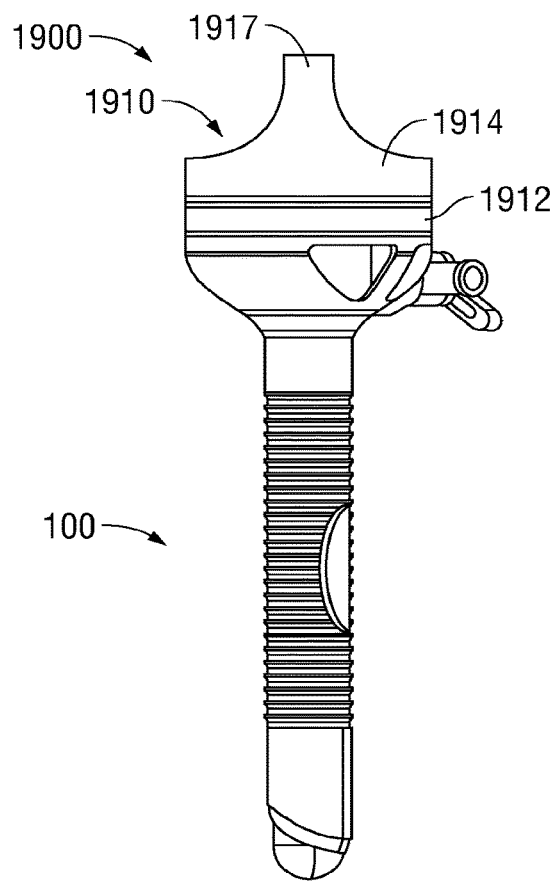
FIG. 38A is a side view of another guide member provided in accordance with the present disclosure engaged within the cannula of FIG. 4A.
Figure 38B:
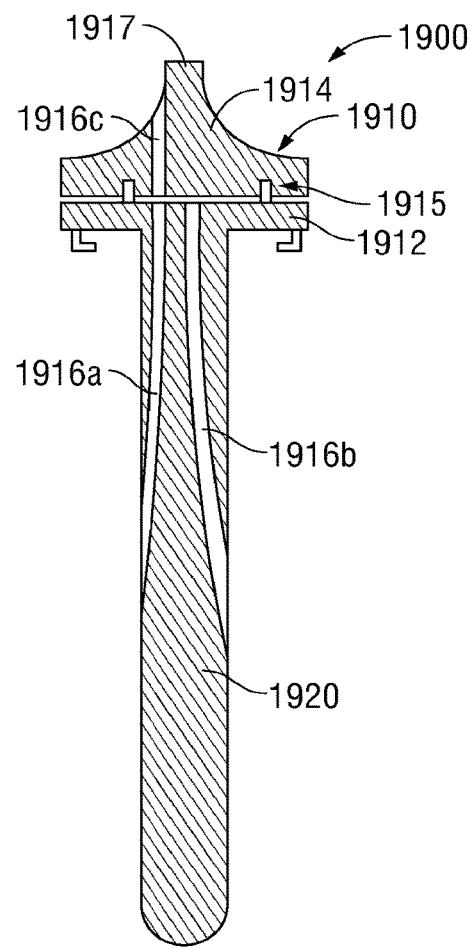
FIG. 38B is a longitudinal, cross-sectional view of guide member shown in FIG. 38A.

FIGS. 38A and 38B illustrate a guide member 1900 configured for releasable engagement with cannula 100 (or any other suitable cannula), similarly as detailed above with respect to any of the embodiments detailed herein. Guide member 1900 generally includes a guide housing 1910 disposed in mechanical cooperation with an elongated guide shaft 1920. Guide member 1900 further includes a pair of guide lumens 1916a, 1916b extending therethrough. Guide lumens 1916a, 1916b may be configured similar to any of the embodiments detailed above.

Guide housing 1910 includes a base 1912 and a head portion 1914 rotatably coupled to base 1912. Base 1912 is monolithically formed with or otherwise engaged to the proximal end of guide shaft 1920. Guide lumens 1916a, 1916b extend through base 1912 of guide housing 1910 and into guide shaft 1920. Base 1912 is configured to releasably engage housing 110 of cannula 100, similarly as any of the embodiments detailed above.

Head portion 1914 of guide housing 1910 may be rotatably coupled to base 1912 via a track and slider engagement 1915, or may be rotatably coupled to base 1912 in any other suitable fashion. Head portion 1914 may be configured to rotate 180 degrees relative to base 1912, may be configured to rotate 360 degrees relative to base 1912, or may be configured to rotate in any other suitable fashion. Head portion 1914 includes a grasping bar 1917 configured to facilitate grasping and rotating head portion 1914 relative to base 1912. Head portion 1914 further includes an entry lumen 1916c that is offset relative to a longitudinal axis of guide member 1900. Due to this offset configuration, rotation of head portion 1914 relative to base 1912 may be effected to transition guide member 1900 between a first use state, wherein entry lumen 1916c is aligned with guide lumen 1916a to permit passage of a suture passer therethrough, a second use state, wherein entry lumen 1916c is aligned with guide lumen 1916b to permit passage of a suture passer therethrough, and a sealed state, wherein entry lumen 1916 is offset relative to both guide lumens 1916a, 1916b.

A sealing gasket (not shown) may be disposed on the distally-facing surface of head portion 1914 between base 1912 and head portion 1914 to seal lumens 1916a, 1916b when entry lumen 1916c is not aligned therewith. When entry lumen 1916c is aligned with one of the guide lumens 1916a, 1916b, the sealing gasket (not shown) does not provide a seal but, rather, inserting a suture passer through entry lumen 1916c and the aligned guide lumen 1916a, 1916b seals the passage defined therethrough. More specifically, O-rings, resilient sleeves, the sealing gasket, or other suitable sealing features may be provided on the suture passer or within lumens 1916a, 1916b to establish a seal with the suture passer inserted therethrough.

Turning to FIGS. 39A and 39B, another guide member 2000 configured for releasable engagement with cannula 100 (or any other suitable cannula), similarly as detailed above with respect to any of the embodiments of guide members detailed herein, is provided. Guide member 2000 generally includes a guide housing 2010 disposed in mechanical cooperation with an elongated guide shaft 2020. Guide member 2000 further includes a guide lumen 2016 extending therethrough. Guide lumen 2016 may be configured similar to any of the embodiments detailed above.

Guide housing 2010 includes a head portion 2014 and a collar 2015. Head portion 2014 is monolithically formed with or otherwise engaged to the proximal end of guide shaft 2020. Collar 2015 is disposed about guide shaft 2020 towards the proximal end thereof and is rotatably coupled to head portion 2014. Collar 2015 is configured to releasably engage housing 110 of cannula 100, similarly as any of the embodiments detailed above. Head portion 2014 may be rotatably coupled to collar 2015 via a track and slider engagement 2018, or may be rotatably coupled to collar 2015 in any other suitable fashion. Head portion 2014 may be configured to rotate 180 degrees relative to collar 2015 and cannula 100 (when guide member 2000 is engaged to cannula 100), may be configured to rotate 360 degrees relative to collar 2015 and cannula 100, or may be configured to rotate in any other suitable fashion. Head portion 2014 includes a grasping bar 2019 configured to facilitate grasping and rotating head portion 2014 relative to collar 2015 and cannula 100.

Guide shaft 2020 includes an exit aperture 2022 that communicates with guide lumen 2016 to permit a suture passer to exit guide member 2000, pass through tissue, and deposit/retrieve a portion of suture into/from the internal surgical site. As can be appreciated in view of the above, rotation of head portion 2014 relative to collar 2015 and cannula 100 also rotates guide shaft 2020 relative to collar 2015 and cannula 100. More specifically, head portion 2014 is rotatable relative to collar 2015 and cannula 100 between a first use state (FIG. 39B), wherein exit aperture 2022 is aligned with one of the apertures 106 defined within cannula 100 to permit passage of a suture passer therethrough, a second use state, wherein exit aperture 2022 is aligned with the other aperture 106 (not shown in FIGS. 39A and 39B) of cannula 100 to permit passage of a suture passer therethrough, and a sealed state (FIG. 39A), wherein exit aperture 2022 is offset relative to both apertures 106 of cannula 100. Any suitable sealing feature, such as any of those detailed above, may be disposed between cannula 100 and guide member 2000 to maintain a seal therebetween when exit aperture 2022 is not aligned with either of the apertures 106 of cannula 100.

Referring to FIG. 40, another embodiment of a guide member 2100 is shown including a housing 2110 and an elongated guide shaft 2120 monolithically formed with or otherwise engaged to housing 2110 and extending distally therefrom. Guide member 2100 further includes a pair of guide lumens 2116a, 2116b extending therethrough. Guide lumens 2116a, 2116b may be configured similar to any of the embodiments detailed above. A double-opening, zero-closure, elastomeric septum seal 2130 is disposed within housing 2110 with each of the openings thereof centered within one of the guide lumens 2116a, 2116b. As an alternative to a double-opening seal 2130, two separate seals may be provided. In either configuration, the seal(s) 2130 seal off guide lumens 2116a, 2116b in the absence of a suture passer inserted therethrough and establish a seal about a suture passer inserted therethrough.

FIG. 41 illustrates another embodiment of a guide member 2200 similar to guide member 2100 (FIG. 40) except that, rather than providing a septum seal 2130 (FIG. 40), guide member 2200 includes a trumpet valve assembly 2230 coupled to guide housing 2210. More specifically, guide housing 2210 defines a transverse slot 2212 that intersects the guide lumen(s) 2216 defined through guide member 2200. Trumpet valve assembly 2230 is slidably disposed within slot 2212 and includes a valve member 2232. Valve member 2232 includes an actuator 2234 that extends from slot 2212 and a valve body 2236 that is slidably disposed within slot 2212. Valve body 2212 defines a defining an aperture 2238 extending therethrough. A biasing member 2240 is disposed between the closed end of transverse slot 2212 and valve body 2236 so as to bias valve member 2232 outwardly from transverse slot 2212. Actuator 2234 is selectively depressible relative to guide housing 2212 to translate valve body 2236 against the bias of biasing member 2240 from a sealed position (FIG. 41), wherein aperture 2238 is offset from guide lumen 2216 such that valve assembly 2230 seals guide lumen 2216, and a use position, wherein apertures 2238 is aligned with guide lumen 2216 to permit passage of a suture passer therethrough. With valve body 2236 disposed in the use position, the suture passer may be inserted through valve body 2236 and actuator 2234 may thereafter be released such that valve body 2236 is biased into contact with the suture passer, thereby frictionally retaining the suture passer in position relative to guide member 2200.

With reference to FIG. 42, an exemplary guide member 2300 is shown including an elastomeric sealing cap 2320 configured for use therewith. However, although detailed with respect to exemplary guide member 2300, it is envisioned that sealing cap 2320 be configured for use with any of the guide members detailed herein.

Sealing cap 2320 defines a dome-shaped portion 2321 and an annular base portion 2322 that is configured to surround and sealingly engage guide housing 2310 of guide member 2300. Dome-shaped portion 2321 of sealing cap 2320 may be configured to be penetrated by a suture passer and form a seal therearound, or may include zero-closure slits defined therethrough that permit passage of a suture passer therethrough and form a seal therearound. In either configuration, sealing cap 2320 seals off guide lumens 2316 of guide member 2300 both in the absence of a suture passer and with a suture passer inserted through one of the guide lumens 2316. Sealing cap 2320 may be configured as a removable, disposable component. Such a configuration allows sealing cap 2320 to be removed, discarded, and replaced with another sealing cap 2320 after each use. As such, guide lumens 2316 can be re-sealed after multiple insertions/withdrawals of a suture passer by using additional sealing caps 2320.

Referring to FIGS. 43A and 43B, another guide member 2400 configured for releasable engagement with cannula 100 (or any other suitable cannula), similarly as detailed above with respect to any of the previous embodiments, is provided. Guide member 2400 generally includes an inner guide component 2410, an outer guide component 2420, and a sealing cuff 2440. Guide member 2400 further includes one or more guide lumens (not shown) extending therethrough. The guide lumens may be configured similar to any of the embodiments detailed above.

Inner guide component 2410 of guide member 2400 includes a head portion 2412 and a shaft 2414 extending distally from head portion 2412. An annular channel 2416 is defined within head portion 2414 between head portion 2412 and shaft 2414. The annular surface of head portion 2412 that defines channel 2416 includes threading 2417 disposed thereon. Shaft 2414 includes a distal end cap 2418 that had a larger diameter than the body of shaft 2414 such that a shoulder 2419 is defined at the junction between the body of shaft 2414 and distal end cap 2418 of shaft 2414.

Outer guide component 2420 of guide member 2400 includes a base portion 2422 and a sleeve 2424 extending distally from base portion 2422. Base portion 2422 is configured to releasably engage housing 110 of cannula 100, similarly as any of the embodiments detailed above. A portion 2425 of sleeve 2424 extends proximally from base portion 2422. This portion 2425 of sleeve 2424 defines threading 2427 on the exterior surface thereof that is complementary to and coupled with threading 2417 of inner guide component 2410. A lumen 2430 extending through sleeve 2424 is configured to slidably receive shaft 2414 of inner guide component 2410. The portion of sleeve 2424 extending distally from base portion 2422 defines a reduced length as compared to shaft 2414 of inner guide component 2410 such that, as shown in FIG. 43A, when shaft 2414 of inner guide component 2410 is fully inserted into lumen 2430, the distal end of sleeve 2424 is spaced-apart from distal end cap 2418 of shaft 2414 a distance "$d_1$." Due to the threaded engagement of inner and outer guide components 2410, 2420, respectively, with one another, head portion 2412 of inner guide component 2410 may be rotated in a first direction relative to base portion 2422 of outer guide component 2420 to withdraw shaft 2414 proximally from sleeve 2424, and in a second direction relative to base portion 2422 of outer guide component 2420 to insert shaft 2414 further distally into sleeve 2424. That is, head portion 2414 may be rotated relative to base portion 2422 between an insertion position and a sealed position to vary the distance between the distal end of sleeve 2424 and distal end cap 2418 of shaft 2414 from distance "$d_1$" to distance "$d_2$." The actual distances "$d_1$" and "$d_2$" may be set based upon a particular configuration of the guide member 2400, cannula 100, or other factors.

Referring still to FIGS. 43A and 43B, sealing cuff 2440 is formed from a resiliently expandable and compressible material and is positioned about shaft 2414 of inner guide component 2410 between distal end cap 2418 of shaft 2414 (adjacent shoulder 2419) and the distal end of sleeve 2324 of outer guide component 2420. As shown in FIG. 43A, in the insertion position of inner guide component 2410 relative to outer guide component 2420, wherein the distance between the distal end of sleeve 2424 and distal end cap 2418 of shaft 2414 is equal to distance "$d_1$," sealing cuff 2440 is substantially uncompressed (defining a cross-sectional width of "$w_1$") and, thus, does not protrude radially from sleeve 2424 of outer guide component 2420. Thus, in this position, guide member 2400 may be inserted into and/or removed from cannula 100.

Once guide member 2400 has been inserted into and engaged with cannula 100, inner guide component 2410 may be moved to the sealed position, e.g., via rotating head portion 2412 of inner guide component 2410 in the first direction relative to base portion 2422 of outer guide component 2420 and cannula 100, until the distance between the distal end of sleeve 2424 and distal end cap 2418 of shaft 2414 is equal to distance "$d_2$," which is less than distance "$d_1$." In this position, as shown in FIG. 43B, sealing cuff 2440 is compressed longitudinally between the distal end of sleeve 2424 and distal end cap 2418 of shaft 2414 such that at least a portion of sealing cuff 2440 protrudes radially outwardly from sleeve 2424 (defining a cross-sectional width of "$w_2$," which is greater than width "$w_1$"). The portion of sealing cuff 2440 that protrudes from sleeve 2424 is urged into the interior surface of cannula 100 to form a seal therewith, thus creating a seal between cannula 100 and guide member 2400. In order to remove guide member 2400 from cannula 100, first guide component 2410 is returned to the insertion position (FIG. 43A) such that sealing cuff 2440 is returned to its initial shape, permitting withdrawal of guide member 2400 from cannula 100.

Figure 44:
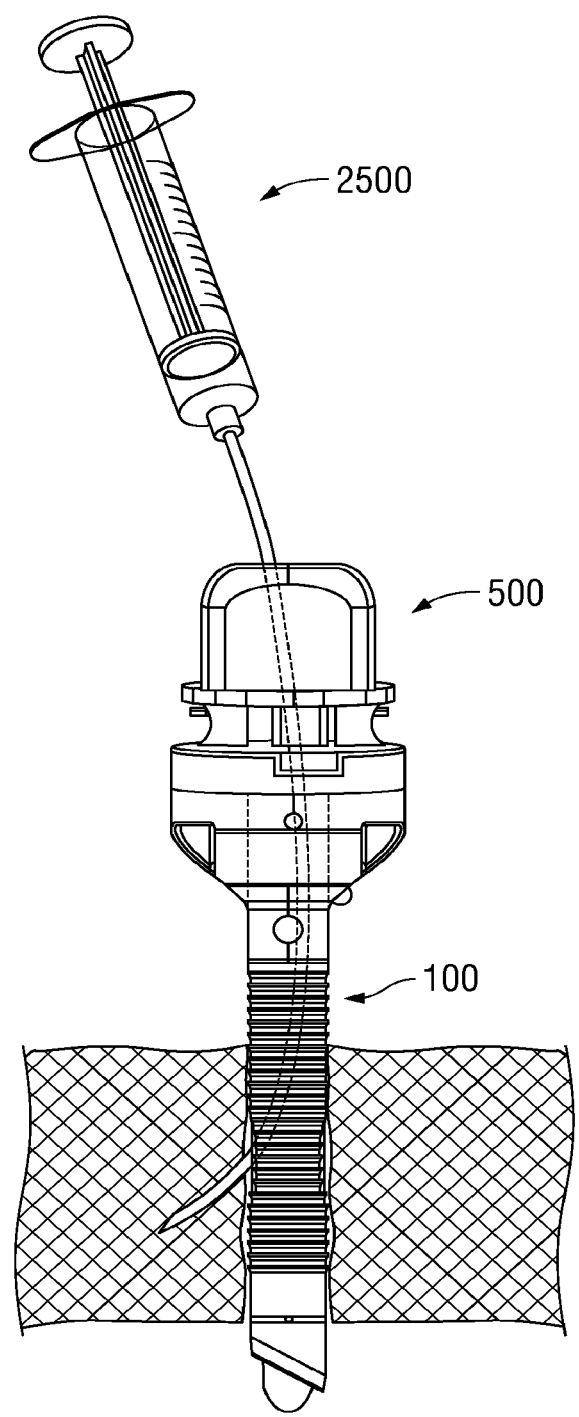
FIG. 44 is a side view of the guide member of FIG. 12A engaged within the cannula of FIG. 4A and positioned within an opening in tissue, including a syringe assembly inserted through the guide member and cannula.

With reference to FIG. 44, with respect to any of the previous embodiments, in addition to or as an alternative to inserting a suture passer through the guide member and cannula assembly, other suitable surgical instruments may be inserted through the guide member and cannula assembly to facilitate performing a surgical task, function, etc. For example, as shown in FIG. 44, guide member 500 is engaged within cannula 100, positioned within an opening in tissue, and includes a syringe assembly 2500 inserted therethrough. Syringe assembly 2500 may be configured to deliver a local anesthetic, or other drug or medicament, to tissue adjacent the opening in tissue. Due to the particular positioning of slots 106 (FIG. 4B) of cannula 100, the needle of the syringe assembly 2500 can be accurately positioned adjacent the desired portion, or layer, of tissue into which the anesthetic or medicament is to be delivered. More specifically, the needle of the syringe assembly 2500 may define a rigid, curved configuration such that, upon insertion through cannula 100, the distal tip of the needle is directed into the desired portion, or layer, of tissue into which the anesthetic or medicament is to be delivered. With respect to the delivery of local anesthetic using the transversus abdominis plane (TAP) block technique, as an example, cannula 100 and guide member 500 may be configured such that slots 106 (FIG. 4B) are positioned between the transverse abdominis muscle and the interal oblique muscle. Accordingly, the needle of syringe assembly 2500 can be accurately inserted into the fascial tissue plane between the transverse abdominis muscle and the interal oblique muscle for delivery of local anesthetic thereto.

Although detailed above and shown in FIG. 44 with respect to guide member 500, cannula 100, and a syringe assembly 2500, it is contemplated that any of the guide members and/or cannulas provided herein may be configured to receive one or more suitable surgical instruments in addition to or as an alternative to a suture passer. Such surgical instruments may be utilized, for example: to deliver an agent, e.g., drug, medicament, insufflation fluid, contrast agent, other fluid, etc., to tissue and/or the internal surgical site; to facilitate visualization, monitoring, or sensing of tissue and/or the internal surgical site; and/or to perform one or more surgical tasks, e.g., cutting tissue, clamping tissue, retrieving tissue, treating tissue with energy, etc.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A guide member configured for guiding a suture passer through a cannula and tissue surrounding the cannula to facilitate closure of an opening in tissue, the guide member comprising:

an inner shaft, the inner shaft defining an entry opening, an exit opening, and a channel extending between the entry opening and the exit opening, the inner shaft having at least one arm protruding distally from a proximal end portion of the inner shaft;

an outer sleeve disposed about the inner shaft and positioned to enclose at least a portion of the channel to define a passageway extending between the entry opening and the exit opening; and a ring having an inner annular surface defining a helical track configured to be directly threadedly engaged to the at least one arm of the inner shaft.

2. A guide member configured for guiding a suture passer through a cannula, the guide member comprising:

an inner shaft defining a channel extending between an entry opening defined in a proximal end portion of the inner shaft and a distal opening defined in a distal end portion of the inner shaft, the inner shaft having a cap fixed to the proximal end portion of the inner shaft and having at least one arm protruding distally from the cap;

an outer sleeve disposed about the inner shaft and positioned to enclose at least a portion of the channel; and a ring having an inner annular surface defining a helical track configured to be directly threadedly engaged to the at least one arm of the cap.

3. The guide member according to claim 2, further comprising a collar fixed to a proximal end portion of the outer sleeve.

4. The guide member according to claim 3, wherein the cap is configured to be coupled to the collar via the ring.

5. The guide member according to claim 2, wherein the ring has a pair of tabs extending distally therefrom.

6. The guide member according to claim 2, wherein the inner shaft has a plate-like configuration along a length thereof.

7. A guide member configured for guiding a suture passer through a cannula, the guide member comprising:

an inner shaft defining a channel extending between a proximal end portion thereof and a distal end portion thereof, the inner shaft having at least one arm protruding distally from the proximal end portion thereof;

an outer sleeve disposed about the inner shaft and positioned to enclose at least a portion of the channel; and a ring having an inner annular surface defining a helical track configured to be directly threadedly engaged to the at least one arm of the inner shaft.

8. The guide member according to claim 7, further comprising a collar fixed to a proximal end portion of the outer sleeve.

9. The guide member according to claim 8, wherein the ring surrounds the collar, such that the collar is retained between the proximal end portion of the inner shaft and the ring.

10. The guide member according to claim 7, wherein the distal end portion of the inner shaft includes a resiliently flexible tip member, the tip member configured to pass distally through a distal aperture defined in a distal end portion of the outer sleeve to a distal position and be prevented from moving proximally through the distal aperture out of the distal position, the tip member tapering in a distal direction and having a shoulder configured to engage a distal edge of the distal end portion of the outer sleeve.

* * * * *